United States Patent [19]

Oswald et al.

[11] 4,454,353
[45] Jun. 12, 1984

[54] TRIHYDROCARBYL SILYL SUBSTITUTED ALKYL DIARYL PHOSPHINE TRANSITION METAL COMPLEXES AND THEIR USE AS HOMOGENEOUS HYDROFORMYLATION-ALDOLIZATION CATALYSTS

[75] Inventors: Alexis A. Oswald, Mountainside, N.J.; Torris G. Jermansen, Staten Island, N.Y.; Andrew A. Westner, Paramus; I-Der Huang, Upper Saddle River, both of N.J.

[73] Assignee: Exxon Research and Engineering Co., Florham Park, N.J.

[21] Appl. No.: 426,663

[22] Filed: Sep. 29, 1982

Related U.S. Application Data

[60] Division of Ser. No. 295,193, Aug. 21, 1981, which is a continuation-in-part of Ser. No. 192,810, Oct. 1, 1980, which is a division of Ser. No. 11,238, Feb. 12, 1979, Pat. No. 4,298,541.

[51] Int. Cl.³ ............................................. C07C 45/50
[52] U.S. Cl. ................................... 568/454; 568/451; 568/883; 568/909; 260/429 R
[58] Field of Search .............. 568/454, 451, 883, 909; 260/429 R

[56] References Cited

U.S. PATENT DOCUMENTS

| | | | |
|---|---|---|---|
| 3,856,837 | 12/1974 | Chandra | 560/429 |
| 4,052,461 | 10/1977 | Tinker | 568/454 |
| 4,108,905 | 8/1978 | Wilkinson | 568/454 |
| 4,134,906 | 1/1979 | Oswald et al. | 560/429 |
| 4,151,114 | 4/1979 | Oswald et al. | 252/430 |
| 4,157,313 | 6/1979 | Conan et al. | 252/431 |
| 4,220,556 | 9/1970 | Oswald et al. | 252/430 |
| 4,283,562 | 8/1981 | Billing et al. | 568/454 |
| 4,287,370 | 9/1981 | Harris et al. | 568/454 |
| 4,298,541 | 11/1981 | Oswald et al. | 560/429 |

FOREIGN PATENT DOCUMENTS

| | | | |
|---|---|---|---|
| WO80/1689 | 2/1980 | PCT Int'l Appl. | 568/454 |
| WO80/1691 | 2/1980 | PCT Int'l Appl. | 568/454 |
| WO80/1692 | 2/1980 | PCT Int'l Appl. | 568/454 |
| 1342877 | 1/1974 | United Kingdom | 568/454 |
| 1419769 | 12/1975 | United Kingdom | 568/454 |
| 1420928 | 1/1976 | United Kingdom | 568/454 |

Primary Examiner—Werren B. Lone
Attorney, Agent, or Firm—Robert J. North

[57] ABSTRACT

Described is a carbonylation process using novel homogeneous trihydrocarbyl silyl-substituted alkyl diaryl phosphine transition metal complexes of the general formula:

$$[(Ar_2PQ)_ySiR_{4-y}]_g(MX_n)_s$$

wherein Ar is a $C_6$ to $C_{10}$ aromatic hydrocarbyl radical, Q is a $C_1$ to $C_{30}$ saturated straight chain divalent radical, R is a $C_1$ to $C_{10}$ hydrocarbyl, wherein Ar, Q and R, can be substituted or unsubstituted, y is 1 to 4, g times y is 1 to 6, M is a transition metal selected from the group consisting of Group VIII transition metals, X is an anion or organic ligand excluding halogen satisfying the valence and coordination sites of the metal, n is 2 to 6 and s is 1 to 3, are disclosed. These materials exhibit high thermal stability and are superior catalysts for the selective hydroformylation of olefins, particularly in the presence of excess quantities of ligand of the formula:

$$(Ar_2PQ)_ySiR_{4-y}$$

wherein Ar, Q, R, and y are as previously defined.

Specifically, tris-(trimethyl silyl-ethyl diphenyl phosphine) rhodium carbonyl hydride, $$[(CH_3)_3Si-CH_2CH_2-PPh_2]_3Rh(CO)H$$

and tris [bis-(diphenylphosphinoethyl)dimethyl silane] rhodium carbonyl hydride, $$[(CH_3)_2Si-CH_2CH_2-PPh_2]_3Rh(CO)H,$$

are selective olefin hydroformylation catalysts, particularly in the presence of excess trihydrocarbyl silyl-substituted alkyl diaryl phosphine ligand.

16 Claims, 9 Drawing Figures

KEY STEPS AND EQUILIBRIA IN THE MECHANISM OF PHOSPHINE - RHODIUM COMPLEX CATALYZED HYDROFORMYLATION OF OLEFINS

KEY STEPS AND EQUILIBRIA IN THE MECHANISM OF PHOSPHINE – RHODIUM COMPLEX CATALYZED HYDROFORMYLATION OF OLEFINS

SCHEME OF AUTOCLAVE FOR HYDROFORMYLATION

TRIHYDROCARBYL SILYL SUBSTITUTED ALKYL DIARYL PHOSPHINE TRANSITION METAL COMPLEXES AND THEIR USE AS HOMOGENEOUS HYDROFORMYLATION-ALDOLIZATION CATALYSTS

CROSS REFERENCE TO RELATED APPLICATIONS

This is a division of application Ser. No. 295,193, filed Aug. 21, 1981 which is a continuation-in-part application of U.S. Ser. No. 192,810 filed Oct. 1, 1980, which is a Rule 60 divisional of Ser. No. 11,238 filed Feb. 12, 1979 which is now U.S. Pat. No. 4,298,541, issued Nov. 3, 1981.

BACKGROUND OF THE INVENTION

This invention relates to trihydrocarbyl silyl-substituted alkyl diaryl phosphine transition metal complex carbonylation catalysis.

More particularly, the subject of this invention is homogeneous, selective, low pressure alpha-olefin hydroformylation with tris-(silylalkyl diaryl phosphine) rhodium carbonyl hydride complex catalysts in the presence of excess phosphine ligand.

One aspect of the invention is the derivation of the silylalkyl diphenyl phosphine ligands via the anti-Markovnikov addition of a diaryl phosphine to the appropriate alkenyl silane.

Another aspect is concerned with the preparation of the transition metal complexes of these ligands via displacement reactions. Syntheses starting with tris(triphenyl phosphine) rhodium carbonyl hydride and dicarbonyl acetylacetonato rhodium are specifically described.

A special aspect of the invention is concerned with the physicochemical and catalytic properties of the novel complexes, i.e., phosphine basicity and stereochemistry versus complex formation, equilibria and stability. The selectivity and rate of hydroformylation are correlated with temperature, concentration of excess ligand, carbon monoxide partial pressure and the presence of aldolization catalyst.

Finally, a special concern of the present invention is a continuous low pressure hydroformylation of alpha-olefins, particularly butene-1, propylene and pentenes at elevated temperatures. An exemplary feature of such hydroformylation involves a continuous product flash-off operation. In this process, gaseous reactants are continuously introduced into, and a mixture of gaseous products and unreacted feed is continuously removed from, the solution of the present homogeneous catalyst complex.

The main objective of the present invention is to provide selective silyl substituted alkyl diphenyl phosphine rhodium carbonyl hydride catalysts which are more stable, and can be used in an improved hydroformylation process at higher temperatures, than the widely used triaryl phosphine rhodium carbonyl hydride catalysts.

Transition metal complexes of both triphenyl phosphine and trialkyl phosphines are widely studied catalysts employed in hydroformylation, hydrogenation, etc., reactions. The monograph of Juergen Falbe, "New Syntheses with Carbon Monoxide," Springer Verlag, N.Y., 1970, deals with the use of these materials in reactions of carbon monoxide, particularly carbonylations. In the realm of rhodium catalyzed hydroformylations of alpha-olefins, catalyst systems of triaryl phosphine and other trivalent phosphorus compound rhodium complexes in the presence of excess phosphine ligand which exhibited improved selectivity to normal aldehydes (over iso aldehydes) are described by R. L. Pruett and J. A. Smith in U.S. Pat. No. 3,527,809. In that patent, it is stated as being essential that the phosphorus ligands be of weakly basic character possess a half neutralization potential value at least 425, preferably at least 500, smaller than that of N,N' diphenylguanidine. The Δ HNP is only about 400 for simple alkyl diphenyl phosphines, which are too basic according to Pruett and Smith.

Morrell and Sherman in German Offenlegungschrift No. 2,802,922 disclose unsubstituted alkyl diphenyl phosphines as components of stabilized tris-(triphenyl phosphine) rhodium carbonyl hydride plus excess triphenyl phosphine catalyst systems for hydroformylation of alpha-olefins with CO/H$_2$ to give aldehydes.

In the area of silyl substituted alkyl phosphine transition metal complexes, the work of Grish Chandra is of importance. British Pat. Nos. 1,419,769; 1,420,982; 1,421,136 by Chandra disclose rhodium complexes of silyl alkyl phosphines, in each of which the rhodium had attached to it a halogen. These materials are disclosed as being useful for hydro-silylation, hydrogenation and hydroformylation. Specific examples are given only for the preparation of silylmethyl phosphine complexes and their use in hydrosilylation.

British Pat. Nos. 1,412,257; 1,414,662 and U.S. Pat. No. 3,856,837 (all to Chandra) describe nickel, palladium and platinum complexes of silylalkyl phosphines and their use of hydrosilylation, hydrogenation, and polymerization. In these patents, the transition metal has attached to it a halogen or —SCN group or —SZ wherein Z represents an alkyl radical having less than 18 carbon atoms or the phenyl radical.

In G.B. Pat. No. 1,412,257 the material is identified as a bridged binuclear complex.

In G.B. Pat. No. 1,414,662 the nickel, palladium or platinum transition group metal may have associated with it a hydrogen atom or other anionic ligand (X) which may be for example, H, Cl, Br, I, —NO$_2$, —NO$_3$, —SCN, —OCOCH$_3$, an alkyl, aryl, alkaryl or aralkyl radical. However, materials wherein X is Br are the only ones actually prepared.

In U.S. Pat. No. 3,856,837, the nickel, palladium or platinum also have only halogens associated with them as anionic ligands (X).

G.B. Pat. No. 925,721 to H. Niebergall deals broadly with the addition of secondary phosphines to unsaturated silanes to provide silylhydrocarbyl phosphines. He discloses materials of the formula:

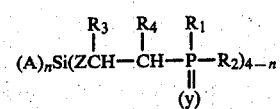

wherein R$_1$ and R$_2$ are alkyl, cycloalkyl, aryl, alkaryl, aralkyl; R$_3$ and R$_4$ are alkyl, cycloalkyl, aryl, alkaryl, aralkyl or hydrogen; A is a halo, alkoxy, hydroxy, alkyl, alkaryl, cycloalkyl, aryl or aralkyl radical; Z is a hydrocarbon residue having from 1 to 10 carbon atoms and is preferably a saturated straight or branched chain hydrocarbon residue (or Z is a silicon to carbon linkage). If phosphorous is pentavalent, y is oxygen or sulfur; if phosphorous is trivalent, y is no substituent; n is 0 to 3. This patent contains no teaching that these materials can be complexed with transition metals to yield homogeneous catalysts useful in hydroformylation reactions.

Owen and Cooper disclose the preparation of similar compounds via displacement reactions of chlorophosphines and silylalkyl Grignard compounds or sodium phosphides and silylalkyl halides in British Pat. No. 1,179,242.

To obtain the vinyl triphenyl silane intermediate, vinyl trichloro silane was reacted with phenyl magnesium bromide in an ether-THF solvent mixture. The cement reactions of chloro-phosphines and silylalkyl Grignard compounds or sodium phosphides and silylalkyl halides.

U.S. Pat. No. 3,067,227 to Fekete describes the preparation of alkoxysilylalkylphosphines via the method of reacting alkoxy silanes and unsaturated phosphines.

G.B. Pat. No. 1,182,763 to Jacques and Owen also disclose silylhydrocarbylphosphine intermediates useful in the preparation of the complexes of the present invention.

U.S. Pat. No. 3,726,809 and 3,832,404 to Allum et al disclose heterogeneous hydroformylation catalysts (and processes using these catalysts). These heterogeneous catalysts are silylhydrocarbyl phosphine transition metal complexes, bonded to a support by the interaction of a reactive group on the silicon with at least one reactive hydroxyl group on the support which may also be silicon. See also U.S. Pat. No. 3,907,852 and 4,083,803 to Oswald and Murrell.

SUMMARY OF THE INVENTION

Figure 1:
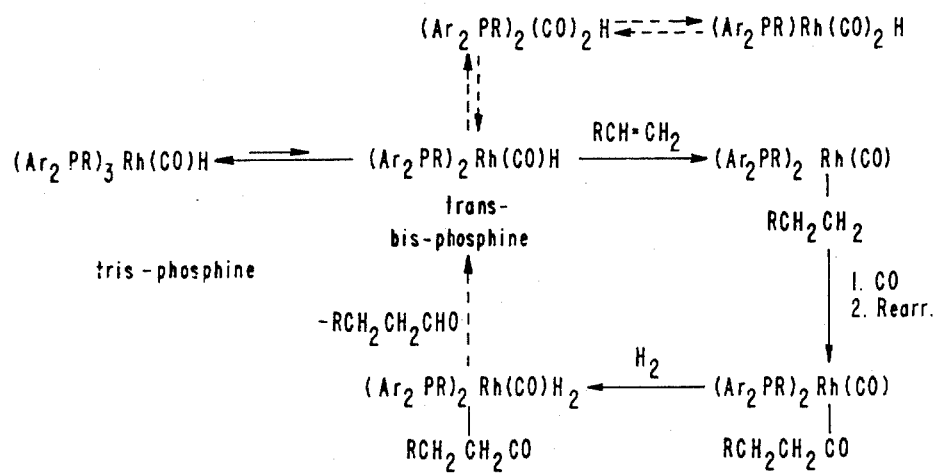
FIG. 1 shows the key steps and equilibria in the phosphine rhodium complex catalyzed hydroformylation of olefins.

By this invention, there is provided a carbonylation process comprising reacting an organic compound with CO in the presence of reaction mixture comprising a catalyst complex of the formula:

wherein Ar is a substituted or unsubstituted $C_6$ to $C_{10}$ aromatic radical, Q is a substituted or unsubstituted $C_1$ to $C_{30}$ saturated open chain alkylene radical, R is an unsubstituted or monosubstituted $C_1$ to $C_{10}$ hydrocarbyl radical, M is a Group VIII transition metal selected from the group consisting of Co, Rh, Ir, Ru, Fe or Os, X is an anion or organic ligand, excluding halogen, satisfying the valence and coordination sites of the metal, y is 1 to 4, g is 1 to 6 with the proviso that g times y is 1 to 6, n is 2 to 6, and s is 1 to 3, said substituents on said aromatic radicl, on said alkylene radical and on said hydrocarbyl radical being chemically unreactive with materials used in, and the products of, a carbonylation reaction.

DESCRIPTION OF THE INVENTION AND PREFERRED EMBODIMENTS

Compositions encompassed and used in the present invention process are hydrocarbylsilyl alkyl diaryl phosphine complexes of selected Group VIII transition metals free of metal bound halogen. The scope of the compositions is co-extensive with that described in the parent case, Ser. No. 011,238, which is now U.S. Pat. No. 4,298,541, issued Nov. 3, 1981, which is hereby incorporated by reference for that purpose. They are represented by the formula:

wherein Ar is the same or different $C_6$ to $C_{10}$ substituted or non substituted aromatic hydrocarbyl radical, preferably phenyl, mono-, di- or tri- substituted phenyl, most preferably phenyl; Q is a $C_1$ to $C_{30}$ saturated open chain alkylene radical, preferably a straight chain alkylene radical, more preferably a $C_2$ to $C_{14}$ unsubstituted or monosubstituted alkylene diradical; R is the same or different $C_1$ to $C_{10}$ unsubstituted hydrocarbyl or $C_1$ to 6 unsubstituted hydrocarbyl radical, preferably $C_1$ to $C_6$ alkyl, $C_5$ and $C_6$ cycloalkyl, phenyl, $C_1$ to $C_6$ monosubstituted alkyl, monosubstituted phenyl, more preferably $C_1$ to $C_6$ alkyl or phenyl, M is a Group VIII transition metal selected from Fe, Co, Rh, Ru, Ir, Os, preferably Co, Rh, Ir, and Ru, more preferably Co, Rh, most preferably Rh; y is 1 to 4, preferably 1 or 2, most preferably 1; g is 1 to 6 and g times y is 1 to 6, preferably 1 to 4, more preferably 2 or 3, most preferably 3; X is an anion or organic liquid which satisfies the valence and coordination sites of the metal, with the proviso that X cannot be halogen, preferably X is H, CO and tertiary phosphine, most preferably H, CO; n is 2 to 6, preferably 2; s is 1 to 3. Preferably all the organic radicals are unsubstituted. However, if said Ar, R and Q moieties are substituted, the substituents must generally be unreactive with the products of, and during, carbonylation reaction and particularly during hydroformylation reaction. Representative non-limiting examples are described below.

Representative examples of the aromatic Ar groups include phenyl, fluorophenyl, difluorophenyl, tolyl, xylyl, benzoyloxyphenyl, carboethoxyphenyl, acetylphenyl, ethoxyphenyl, phenoxyphenyl, biphenyl, naphthyl, hydroxyphenyl, carboxyphenyl, trifluoromethylphenyl, tetrahydronaphthyl, furyl, pyrryl, methoxyethylphenyl, acetamidophenyl, dimethylcarbamylphenyl, and the like. If substituted, mono- and disubstituted phenyl groups are preferred.

Preferred substituents of the Ar aromatic groups include $C_1$ to $C_{30}$, preferably $C_1$ to $C_{12}$ alkyl, alkoxy, acyl, acyloxy, acrylamido, carbamido, carbohydrocarbyloxy, halogen, phenoxy, hydroxy, carboxy and the like.

Representative R organic groups include $C_1$ to $C_{10}$ hydrocarbyl, preferably $C_1$ to $C_6$ unsubstituted alkyl, and particularly preferred, phenyl, and $C_1$ to $C_3$ alkyl. Specific examples include methyl, propyl, hexyl, cyclohexyl, methylcyclopentyl, i-propyl, decyl, fluoropropyl benzyl, phenyl, naphthyl, fluorophenyl, tolyl, and the like. Particularly preferred R groups are methyl and phenyl.

The Q moiety in the composition include substituted and unsubstituted divalent alkylene radicals bridging the P and Si atoms. When unsubstituted, the polymethylene radical is the formula $(CH_2)_m$ wherein m is 2 to 14, preferably 2 to 3, and particularly preferred being 2, ethylene. The first segment of the Q alkylene group bound to the phosphorous is preferably a —$CH_2CH_2$— group. Such a group is desired to avoid undue steric hindrance of the phosphine ligand. When the Q radical is substituted, the alkylene chain can also be interrupted with a heteroatom such as ether oxygen, sulfide, and the like, and also by the phenylene group.

Representative examples of Q radicals include ethylene, trimethylene, tetradecamethylene, xylylene, oxy-bis ethyl, sulfone-bis ethyl, trimethylsilylethyl substituted trimethylene, and the like.

Representative examples of anions and organic ligands, represented by the symbol X, are the following: $H^-$, $alkyl^-$, $aryl^-$, substituted $aryl^-$, $CF_3^-$, $C_2F_5^-$, $CN^-$, $N_3^-$, $COR^-$, where R is alkyl or aryl, acetate, acetylacetonate, $SO_4^{2-}$, $PF_4^-$, $NO_2^-$, $NO_3$, $O_2^-$, $CH_3O^-$, $CH_2=CHCH_2-CO$, $C_6H_5CN$, $CH_3CN$, NO, $NH_3$, pyridine $C_4H_9)_3P$, $(C_2H_5)_3N$, chelating olefins, diolefins and triolefins, tetrahydrofuran, $CH_3CN$, triphenyl phosphine. Preferred organic ligands are H, CO and tertiary phosphine and most preferably H and CO. Halogens may not be directly bonded to the transition metal.

Representative examples of groups represented by the symbol $(MX_n)_s$ are $Rh(CO)H$, $Ir(CO)H$, $Co(CO)_3H$ $Ru(CO)_2H$, and particularly preferred is $Rh(CO)H$.

The values of the integers represented by the symbols y, n, s, g in the above-defined formula depend on the number of monoversus divalent organic radical substituents (R vs. Q) on the silicon, and the coordination number of the metal. Accordingly, these values, as defined above, are interrelated to satisfy the valence requirements of the silicon and the transition metal.

Although the complex catalyst compositions of the present invention are preferably non-charged, they include compounds containing positively charged transition metal, particularly rhodium. These complexes are preferably of the general formula:

$$[Ar_2P(CH_2)_mSiR_3]_2Rh^+(CO)_3X^-$$

wherein the meaning of Ar, R and m is the same as before, and $X^-$ is an anion, preferably a non-coordinating anion, preferably selected from the group consisting of borate, aluminate, perchlorate, sulfonate, nitrate, fluorophosphate, and fluorosilicate. Representative examples of formulas include $PH_4B^-$, $F_4B^-$, $ClO_4^-$, $Ph_3SO_3^-$, $CF_3SO_3^-$, $NO_3^-$, $F_6P^-$, and $F_6Si_2^{2-}$.

Dependent on the subclass of the silylalkyl phosphine component used as an intermediate different types of the present complexes are derived, wherein the value of g is 1 to 6 and the value of g times y is 1 to 6; i.e.,

| | |
|---|---|
| $[Ar_2PQSiR_3]_g \cdot (MX_n)_s$ | g = 1–6; y = 1 |
| $[(Ar_2PQ)_2SiR_2]_g \cdot (MX_n)_s$ | 2g = 1–6; y = 2 |
| $[(Ar_2PQ)_3SiR]_g \cdot (MX_n)_s$ | 3g = 1–6; y = 3 |
| $[(Ar_2PQ)_4Si]_g \cdot (MX_n)_s$ | 4g = 1–6; y = 4 |

Preferred hydroformylation catalyst compositions of the present invention are non-chelated trisphosphine and bisphosphine rhodium carbonyl hydride compositions of the generic formulae:

$$[(Ar_2PQ)_ySiR_{4-y}]_g \cdot Rh(CO)H, \text{ and}$$

$$\{[Ar_2P(CH_2)_m]_ySiR_{4-y}\}_gRh(CO)H$$

wherein the meaning of Ar and R is as previously defined; m is 2 to 14, preferably 2 to 3, most preferably 2; y is 1 to 4, preferably 1 to 3, most preferably 2; g is 2 to 3, preferably 3.

Among this class of trihydrocarbylsilyl alkyl phosphine rhodium complexes, preferred subgeneric classes are the following:

$$\{[(Ar_2P(CH_2)_m]SiR_3\}_3Rh(CO)H$$

$$\{[(Ar_2P(CH_2)_m]SiR_2\}_3Rh(CO)H$$

$$\{[Ar_2P(CH_2)_m]_3SiR\}_3Rh(CO)H$$

$$\{[(Ar_2P(CH_2)_m]_4Si\}_3Rh(CO)H$$

Some specifically preferred silylalkyl phosphine rhodium complexes possess short straight chain alkylene bridges between Si and P, e.g., $$[(\phi_2P(CH_2)_m]_ySiR_{4-y}]_g[Rh(CO)H]$$

wherein m is 2 to 14, preferably 2 to 3, R being $C_1$-$C_6$ alkyl, and wherein the complexes can be oligomeric whenever the silylalkyl phosphine has more than one phosphine group.

Among the preferred subgeneric examples of such compositions are the following:

$$[\phi_2P(CH_2)_mSi(CH_3)_3]_3Rh(CO)H$$

$$[\phi_2P(CH_2)_mSi\phi_3]_3Rh(CO)H$$

$$\{[\phi_2P(CH_2)_m]_2Si\phi_2\}_3Rh(CO)H$$

$$\{[\phi_2P(CH_2)_m]_2Si(CH_3)_2\}_3Rh(CO)H$$

$$\{[\phi_2P(CH_2)_m]_3SiCH_3\}_3Rh(CO)H$$

$$\{[\phi_2P(CH_2)_m]_4Si\}_3(Rh(CO)H)_s$$

Representative examples of specifically preferred rhodium complexes which are non-limiting include:

$$[Ph_2PCH_2CH_2Si(CH_3)_3]_3Rh(CO)H$$

$$[Ph_2PCH_2CH_2Si(n\text{-}C_3H_7)_3]_3Rh(CO)H$$

$$[Ph_2PCH_2CH_2SiPh_3]_3Rh(CO)H$$

$$[(Ph_2PCH_2CH_2)_2Si(CH_3)_2]_3Rh(CO)H$$

$$[PH_2PCH_2CH_2CH_2Si(CH_3)_3]_3Rh(CO)H$$

$$[Ph_2PCH_2Si(CH_3)_3]_3Rh(CO)H$$

$$[(Ph_2PCH_2CH_2CH_2)_2Si(CH_3)_2]_3Rh(CO)H$$

[(Ph$_2$PCH$_2$CH$_2$)$_2$SiPh$_2$]$_3$Rh(CO)H

[(Ph$_2$PCH$_2$CH$_2$)$_3$Si(CH$_3$)]$_3$Rh(CO)H

[(Ph$_2$PCH$_2$CH$_2$)$_4$Si]$_3$(Rh(CO)H)$_s$

Examples of preferred types of subgeneric complexes of other transition metals are:

($\phi_2$PQSiR$_3$)$_3$Ir(CO)H ($\phi_2$PQSiR$_3$)$_2$Ru(CO)$_2$H$_2$ ($\phi_2$PQSiR$_3$)Co(CO)$_3$H Specific non-limiting examples of the above are the following:

{[$\phi_2$PCH$_2$CH$_2$Si(CH$_3$)$_3$]Co(CO)$_3$}$_2$

[$\phi_2$PCH$_2$CH$_2$CH$_2$Si$\phi_3$]$_3$Ir(CO)H

[$\phi_2$PCH$_2$CH$_2$Si(n-C$_3$H$_7$)$_3$]Ru(CO)$_2$H$_2$

Preparation of Complexes and Silylalkyl Phosphine Intermediates Therefor

For the preparation of the present compositions, standard methods of organometallic chemistry synthesis are discussed in a comprehensive text, "Advanced Inorganic Chemistry" by F. A. Cotton and G. Wilkinson (Interscience Publishers, New York, 1972) and are exemplified in the series on "Inorganic Syntheses" particularly volume XV, edited by G. W. Parshall and published by McGraw-Hill Book Co., New York, 1974, and in U.S. Pat. No. 4,052,461 by H. B. Tinker and D. E. Morris.

For the preparation of the rhodium complexes, one of the specifically preferred direct method of synthesis starts with rhodium chloride. This method can be employed, e.g., for the synthesis of tris-(trihydrocarbylsilylalkyl diaryl phosphine) rhodium carbonyl hydride according to the following general scheme:

$$RhCl_3 \cdot 3H_2O \xrightarrow[CH_2O \text{ aq., KOH ethanolic}]{Ar_2PQSiR_3 \text{ (excess)}}$$

[Ar$_2$PQSiR$_3$]$_3$Rh(CO)H

Other preferred direct methods of complex preparation include the reaction of transition metal carbonyls or oxides, such as those of rhodium with the silylalkyl phosphine ligand and CO/H$_2$. Specifically preferred is the use of dicarbonyl acetylacetonate rhodium to form the subject process complex is in which excess silyl phosphine ligand is reacted with the carbonyl complex and the resulting complex reduced with hydrogen. Organic salts of transition metals such as acetates can also be reacted with the ligand.

The complexes can also be prepared via an indirect method by reaction of the corresponding complexes of a triaryl phosphine, preferably triphenyl phosphine, with the desired silylalkyl phosphine ligand, as defined hereinabove, preferably in excess, e.g., ($\phi_3$P)$_3$Rh(CO)H + 3$\phi_2$PQSiR$_3$ → ($\phi_2$PQSiR$_3$)$_3$Rh(CO)H + 3$\phi_3$P.

This ligand exchange method is one of the preferred embodiment in the process. The above ligand exchange methods involving dicarbonyl acetylacetonate rhodium and (PH$_3$P)$_3$Rh(CO)H can be preferably used to form the active catalyst in situ during the process, especially during hydroformylation. The silyl ligand used is [(Ar$_2$PQ)$_y$Si$_{4-y}$], as defined herein.

In the case of rhodium catalysts, it is essential that the final complex formation be conducted in the absence of reactive halogen, i.e., metal bound halogen. Presence of halide in rhodium hydroformylation has been found to lead to severely reduced catalytic activity. Preferably less than 1 ppm by weight of halide ion, e.g., chloride ion, is present per gram of phosphine ligand in the reaction medium.

The above methods are also applicable to forming useful complexes in the subject process where the metal is Fe, Co, Ru, Os and Ir.

In general, the silylalkyl diaryl phosphine ligands are more basic than the corresponding triaryl phosphines. This basicity difference is a positive factor in the above ligand substitutions providing the novel, completely or partially exchanged complexes, e.g., $$(\phi_2PSiR_3) + (\phi_3P)_2Rh(CO)H \xrightarrow{+\phi_2PQSiR_3}$$

($\phi_2$PQSiR$_3$)$_2$($\phi_3$P)Rh(CO)H $$\downarrow \phi_2PQSiR_3$$

($\phi_2$PQSiR$_3$)$_3$Rh(CO)H

The intermediate silylalkyl phosphine ligands employed in the present invention are prepared by any number of standard techniques. U.S. Pat. No. 3,907,852 and 4,083,803 to Oswald and Murrell and G.B. 925,721 to Niebergall are representative of techniques which may be successfully employed to prepare the intermediates.

One preferred synthesis technique involves the addition of diaryl phosphines to unsaturated silanes:

yAr$_2$PH + [CH$_2$=CH(CH$_2$)$_k$]$_y$SiR$_{4-y}$ → {[Ar$_2$PCH$_2$CH$_2$(CH$_2$)$_k$]$_y$SiR$_{4-y}$ wherein k ranges from 0 to 28 and y ranges from 1 to 4. Such additions are preferably carried out via a radical mechanism in a free radical manner employing either a chemical initiator such as azobisisobutyronitrile, or radiation initiator. It is preferred that such reactions be conducted in the presence of from a 5 to 100% excess over the stoichiometric amount required of the phosphine. Use of this excess has been found to improve the selectivity of the process.

It has also been observed that additions of phosphines to vinylic silanes (k=0) occur with ease in the presence of radiation particularly ultraviolet light. The reactivity of the vinyl silanes is in marked contrast to the rather sluggish behavior of the olefins having analogous structures. In addition to the vinyl silanes, allyl silanes (k=1) are another preferred class of reactant.

Another technique which may be employed in the preparation of the silyl hydrocarbyl phosphine intermediate involved in the present invention is the addition of silanes to unsaturated phosphines:

yAr$_2$P(CH$_2$)$_k$CH=CH$_2$ + H$_y$SiR$_{4-y}$ → [Ar$_2$P(CH$_2$)$_k$CH$_2$CH$_2$]$_y$SiR$_{4-y}$ wherein k ranges from 0 to 28 and y ranges from 1 to 4.

These additions occur in an anti-Markovnikov manner via the mechanism discussed by C. Eaborn in the monograph "Organosilicon Compounds," Academic Press, Inc., Publishers, New York, 1960, and in the patent references previously identified. Again, the preferred reactants are the vinylic and allylic materials, this time the phosphines.

Other methods for silylalkyl phosphine preparation employ displacement reactions. One type of reaction starts with phosphides, particularly alkali metal phosphides, and chloro-, bromo-, or iodo-alkyl silanes:

$$yAr_2PMe + [Z(CH_2)_m]_ySiR_{4-y} \rightarrow [Ar_2P(CH_2)_m]_ySiR_{4-y} + MeZ$$

wherein Me is Na, K, Li; m is 1 to 30; Z is Cl, Br, I. It is important that monophenylalkylphosphine be absent to insure high reactivity and purity of the final product. Another technique starts with diaryl chloro or bromo phosphines and the corresponding Grignard derivatives of the silicon compounds:

$$Ar_2PZ + [ZMg(CH_2)_m]_ySiR_{4-y} \rightarrow [Ar_2P(CH_2)_m]_ySiR_{4-y} + yMgZ_2$$

wherein Z is chlorine, bromine. Particular care is to be taken to remove all impurities containing reactive halogen, e.g. by the extraction of the product by aqueous caustic

CARBONYLATION PROCESSES EMPLOYING HOMOGENEOUS SILYLALKYL PHOSPHINE-TRANSITION METAL COMPLEX CATALYSTS

It has been discovered that carbonylation reactions, particularly hydroformylation reactions, which involve the reaction of unsaturated organic compounds with CO, or CO and hydrogen mixtures can be successfully practiced in the presence of catalytically effective amounts of silylalkyl diaryl phosphine-Group VIII Transition metal complexes, described hereinabove. Carbonylation reactions are described in detail in the earlier referred to Falbe monograph. Main types of carbonylation reactions catalyzed by the present complexes are the Roelen reaction (hydroformylation) of olefins with CO and H and subsequent aldolization reactions; the Reppe reaction (metal carbonyl catalyzed carbonylation) mainly of olefins, acetylenes, alcohols and activated chlorides with CO alone or with CO plus either alcohol or amine or water; and ring closure reactions of functional unsaturated compounds such as unsaturated amides with CO. The organic reactants are preferably olefinically unsaturated compounds, more preferably olefinic hydrocarbons.

The most preferred type of carbonylation reaction, encompassed within the scope of the subject invention process, is a selective hydroformylation comprising reacting a $C_n$ olefinically unsaturated compound with a mixture of carbon monoxide and hydrogen in the presence of a hydrocarbyl silylalkyl diaryl phosphine halogen free rhodium complex as a catalyst, as described hereinabove, to produce mainly a $C_{a+1}$ aldehyde, preferably via hydroformylation at the less substituted vinylic carbon. By the term "$C_n$", as used herein, is meant an olefinically unsaturated compound containing "n" carbon atoms. By the process of hydroformylation, through which the elements of formaldehyde, i.e., H and CHO, are added to a double bond linkage, a $C_n$ olefinically unsaturated organic compound will be converted to a $C_{n+1}$ aldehyde, assuming hydroformylation of one double bond. Where said $C_n$ compound contains more than one double bond, the carbon number will be increased by one for each double bond undergoing hydroformylation. Thus, multiple hydroformylation of a diolefin and higher is also encompassed within the intent of this subject process. Where said $C_{n+1}$ aldehyde further undergoes aldolization, the resulting compound is termed herein, a $C_{2n+2}$ aldol aldehyde. In addition to the aldol aldehyde, higher aldehydes are also formed, such as trimers, tetramers and the like.

Preferred catalysts for use in the subject hydroformylation process are of the formula:

$$\{[(C_6H_5)_2P(CH_2)_m]_ySiR_{4-y}\}_g[Rh(CO)H]$$

wherein m ranges from 1 to 30, preferably 2 to 14, most preferably 2 to 3; y ranges from 1 to 4, preferably 1 or 2, most preferably 1; g is 2 to 3, most preferably 3; R is $C_1$ to $C_6$ alkyl or phenyl, preferably methyl, ethyl, n- or i- propyl or phenyl.

Specific preferred catalysts are:

$$\{[(C_6H_5)_2P(CH_2)_2]_2Si(CH_3)_2\}_3[Rh(CO)H];$$

$$\{[(C_6H_5)_2P(CH_2)_2]Si(CH_3)_3\}_3Rh(CO)H;$$

$$\{[(C_6H_5)_2PCH_2CH_2]_3SiCH_3\}_3Rh(CO)H; \text{ and}$$

$$\{[(C_6H_5)_2PCH_2CH_2]_4Si\}_3Rh(CO)H;$$

and particularly the first two species.

Particularly in the case of the rhodium complex hydroformylation catalysts, organic solvents, other than simple hydrocarbons can be used which are preferably of weak, nonsubstituting ligand character. Representative solvents include triaryl phosphines, such as triphenyl phosphine; triaryl stibines; triaryl arsines. Other representative organic solvents are ketones such as acetophenone, diphenyl ketone; hydrocarbyloxyethyl alcohols, including phenoxyethanol, and methoxytriglycol; polyethylene glycol, 2-ethylhexylacetate, dipropyl adipate, ethylene glycol diacetate, 1,4-butanediol, dimethyl formamide, n-methylpyrrolidine, 4-hydroxybutyl-2-ethylhexanoate, organic silicone compounds such as diphenyl dipropyl silane, and the like. More preferred ligand solvents are triaryl phosphines, or an excess of the same silylalkyl phosphine ligand $[(Ar_2PQ)_ySi_{4-y}]$, as described hereinabove, which is complexed with the $(MX_n)_s$ group. In general, the preferred solvents, particularly the ligands, stabilize the catalyst system and increase its selectivity, particularly the ratio of linear versus branched products.

In case of continuous hydroformylations of olefins, particularly higher olefins, ethylene wherein the volatile primary aldehyde reaction products are continuously removed, the nonvolatile secondary condensation products tend to become the main solvents. Such inert, nonvolatile oxygenated organic solvents, preferably of carboxylic ester and alcohol character, are advantageously used.

The hydroformylation of olefins can be advantageously run in the present process in a manner coupling it with aldol condensation. The catalyst useful in combined hydroformylation-aldolization is the rhodium catalyst complex of the above-described general subject formula. For example, in the case of butene-1, the following conversions can be carried out in a combined process:

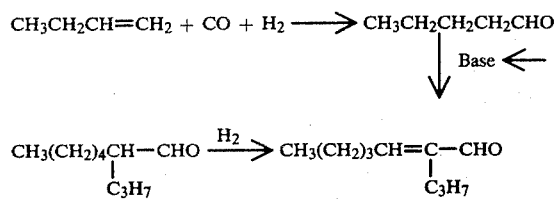

To realize such a conversion of a $C_n$ olefin to an unsaturated or saturated $C_{2n+2}$ aldol aldehyde, the present catalyst systems preferably contain a base aldol condensation catalyst such as KOH. A preferred concentration of the base, i.e., alkali hydroxide, is between about 0.01 and 1%, and preferably between 0.05 and 0.5 wt% of the total reaction mixture.

To insure high n.i. ratios in the process, preferably ether alcohols are utilized as solvents such as methoxytriglycol, phenoxy-ethanol and the like to insure preferably a homogeneous reaction medium.

Further details of the process include the necessary use of an isolation/recovery step wherein at least a portion of liquid reaction mixture is removed from the reaction zone in the process and recovering the product $C_{2n+2}$ aldehyde, thereby conventional methods. Hydrogenated products of the resulting aldol aldehydes are also formed in the reaction mixture, which can be insolated. A preferred catalyst for use in the process is tris(2-trimethylsilylethyl diphenyl phosphine) rhodium carbonyl hydride. Preferably the $H_2/CO$ molar ratio is greater than three, the ligand/Rh metal molar ratio is greater than 140, and the temperature is between 120°-175° C. Further description of the details of the general process using similar Rh-type catalysts can be found in Ser. No. 120,971 and PCT US80/00213, published Aug. 21, 1980, both hereby incorporated by reference.

Hydroformylation Process Conditions

The carbonylation processes catalyzed by the present silylalkyl phosphine catalysts described herein can be carried out advantageously under the usual reaction conditions such as those described in the earlier referenced Falbe monograph.

The reaction and particularly the rhodium complex catalyzed hydroformylation of olefinic compounds, preferably olefins in the 2 to 40 carbon range, especially olefinic hydrocarbons such as mono-, di- and triolefins can be advantageously carried out, however, over a broad range of process conditions. This above-stated carbon range is not limiting, however, since uncrosslinked polybutadiene of MW up to 15,000, and the like, is also operable.

The olefinic reactants in the present hydroformylation process can be terminally or internally unsaturated and be linear or branched open chain or of cyclic structure. The internal olefins must contain at least one, preferably two, hydrogens on the vinylic carbons. Details of olefin reactivities are incorporated by reference to Ser. No. 120,971. Terminally olefinic reactants, particularly alpha-olefins are preferred. Among the most preferred olefin reactants are $C_2$ to $C_{12}$ olefins. Representative examples include 1-tricosene, cyclohexane, ethylene, propylene, butenes and pentenes, hexenes, octenes, decenes, dodecenes, and the like particularly propylene, 3-methylbutene-1, butene-1, butene-2, including cis and trans isomers, isobutylene, 2-ethylexene-1, octene-1, hexene-1, hexene-3, pentene-1, octene-1, ethylene, and mixtures thereof. Particularly preferred are propylene, butene-1 and mixtures thereof with butene-2.

Exemplary diolefin reactants are divinyl cyclohexane and 1,7-octadiene. Di-and polyolefin reactants are preferably non-conjugated in character.

Substituted olefinic reactants can be also advantageously used as long as the substituent does not interfere with the catalyst system and is stable under the reaction conditions. Exemplary substituted olefins are acrylonitrile, methyl acrylate, trivinyl cyclohexane acroleindimethyl acetal, allylacetate, allyl t-butyl ether allyl alcohol, methyl oleate, 3-butenyl acetate, diallyl ether, allyl chlorobenzene, dicyclopentadiene, 6-hydroxyhexene.

It is to be noted that refinery streams of olefins, containing paraffin by-products such as $C_1$-$C_{10}$ paraffins, inert gases, or entrained inert aromatics, are also applicable within the scope of this invention process.

The hydroformylation of a $C_n$ olefin, with the exception of ethylene, leads to a mixture of terminally and internally substituted $C_{n+1}$ aldehydes. For example, the hydroformylation of propylene leads to a mixture of iso- and n-butyraldehydes and hydroformylation of butene-1 leads to a mixture of $C_5$ aldehydes, n-valeraldehyde and isovaleraldehyde, said mixtures having an "n/i" ratio of products. The subject process, in general, can yield high n/i ratios during hydro formylation of about 4:1 and higher.

Concentrations of the transition metal complex catalysts and particularly the preferred rhodium complex catalysts can be employed in the range of about $1\times10^{-6}$ to $1\times10^{-1}$ mole metal complex per liter of reaction mixture. Preferred concentrations are in the range of $1\times10^{-5}$ to $1\times10^{-1}$ molar and more preferably, $1\times10^{-4}$ to $1\times10^{-2}$ molar. The catalyst concentrations used are directly affected by the concentration of free ligand present, especially the excess silylalkyl phosphine ligand. In general, the higher the ligand concentration, the higher the metal level required for a certain reaction rate. In addition to the above-stated ranges, higher and lower levels of complex catalyst may be effectively employed in the process.

The amount of tertiary organo phosphine ligand used in the process can be from about 1 to 95 weight percent of the entire reaction mixture, which includes tertiary phosphine used in the silyl complex and an amount of excess phosphine. Preferably, the amount of excess ligand in the reaction mixture is from about 10 wt. percent to about 65 weight percent. Concentrations of the excess phosphine ligand can be from 0.2 to 3, preferably 0.5 to 2.7, or most preferably 0.5 to 1.5 phosphine equivalent per liter. In the case of trimethylsilylethyl diphenyl phosphine, the latter range means a weight concentration ranging from about 14 to about 47%. At an appropriate rhodium concentration, the reaction can be carried out using the excess phosphine as the solvent. However, in general, the phosphine concentration is limited to 75 weight percent of the reaction mixture. Sufficient excess phosphine concentration is used in the preferred process to carry out the reaction at the desired temperature under the desired conditions with the desired selectivity and activity maintenance. The rhodium complex concentration is then adjusted to achieve the desired reaction rate.

The mole ratio of total tertiary phosphine ligand to mole equivalent rhodium complex, L/Rh, is generally above 100, preferably being above 120, more preferably above 240, most preferably above 400. In general, higher ratios are selected when the desired operation is a continuous, rather than a batchwise operation. However, there may be instances where very low L/Rh ratios below 100 are desired and these also are encompassed within the scope of this invention.

In general, ligands of high phosphorus content are desired to achieve the required phosphine equivalency by using the minimum weight. However, to reduce the volatility of the phosphine ligands, phosphines of high molecular weight are desired. These two factors can be best compromised, for example, by using non-chelating bis-phosphine and polyphosphine ligands such as $(Ph_2PCH_2CH_2)_2Si(CH_3)_2$ and $(Ph_2PCH_2CH_2)_3SiCH_3$.

The selectivity of the present rhodium complex hydroformylation catalysts generally also depends on the molar ratio of the gaseous $H_2$ and CO reactants. To keep the partial pressure of CO desirably low, this $H_2/CO$ ratio is generally above about 1 and preferably between 2 to 100, and preferably between 2 and 20.

The present process can be suitably operated at low total process pressures. Generally desired pressures are between about 15 and 1000 psia, and and more preferably between about 55 and 500 psia.

The above pressure limitations reflect a moderate sensitivity of the rhodium complex catalyst employed to the partial pressure of CO used. Although higher values can be effectively used, the total partial pressure of CO in the feedstream is preferably less than about 400 psia more preferably less than 100 psia, and most preferably in the range of 50-1 psia. In general, when the CO partial pressure is too high and the phosphine concentration is too low, the catalyst complex can become deactivated due to the formation of carbonyl derivatives.

The partial pressure of hydrogen in general has no critical upper limit by itself from the viewpoint of hydroformylation. Preferred partial pressure of hydrogen are between about 50 and 300 psia, although higher and lower partial pressures are also operable. When the $H_2/CO$ ratio is too high and/or the CO concentration is insufficient, however, the relative rates of competing hydrogenation and isomerization reactions tend to increase.

In the upper temperature range of the present process, i.e., 130°–200° C. a significant part of the total pressure can be maintained by the addition to the olefin feedstock of either a volatile, reactive or unreactive olefin, such as butene-2, or a saturated, aliphatic hydrocarbon, such as $C_1$ to $C_{40}$ paraffinic hydrocarbon, or aromatic hydrocarbon, or by an inert gas. A preferred mode of operation incorporates a paraffinic hydrocarbon in the olefin feed and allows a facile continuous product flashoff while assuring a higher solubility of the gaseous reactants in the liquid reaction mixture. A $C_1$–$C_{12}$ and preferably, $C_1$–$C_5$, paraffin possesses higher volatility and thus is especially preferred for the hydroformylation of $C_2$ to $C_5$ olefins.

The operation of the present process can be optimized in a surprisingly broad temperature range. The range of temperature is preferably between 50° and 200° C., and preferably between 120° and 175° C. In addition, our novel catalysts are operable above 145° C. to 170° C. for the hydroformylation of $C_4$ and higher olefin.

Compared to the TPP catalyst system, the maintenance of the catalyst activity and selectivity at the highest temperatures is particularly unique. High rates of selective hydroformylation of 1-n-olefins can be realized and maintained to high conversion at 145° C. when using the present catalyst.

The present hydroformylation process can be carried out either in the liquid, vapor or in the gaseous state. A preferred process employs a liquid, more preferably homogeneous liquid, reaction phase with the present catalyst system dissolved, i.e., homogeneous catalyst.

Catalytic Intermediates in Rhodium Hydroformylation

The silyl alkyl diaryl phosphine rhodium complex catalyst compositions of the present process were previously disclosed and exemplified. From the view-point of selective hydroformylation, it is emphasized that in solution, and particularly under reaction conditions, the tris- and bis-phosphine rhodium complexes are present.

While we do not wish to be bound by the following theory, it is believed that the equilibration of tris- and bis-phosphine rhodium carbonyl hydride complexes as established via 31 P nmr studies:

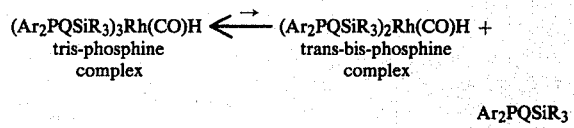

$$Ar_2PQSiR_3$$

is related to the activity and selectivity of the present catalyst according to the mechanism shown by FIG. 1.

Equilibration of the stable tris-phosphine complex to provide some of the highly reactive, coordinatively unsaturated trans-bis-phosphine is to occur in an active catalytic system. However, it is believed that in the case of stable selective catalysts, most of the rhodium is present in the stable tris-phosphine complex form.

The equilibration involves the reversible elimination and addition of a phosphine ligand. Its rate was found to depend on the temperature. As such, it was determined by 31 P nmr. It was also found that the maintenance of the equilibrium on the tris-phosphine side and the stabilization of the system, require an excess concentration of the phosphine ligand. The maintenance of the yellow color of catalyst solutions and the high selectivity of hydroformylation indicated the stability of the complex catalyst.

Figure 3:
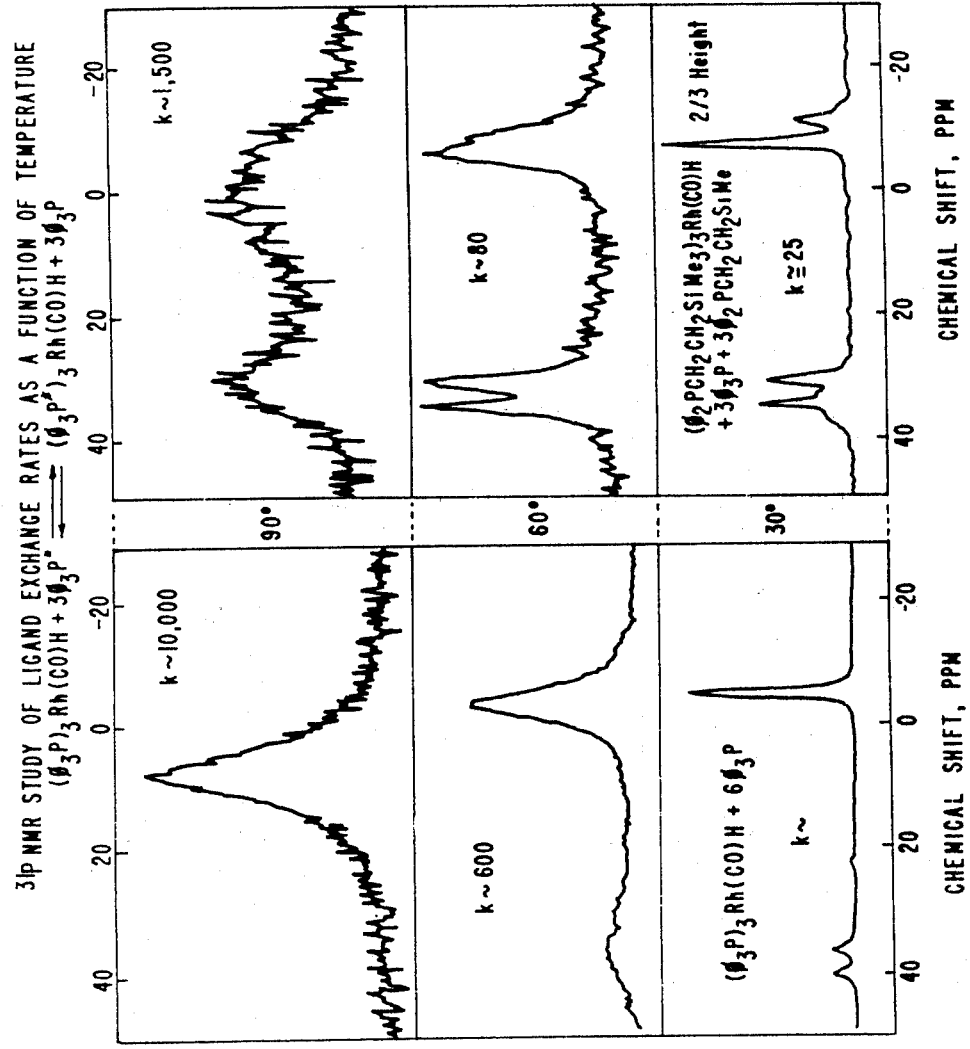
FIG. 3 illustrates by $^{31}$P nmr spectra ligand exchange rates of TPP and SEP complexes at various temperatures.

Comparative 31 P nmr studies of the known TPP catalyst plus TPP system showed that its mechanism is similar. However, the thermal activation and catalyst destabilization of this system occurs at lower temperatures (FIG. 3). On other words, the present tris(silyl diaryl phosphine) rhodium carbonyl hydride plus excess phosphine based systems are surprisingly improved high temperature catalysts.

Figure 2:
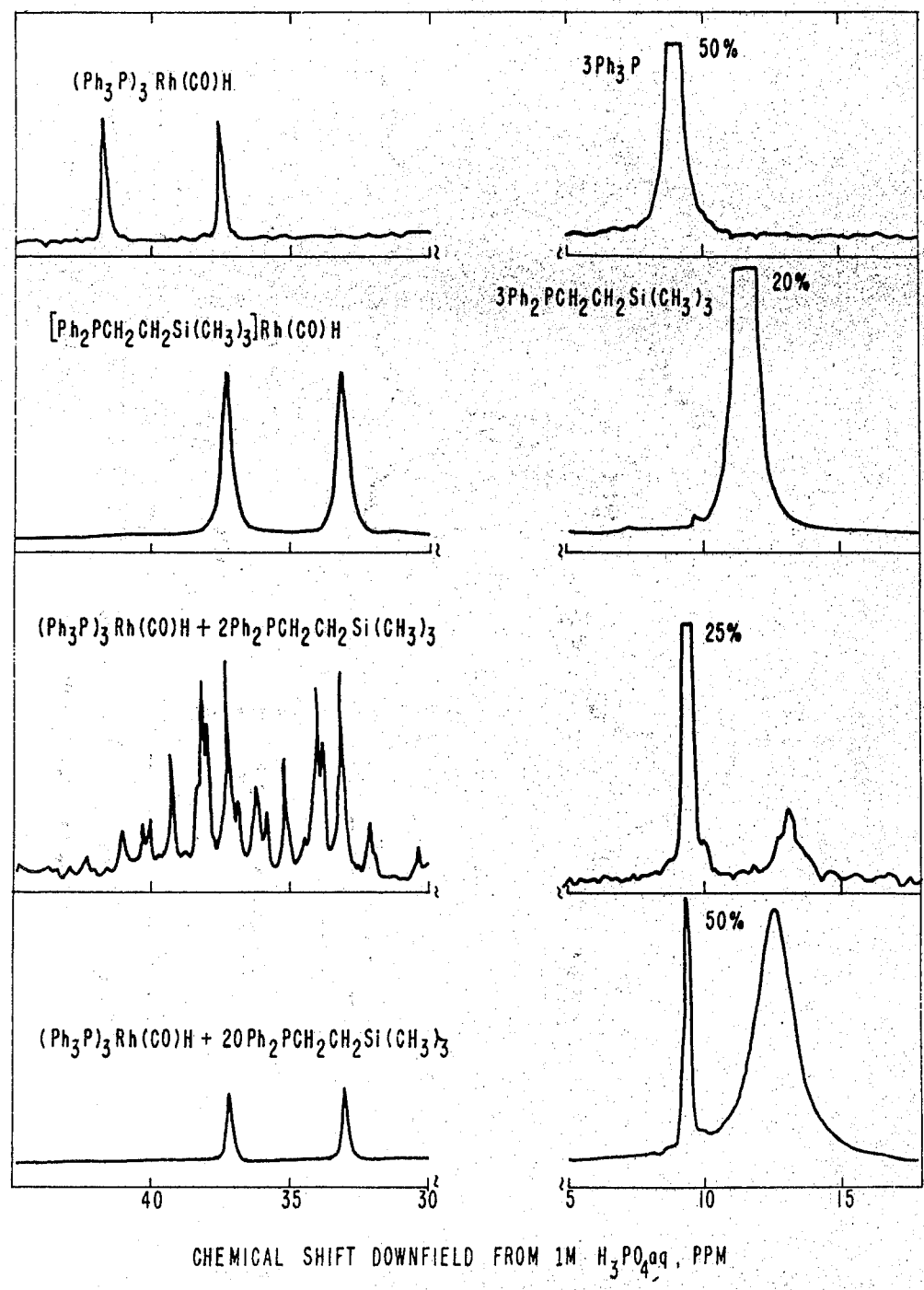
FIG. 2 shows the $^{31}$P nmr spectra of rhodium carbonyl hydride complexes formed with excess TPP (triphenylphosphine) and SEP (trimethylsilylethyldiphenylphosphine) ligands and their mixtures.

The stronger complexation of the trihydrocarbyl silyl alkyl diaryl phosphine ligands to form the corresponding tris-phosphine rhodium carbonyl hydride complexes could also be established in competitive complexation with triaryl phosphines (FIG. 2). When equimolar amounts of the two different phosphines, such as SEP and TPP were used, mostly the tris-SEP rhodium carbonyl hydride was formed. However, there were some tris-phosphine complexes containing both types of ligands. When the ratio of SEP to TPP was about 6, only the spectrum of the tris-SEP complex was observed.

When the SEP to Rh ratio was 10 or higher, even a large excess of TPP, e.g., a TPP/Rh ratio 100, would not lead to the formation of the tris-TPP complex.

The coordinatively unsaturated trans- bis-phosphine rhodium carbonyl hydride can react with both olefins and carbon monoxide in a reversible manner. Complete reaction with CO leads to the formation of nonselective catalytic intermediates, i.e., mono-phosphine dicarbonyl hydrides

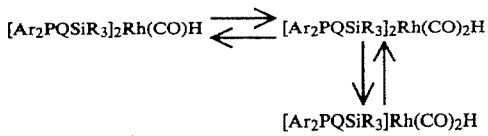

and/or irreversible catalyst deactivation (see FIG. 1).

It was found, via further 31 P nmr studies of catalyst solutions under pressure of synthesis gas of varying $H_2/CO$ ratio, that the ratio of monocarbonyl versus dicarbonyl complexes was increased by employing a high ratio of $H_2/CO$ and a high excess of the phosphine ligand. Comparative studies of the SEP versus TPP catalyst system have shown that the TPP system had a higher tendency to form the undesired dicarbonyl complexes.

The results of 31 P nmr studies of the tris-phosphine rhodium complex formation were correlated with catalyst activity. Those silylalkyl diphenyl phosphines, which do not form tris-phosphines at room temperature, are not preferred ligands for the present selective catalysis. Substitution of the α-carbon and multiple substitution of the β-carbon of the alkyl group Q in the generic branch and o-o'-substitutions of the aryl groups Ar, generally interfere with complete complexation because of steric hindrance, i.e., the desired catalyst formation.

Continuous Hydroformylation

Due to the improved thermal stability of the silyl alkyl diaryl phosphine rhodium complex catalysts, a continuous mode of operation is particularly preferred for olefin hydroformylation. When using a homogeneous liquid catalyst system, such an operation can be of a continuous plug flow type, including a step for catalyst recovery and then recirculation. A quasi continuous use of the catalyst may consist of the cyclic operation of a unit for hydroformylation and then for product flashoff. Catalyst concentration by continuous product flashoff or other methods of catalyst recovery may invole complete or partial recycle, such as "recycle flashoff process" and by this form is meant separation/isolation of products out of the reactor by means of drawing off liquid reaction mixture and conducting separation by conventional techniques, e.g., distillation under reduced pressure, generally under different process conditions, than those which are present in the reactor. However, a preferred method of operation involves continuous product flashoff, wherein the mixture of product aldehydes is continuously removed from the vapor phase of the reaction mixture.

In the present continuous product flashoff process, the aldehyde product of the hydroformylation is continuously removed as a component of a vapor mixture while the CO, $H_2$ and olefin reactants are continuously introduced. This process preferably includes the recirculation of most of the unreacted reactants in the gaseous state and the condensation and thereby removal of most of the aldehyde and aldehyde derivative products. Additional olefin, CO and $H_2$ are added as required to maintain aldehyde production and optimum process parameters. The space velocity of the gas stream is appropriately adjusted and additional gas purge is used as required to maintain production and catalyst activity. Since the rhodium complex is not volatile, no catalyst losses occur. If the phosphine ligand is volatile, additional phosphine is added occasionally to maintain its concentration in the reaction mixture.

Also, an embodiment of this invention is a process for continuous hydroformylation which comprises reacting a $C_2$ to $C_6$ olefin, preferably a 1-n-olefin and particularly preferred olefins being propylene and butene-1, with CO and $H_2$ in the presence of a tris- and bis-(silyl alkyl diaryl phosphine) rhodium carbonyl hydride catalyst as described above and in the presence of excess phosphine ligand. According to this method, reactants, preferably all the reactants, are continuously introduced into a reactor comprising dissolved catalyst and ligand in a liquid reaction mixture having preferably no added solvent and wherein at least some, preferably most, of the aldehyde products being a mixture of $C_5$ aldehydes where butene-1 is the reactant, are continuously removed in the vapor phase. It is preferred in this process to have at least some of the reagents and products recirculated. The process is carried out by having an appropriately limited partial pressure of carbon monoxide, preferably below 200 psi and appropriately high concentration of excess phosphine ligand relative to the catalyst complex, preferably above 1 weight percent, more preferably above 5 weight percent. These improvements produce and maintain an effective catalyst system of high selectivity to aldehyde products.

Specifically preferred embodiments included in the above description is wherein the process is a continuous hydroformylation process for converting butene-1 to a mixture of $C_5$ aldehyde, or converting propylene to a mixture of butyraldehydes preferably having an n/i ratio of above about 4:1, wherein said catalyst is $[(Ph_2PCH_2CH_2)_2Si(CH_3)_2]_3Rh(CO)H$, and said product aldehydes can be continuously removed from the vapor phase of said reaction mixture or recovered by recycle flashoff as described herein.

During the continuous product flashoff operation, relatively non-volatile aldehyde oligomers are formed and concentrated in the liquid reaction mixture. The oligomeric hydroxy substituted carboxylic ester condensation and redox disproportionation products formed during propylene hydroformylation were disclosed in U.S. Pat. No. 4,148,830 by Pruett and Smith. This recent patent of Pruett and Smith claims the use of aldehyde condensation products as solvents in triphenyl phosphine (TPP) rhodium complex catalyzed alpha-olefin hydroformylation. Another recent patent by Brewester and Pruett, i.e., U.S. Pat. No. 4,247,486, claims a TPP-Rh complex catalyzed continuous product flashoff process in such solvents.

In the present work, it was found that derivatives, mainly trimers, analogous to the butyraldehyde trimers, are formed during 1-butene hydroformylation from valeraldehydes. The general structure of the isomeric trimers formed during the hydroformylation of $C_3$ to $C_6$ is the following:

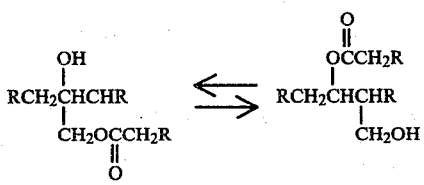

wherein R is $C_2$ to $C_5$, preferably $C_3$ alkyl.

The above aldehyde trimer is generally the main derivative and at the equilibrium conditions of the preferred continuous flashoff process, it can automatically become the main solvent component. When this occurred during 1-butene hydroformylation with the present catalysts, selectivity and production rate could be maintained and the concentration of the trimer could be limited to an equilibrium value.

In the continuous product flashoff operation, carbonylations, especially the hydroformylation of olefins is advantageously carried out at a low olefin conversion, preferably at a 20 to 80% olefin conversion. Aldehyde production rates are preferably between 0.1 to 5 g mole/liter/hour, more preferably between 0.5 and 2 g mole/liter/hour. The loss of catalyst activity is preferably less than 0.3% per day.

Operating in this manner, with optimized reactant ratios, particularly high linear to branched aldehyde product ratios are obtained from 1-n-olefins.

The continuous process can be also employed for the selective or complete conversion of different types of olefins. For example, a mixture of 1- and 2-butenes can be hydroformylated to produce mainly n-valeraldehyde and 2-butene. Similarly, a mixture of 1-butene, 2-butene and i-butene can be converted selectively to varying degrees. The olefin feedstream can also contain $C_1$–$C_{40}$ paraffinic hydrocarbons, preferably $C_1$–$C_{12}$ and more preferably $C_1$–$C_5$ paraffinic hydrocarbons.

Using the present catalyst of improved thermal stability, the application of continuous or batch flashoff processes can be extended to higher olefins lieading to non-volatile products. The preferred olefins for continuous product flashoff are of the $C_2$ to $C_6$ range and n-1-olefin type. 1-Butene is a particularly preferred reactant.

A further embodiment of the subject process is a combined isomerization-hydroformylation process wherein an internal olefin, such as butene-2, is catalytically isomerized to provide an equilibrium mixture containing a terminal olefin, i.e., butene-1, which is then preferentially hydroformylated.

Catalysts capable of performing both functions are preferably cobalt catalysts of the formula:

$$[(Ar_2PQ)_ySiR_{4-y}]_g\cdot(CoX_n)_s$$

wherein Ar, Q, y, r, G, X, n, s are as defined hereinabove.

The process can be conducted under generally the same process conditions as described in the previously referred Falbe monograph, for hydroformylation with respect to temperature, pressure, $H_2$ and CO partial pressures, catalyst and excess ligand concentrations, batch and continuous mode operations, and the like. It is particularly preferred to have temperatures between 150° and 200° C. and pressures between 500 to 2000 psia.

A preferred catalyst for use in this embodiment is $[Ph_2PCH_2CH_2Si(CH_3)_3]Co(CO)_3H$, and a preferred internal olefin reactant being butene-2, being converted to butene-1.

The following examples are illustrative of the best mode of carrying out the invention process, as contemplated by us, and should not be construed to be limitations on the scope or spirit of the instant invention.

EXAMPLE

I. Preparation of Silylalkyl Diaryl Phosphine Ligands

EXAMPLES 1–8

The silylalkyl diaryl phosphine ligand components of the present rhodium complexes were prepared during the present work.

The generally employed method for ligand preparation was the free radical chain addition of diphenyl phosphine to a vinylic compound in an anti-Markovnikov manner.

$$Ph_2PH + CH_2 + CHR \rightarrow Ph_2PCH_2CH_2R$$

As a rule, such additions were initiated in a homogeneous liquid phase by broad spectrum ultraviolet light at 15° C. The rate of addition depended strongly on the type of the olefinic compound employed. In general, compounds of vinylic substitution were highly reactive while allylic derivatives were sluggish to react. The reaction times were accordingly varied. The selectivity of the additions could be improved by using more than the equivalent amount, generally 10% excess, of the phosphine adding agent. In the case of vinylic derivatives, this reduced the oligomerization of the unsaturated component. In general, no added solvents were used. During the reaction, the conversion of reactants to products (and by-products) was followed by gas liquid chromatography (glc) and/or proton magnetic resonance spectroscopy (pmr). Usually the glc peak intensities were used to make quantitative estimates of the compositions. For identification of the product structures mainly nmr was used.

When the desired conversion was reached, the reaction mixture was usually fractionally distilled in high vacuo to obtain the pure adduct product. Most of the pure adducts were clear, colorless, liquids at room temperature. The monophosphines were mobile, the bisphosphines were viscous.

The expected structures of the isolated products were confirmed by prm. Elemental analyses were also performed to check the product compositions.

The pure phosphines were studied to determine their basicity, by potentiometric titration and indirectly by $^{31}P$ nmr. The results of direct basicity determination will be given in the overview tables, together with the other analytical characteristics of the free phosphine ligands. The $^{31}P$ nmr chemical shift values for the free ligands will be listed as comparative values when discussing the $^{31}P$ nmr of their rhodium complexes.

The phosphine basicity determinations via potentiometric titrations were performed according to the method of C. A. Streuli. For reference see Analytical Chemistry, Vol. 31, pages 1652 to 1654 in 1959 and Vol. 32, pages 985 to 987 in 1960. Half neutralization potentials (HNP's) of the phosphines were determined using perchloric acid as a titrant and pure nitromethane, free from weakly basic impurities, as a solvent. The values obtained were subtracted from the HNP of a stronger organic base, diphenyl-guanidine, which served as a daily standard reference. The resulting ΔHNP values of the phosphines are indirectly related to their basicity. In case of phosphines, which were also studied by Streuli, somewhat different ΔHNP values were obtained in the present work. Since ion exchange resin purified nitromethane was used in the present work, the reported values should be more correct.

A number of trihydrocarbylsilylethyl and -propyl diphenyl silanes were prepared by adding dipenyl phosphine to the corresponding vinylic or allylic silane. The preparation, physical properties and analytical composition of seven compounds are summarized in Table I. The table also shows the basicity characteristics of the products as characterized by their ΔHNP values. It is noted that all the trihydrocarbylsilylalkyl diphenyl phosphines are much stronger bases than triphenyl phosphine ($Ph_3P$: ΔHNP=510).

EXAMPLE 2

Tripropylsilylethyl Diphenyl Phosphine

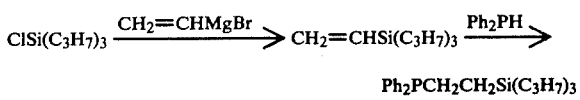

$$Ph_2PCH_2CH_2Si(C_3H_7)_3$$

To prepare the vinyl tripropyl silane reactant, chloro tri-n-propyl silane was reacted with vinyl magnesium bromide in refluxing tetrahydrofuran.

After removing the THF solvent by distillation, the residual product was taken up in ether, then washed with ice water and then with 5% aqueous sodium hydrogen carbonate. The ether solution was then dried over anhydrous sodium sulfate and distilled to obtain

TABLE I

Preparation, Physical Properties and Composition of Silyl Substituted Alkyl Diphenyl Phosphine Ligands

| Example No. | Structure of Ligand | Unsaturated Reactant Used | Ligand Bp, °C./mm (Mp., °C.) | Distd. Yield ~% | Elemental Composition, % Calcd. C | H | P | Found C | H | P | Inverse Basicity, Δ HNP |
|---|---|---|---|---|---|---|---|---|---|---|---|
| 1 | $Ph_2PCH_2CH_2Si(CH_3)_3$ | $CH_2=CHSi(CH_3)_3$[a] | 115-118/0.075 | 81 | 71.29 | 8.09 | 10.81 | 71.98 | 8.12 | 10.59 | 385 |
| 2 | $Ph_2PCH_2CH_2Si(C_3H_7)_3$ | $CH_2=CHSi(C_3H_7)_3$[b] | 155-156/0.10 | 63 | 74.54 | 9.52 | 8.36 | 74.35 | 9.23 | 8.37 | 385 |
| 3 | $Ph_2PCH_2CH_2SiPh_3$ | $CH_2=CHSiPh_3$[c] | (128-131[d]) | — | 81.32 | 6.19 | 6.55 | 80.97 | 6.18 | 6.71 | 413 |
| 4 | $(Ph_2PCH_2CH_2)_2Si(CH_3)_2$ | $(CH_2=CH)_2Si(CH_3)_2$[a] | 238-239/0.20 | 84 | 74.35 | 7.07 | 12.78 | 73.65 | 6.90 | 12.59 | 434 |
| 5 | $Ph_2PCH_2CH_2CH_2Si(CH_3)_3$ | $CH_2=CHCH_2Si(CH_3)_3$[a] | 150/0.10 | 50 | 71.96 | 8.38 | 10.31 | 72.27 | 8.29 | 10.25 | 408 |
| 6 | $Ph_2PCH_2Si(CH_3)_3$ | $[ClCH_2Si(CH_3)_3]$[e] | 129-130/0.2 | 86 | 70.55 | 7.77 | 11.37 | 70.01 | 7.64 | 11.36 | 404 |
| 7 | $(Ph_2PCH_2CH_2CH_2)_2Si(CH_3)_2$ | $(CH_2=CHCH_2)_2Si(CH_3$[a]$)_2$ | 248-250/0.1 | 48 | 74.97 | 7.45 | 12.08 | 74.96 | 7.45 | 12.00 | 420 |

[a]The reactant was a purchased chemical reagent.
[b]The reactant was prepared from tripropyl chloro silane by reacting it with vinyl magnesium bromide.
[c]The reactant was prepared from vinyl trichloro silane by reacting it with the appropriate Grignard reagent.
[d]The product was recrystallized from cyclohexane-toluene.
[e]The product was prepared from chloromethyl trimethyl silane by reacting it with lithium diphenyl phosphide.
[f]Relative half neutralization potential compared to that of diphenyl guanidine.

Accounts of the individual experiments are given in the following.

EXAMPLE 1

Trimethylsilylethyl Diphenyl Phosphine

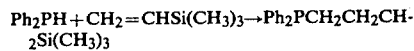

A magnetically stirred mixture of 46.5 g (0.25 mole) diphenyl phosphine and 25 g (0.25 mole) of vinyl trimethyl silane, in a closed cylindrical quartz tube, was irradiated from about 3 cm distance with two 75 Watt Hanau tube immersion lamps, with a wide spectrum of ultraviolet irradiation, in a 15° C. water bath for 26 hours. A proton magnetic resonance spectrum of a sample of the resulting mixture exhibited no significant peaks in the vinyl region indicating a substantially complete addition.

The reaction mixture was distilled in vacuo to obtain 61 g (81%) of the desired trimethylsilylethyl diphenyl phosphine adduct, as a clear colorless liquid, having a boiling range of 109°-110° at 0.1 mm (Table I).

The selectivity to provide the desired adduct was increased when the diphenyl phosphine reactant was employed in a 10 mole % excess.

vinyl tripropyl silane, bp. 75°-77° C. at 11 mm.

The vinyl tripropyl silane was then reacted with diphenyl phosphine with u.v. initiation for 86 hours in a manner described in the previous example. The conversion was about 95%. The mixture was fractionally distilled to yield the pure product as a clear, colorless, mobile liquid (see Table I.)

EXAMPLE 3

Triphenylsilylethyl Diphenyl Phosphine

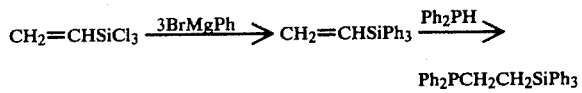

$$Ph_2PCH_2CH_2SiPh_3$$

To obtain the vinyl triphenyl silane intermediate, vinyl trichloro silane was reacted with phenyl magnesium bromide in an ether-THF solvent mixture. The resulting product was worked up in a manner described in the previous example. The product was a low melting solid which could be distilled in vacuo using a hot condenser. At room temperature, the distillate solidified to yield a white crystalline compound, mp. 60°-65° C. Pmr confirmed the expected vinyl triphenyl silane structure.

Anal. Calcd. for $C_{20}H_{18}Si$: C, 83.86; H, 6.33. Found: C, 83.92; H, 6.34.

The vinyl triphenyl silane was reacted with 10% excess of diphenyl phosphine. To maintain a homogeneous reaction mixture, a temperature of 80° C. and cyclohexane solvent were employed. After the usual u.v. initiated addition, the reaction mixture was allowed to cool to room temperature. This resulted in the crystallization of the triphenylsilylethyl diphenyl phosphine adduct. To obtain it in a pure form, the adduct was filtered and recrystallized from a four to one mixture of cyclohexane and toluene. A white crystalline product having the properties shown in Table I was obtained.

EXAMPLE 4

Bis-(Diphenylphosphinoethyl) Dimethyl Silane

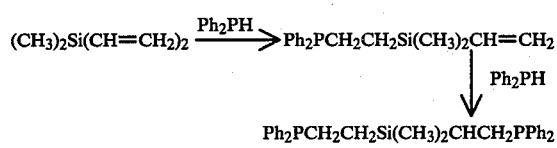

A mixture of 9.0 g (0.8 mole) dimethyl divinyl silane and 32.7 g (0.176) diphenyl phosphine (10% excess over equivalent amounts) was reacted for 22 hours in the manner described in Example 1. The reaction mixture was fractionated in vacuo to obtain minor amounts of a clear, colorless, slightly viscous liquid monoadduct, and major amounts of a clear, colorless, highly viscous liquid diadduct, i.e., the desired bis-(diphenylphosphinoethyl) dimethyl silane (Table I). The latter solidified to a crystalline solid on standing and was readily recrystallized from hexane.

EXAMPLE 5

Trimethylsilypropyl Diphenyl Phosphine

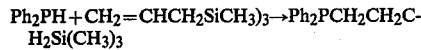

A mixture of 22.8 g (0.2 mole) allyl trimethyl silane and 27.2 g (0.2 mole) diphenyl phosphine was reacted for 158 hours in the manner described in Example 1. A subsequent fractional distillation, yielded the desired pure adduct as a clear, colorless liquid (Table 1).

EXAMPLE 6

Trimethylsilylmethyl Diphenyl Phosphine

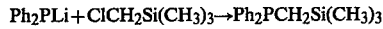

The known but unavailable trimethylsilylmethyl diphenyl phosphine was derived via reacting chloromethyl trimethyl silane with lithium diphenyl phosphide in an ether-hexane mixture. After removing the lithium chloride by-product by filtration, the product was isolated as a clear, colorless liquid by fractional distillation in vacuo (Table 1).

EXAMPLE 7

Bis-(Diphenylphosphinopropyl) Dimethyl Silane

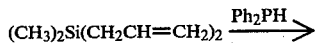

-continued

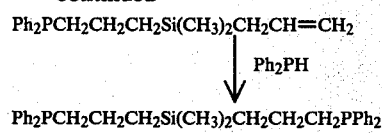

A mixture of 70 g (0.5 mole) dimethyl diallyl silane and 204.6 g (1.1 m mole, 10% excess over equivalent amounts) of diphenyl phosphine was reacted in the manner described in Example 1 at 40° C. The addition was slow. After 24 hours, only about 10% of the diphenyl phosphine reacted. The irradiation of the reaction mixture was continued for a total of 160 hours. A subsequent fractional distillation provided 46 g of monoadduct, as a clear, slightly viscous liquid monoadduct of bp. 122°–134° C. at 0.05 mm and 113 g of the desired diadduct (Table 1) as a clear, light yellow, viscous liquid.

Anal. Monoadduct $C_{20}H_{27}PSi$. Calcd.: C, 73.57; H, 8.34, P, 9.59. Found: C, 73.79; H, 8.26; P, 9.66.

EXAMPLE 8

Bis-(Diphenylphosphinoethyl) Diphenyl silane

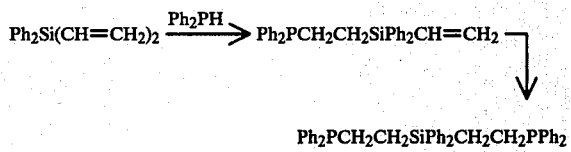

About 2 moles of diphenyl phosphine were added sequentially to one mole of divinyl diphenyl silane to yield mostly the desired diadduct which crystallized on standing; recrystallization from heptane provided the pure product.

EXAMPLE 9

Tris-(Diphenylphosphinoethyl) Methyl Silane

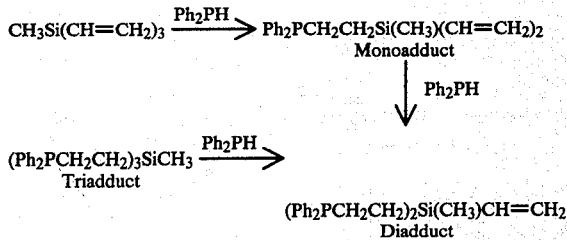

A mixture of 37.3 g (0.3 mole) trivinyl methyl silane and 175.8 g (0.945 mole) diphenyl phosphine was reacted at 95° C. with u.v. light initiation in quartz pressure tube, in the manner described in Example 1, until about 50% of the diphenyl phosphine was converted. A subsequent distillation of the resulting reaction mixture in vacuo under nitrogen resulted in the isolation of the expected adducts.

The monoadduct (29 g) was obtained as a clear, colorless mobile liquid of about bp. 132° C. at 0.05 mm. The diadduct (51 g) was a slightly hazy, colorless viscous liquid at room temperature. It distilled at about 240° C. at 0.05 mm. The distillation residue (50 g, 24.5%) mostly consisted of the triadduct.

In another experiment, the reaction mixture was further irradiated until most of the diphenyl phosphine has reacted. The excess diphenyl phosphine (14.5 g) was then recovered from the reaction mixture by vacuum stripping at 220° C. For recrystallization, the residual product was dissolved in a 3 to 2 mixture of hot toluene and methanol to obtain a 28% solution. On cooling to −30° C., the desired triadduct crystallized and was isolated by filtration with suction and washed with methanol. The dry product weighed 160 g (78%) and melted between 98° and 101° C. A proton nmr spectrum of the product supported the assumed tris-(diphenylphosphinoethyl) methyl silane structure.

EXAMPLE 10

Tetrakis-Diphenylphosphinoethyl) Silane $$Si(CH=CH_2)_4 + 4Ph_2PH \rightarrow Si(CH_2CH_2PPh_2)_4$$

A mixture of 27.2 g (0.2 mole) of tetravinyl silane and 149.5 g (0.804 mole) diphenylphosphine was reacted in a quartz pressure tube at 200° C. with u.v. light initiation until most of the diphenyl phosphine was converted. The hot, molten reaction mixture was added to 720 g of hot toluene with stirring. The tetraadduct product precipitated from the solution as a white crystalline solid. The mixture was allowed to cool to ambient temperature and then filtered with suction. After washing with toluene and drying in vacuo, 84 g (47.7%) of crude product was obtained. This was recrystallized from 1200 ml of xylene to obtain 69 g of the pure tetrakis(diphenylphosphinoethyl) silane of mp. 198°–199° C.

Anal. Calcd. for $C_{56}H_{56}SiP_4$: C, 76.34; H, 6.41; P, 14.06. Found: C, 76.44; H, 6.38; P, 13.71.

Similar additions are carried out using di-4-tolyl phosphine and di-4-fluorophenyl phosphine and the above unsaturated reactants to yield the corresponding ring substituted products.

II. Preparation of Tris(Silylalkyl Diaryl Phosphine) Rhodium Carbonyl Hydride Complexes (Examples 11 to 32)

A. Preparation from Rhodium Chloride

EXAMPLE 11

Tris-(Trimethylsilylethyl Diphenyl Phosphine) Rhodium Carbonyl Hydride $$3Ph_2PCH_2CH_2Si(CH_3)_3 + RhCl_3.3-H_2O \rightarrow [Ph_2PCH_2CH_2Si(CH_3)_3]_3Rh(CO)H$$

To a vigorously stirred, refluxing, nitrogenated solution of 11.4 g (40 mmole) of tris-(trimethylsilylethyl) diphenyl phosphine of Example 1 in 400 ml of ethanol, a hot solution of 1.04 g (0.4 mmole) of rhodium trichloride trihydrate in 80 ml ethanol was added at once. After a delay of 15 seconds, 40 ml warm aqueous (37%) formaldehyde solution and, immediately thereafter, 80 ml hot ethanolic solution of 3.2 g of potassium hydroxide were added. The resulting clear orange liquid reaction mixture was refluxed for 10 minutes. During the heating, the color changed to deep orange.

The mixture was cooled to −25° C. to crystallize the complex product. Crystallization started at −10° C. and was completed on standing for about 2 hours at −25° C. The crystalline complex was separated by filtration through a precooled Buechner funnel with suction and washing successively with 20 ml cold portions of ethanol, water, ethanol and n-hexane. The complex was then dried in the presence of anhydrous calcium chloride at 0.1 mm over the weekend. As a result, 2.2 g (2.2 mole, 55%) of dry tri-(trimethylsilylethyl diphenyl phosphine) rhodium carbonyl hydride complex was obtained as a fine crystalline orange-yellow powder. In a sealed capillary tube, the complex melted between 126°–129° C. to a clear dark red liquid. In an open capillary, complete melting occurred at 121° C. There was no sign of decomposition on heating up to 140° C. in either case.

The infrared spectrum of the complex in Nujol showed a strong carbonyl band of 1985 cm$^{-1}$ and a band of medium intensity at 1900 cm$^{-1}$.

Analyses Calcd. for $C_{52}H_{70}OP_3RhSi$: C, 63.01; H, 7.12; P, 9.38; Found: C, 62.89; H. 7.06; P, 9.59.

B. Preparation from Tris-(Triphenyl Phosphine) Rhodium Carbonyl Hydride Via Ligand Displacement (Examples 10–19).

EXAMPLES 12–22

Tris-(Silylalkyl Diphenyl Phosphine) Rhodium Carbonyl Hydrides $(Ph_3P)_3Rh(CO)H + 3Ph_2P(CH_2)_mSiR_3 \longrightarrow$ $(Ph_2P(CH_2)_nSiR_3)_3.Rh(CO)H + 3Ph_3P$ $(Ph_3P)_3Rh(CO)H + 3[Ph_2P(CH_2)_m]_2SiR_2 \longrightarrow$ $[Ph_2P(CH_2)_mSiR_2(CH_2)_nPPh_2]_3Rh(CO)H + 3Ph_3P$ The tris-(alkyl diaryl phosphine) rhodium carbonyl hydride complexes were prepared by reacting commercially available tris-(triphenyl phosphine) rhodium carbonyl hydride (from Engelhard Minerals and Chemicals Corporation, Newark, N.J.) with the corresponding alkyl diaryl phosphines. Generally, the reactions were performed in a 90 to 10 mixture of toluene and deuterated benzene as a solvent under a nitrogen blanket. The deuterated benzene component was used as a primary nmr standard.

At first, an about 5% solution of the alkyl diaryl phosphine reactant was prepared. To samples of the solution, TPP rhodium carbonyl hydride was added in equivalent and half equivalent amounts. The resulting mixtures were magnetically stirred until homogeneous liquids were obtained. Additional amounts of the toluene solvent were used if needed. The homogeneous reaction mixture was then studied by $^{31}P$ nmr spectroscopy. Chemical shifts were measured by assigning a shift of 0 ppm to the frequency at which 1M $H_3PO_4$ would resonate.

The $^{31}P$ NMR experiments were carried out using a JEOL FX 90Q multinuclear nmr spectrometer. When required, the experiemental conditions were adjusted, i.e., the $^1H$-$^{31}P$ decoupling was removed and longer delays between pulses were employed, to determine the relative populations of free and rhodium bound alkyl diphenyl phosphine and TPP.

In general, three and six moles of a silylalkyl diphenyl phosphine were used per mole of tris TPP rhodium carbonyl hydride. $^{31}P$ NMR spectroscopy of the resulting solutions showed that the added ligand displaced the TPP. The doublet signal of the bound TPP essentially disappeared and the singlet signal of free TPP appeared instead. In the mixtures having 3 moles of the added silylalkyl phosphine, most of the added ligand was bound and as such exhibited a doublet signal upfield from that of bound TPP. Although the doublet of the silylalkyl diphenyl phosphine complexes have chemical shift values different from that of TPP, the coupling constants are about the same for both types of complexes. The coupling constant and chemical shift difference between bound and free ligand indicates that both types of ligands form tris-phosphine rhodium carbonyl hydrides. Finally, it was noted that the mixture having six moles of added alkyl diphenyl phosphine ligand had about equal amounts of free and bound ligand plus the originally bound TPP as additional free ligand.

The nmr parameters of the trihydrocarbylsilylalkyl diphenyl phosphine complexes are shown by Table II (Examples 11–19). The most characteristic parameter is the chemical shift value of the rhodium complexed ligand. For comparison, the chemical shift values of the free ligands are also tabulated. Complexation by rhodium of the phosphine apparently produced a similar

Example 23

Mixed Tris-Phosphine Rhodium Carbonyl Hydride Complex Species in TPP and/or SEP Based Catalyst Systems

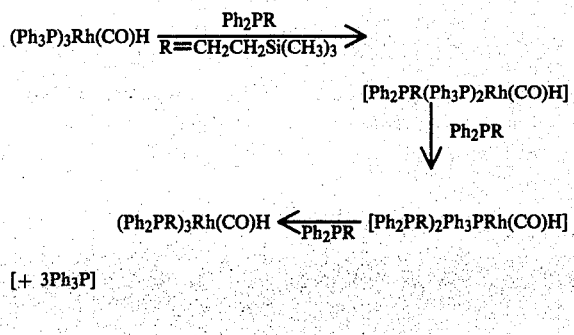

TABLE II $^{31}P$ Nuclear Magnetic Resonance Parameters of Free and Rhodium-Complexed Trihydrocarbylsilylalkyl Diphenyl Phosphines

| Example No. of Complex | Example No. of Ligand | Chemical Structure of Complex | Chemical Shift δ, ppm Free Ligand | Chemical Shift δ, ppm Complexed Ligand | Coupling Constant, P—Rh Complexed Ligand | Chemical Shift δ, ppm Phosphine Oxide | Chemical Shift Difference Δδ, ppm Complex Ligand |
|---|---|---|---|---|---|---|---|
| — | — | $(Ph_3P)_3Rh(CO)H$(Reference) | −7.5 | +38.3 | 155 | | 45.8 |
| 13 | 1 | $[Ph_2PCH_2CH_2Si(CH_3)_3]_3Rh(CO)H$ | −12.2 | +34.6 | 150 | +27.0 | 46.7 |
| 14 | 2 | $[Ph_2PCH_2CH_2Si(C_3H_7)_3]_3Rh(CO)H$ | −11.2 | +34.8 | 151 | +29.9 | 46.0 |
| 15 | 3 | $(Ph_2PCH_2CH_2SiPh_3)_3Rh(CO)H$ | −10.6 | +35.5 | 151 | +21.1 | 46.1 |
| 16 | 4 | $[(Ph_2PCH_2CH_2)_2Si(CH_3)_2]_3[Rh(CO)H]$ | −12.2 | +35.1 | 150 | +27.2 | 47.3 |
| 17 | 5 | $[Ph_2PCH_2CH_2CH_2Si(CH_3)_3]_3Rh(CO)H$ | −19.7 | +26.6 | 154 | +24.6 | 46.3 |
| 18 | 6 | $(Ph_2PCH_2Si(CH_3)_3]_3Rh(CO)H$ | −24.4 | +17.0 | 133$^a$ | +23.9 | 41.4 |
| 19 | 7 | $[(Ph_2PCH_2CH_2CH_2)_2Si(CH_3)_2]_3Rh(CO)H$ | 19.5 | 26.5 | 156 | | 46.2 |
| 20 | 8 | $[(Ph_2PCH_2CH_2)_2SiPh_2]_3Rh(CO)H$ | −11.6 | 35.3 | 151 | 27.2 | 46.9 |

$^a$The $^{31}P$—$^{103}Rh$ coupling was not resolved at room temperature but was clearly resolved at −60° C.

downfield change of the shift values. Finally, it is also noted in reference to the table, that even the limited exposure of the rhodium complexed phosphines to air resulted in some oxidation to the corresponding phosphine oxides. The latter exhibited sharp singlets slightly upfield from the complexed phosphine, in general.

The data of Table II show that, with the exception of the sixth compound all the phosphine ligands form similar, well characterizable complexes at room temperature. The line shapes of the signals showed little but varying broadening, i.e., ligand exchange.

The $^{31}P$ nmr parameters were similarly determined for the rhodium complexes of triethylsilylethyl diphenyl phosphine, tris-(diphenylphosphinoethyl) methyl silane and tetrakis-(diphenylphosphinoethyl) silane. The monophosphine complex exhibited a simple doublet of σ34.7 ppm and J P-Rh of 151 cps. The tris-phosphine complex showed a more complex signal of what appeared to be two doublets having chemical shifts of 35.3 and 36.8 ppm and identical coupling constants of 154 cps. Finally, the tetraphosphine complex gave an even more complex signal, apparently consisting of three doublets, having the following chemical shift values and coupling constants: 37.6 (154); 37.0 (151) and 35.9 (149) [Examples 21 and 22].

As it is illustrated by the above reaction scheme, the displacement of the triaryl phosphine ligands from their tris-phosphine rhodium carbonyl hydride complexes in a stepwise reaction. The scheme indicates that 2 "mixed phosphine complexes" are intermediates in such displacements. Each of these complexes should exhibit two doublet $^{31}P$ nmr peaks with further P-P splitting.

Starting with the tris-TPP complex, experiments were carried out with varying amounts of the SEP ligand to determine what ranges of SEP/TPP ratios will result in major amounts of mixed complexes. These studies were carried out in the manner described in the previous example. However, to slow down ligand exchange they were carried out at −60° C. This should improve the detection of minor complex species. The results are illustrated by FIG. 2.

For reference, FIG. 2 shows the $^{31}P$ nmr spectra of the TPP and SEP complexes in the presence of a three-fold molar excess of TPP and SEP, respectively. These spectra are to be compared with that of two mixtures containing a low and a high ratio of SEP to TPP.

The first mixture contained 2 moles of SEP and 3 moles of TPP per rhodium. Its spectrum has shown that, nevertheless, the tris-SEP complex was a primary component. There are four other major doublets in the complex spectrum of this mixture. These are apparently due to the two mixed phosphine complexes. It is interesting to observe that there are no significant amounts of the TPP complex present. Accordingly, there are major amounts of the free TPP and minor amounts of the free SEP ligand. As it is indicated by the line broadening of the free SEP peak, the ligand undergoes a fast ligand exchange with the mixed complexes, even at −60°, i.e., faster than TPP.

The second mixture contained 60 moles of SEP ligand per 30 moles of TPP and one atom of Rh. This means a SEP to TPP ratio of 20. At this high ratio, only the doublet signal of the tris-SEP complex is exhibited. All the triphenyl phosphine shows up as being free. Its extremely narrow peak indicates that there is essentially no participation by TPP in the ligand exchange process.

system is the result of equilibrating the TPP complex with trimethylsilylethyl diphenyl phosphine (SEP):

Example 24

Comparative Rates of the Formation of bis-TPP and bis-SEP Rhodium Carbonyl Hydrides Via the Thermal Dissociation of Their Respective Tris-Phosphine Complexes In the case of the tris-(trimethylsilylethyl diphenyl phosphine), tris-SEP, rhodium carbonyl hydride complex, there was moderately slow ligand exchange between free and complexed phosphines as indicated by the broadening of the $^{31}$nmr signals. The exchange mechanism is illustrated for the SEP complex by the following:

SEP being a substituted alkyl diphenyl phosphine, was found to be a stronger complexing agent than TPP. The spectra of both systems were taken under comparative conditions at 30°, 60° and 90° C.

The line shapes of the signals of the 30° spectra showed little signal broadening in both cases. This indicated comparably slow exchange rates of about 25 per second. In alternative terms, relatively long average exchange lifetimes, in the order of $2 \times 10^{-2}$ sec, were indicated for both triphosphine complexes. At 60°, considerable line broadening occurred, indicating a much faster exchange. The exchange acceleration was greater in the case of the TPP system (k=600 vs. 80 sec$^{-1}$). The average lifetime was about $3 \times 10^{-3}$ sec for the TPP system and $6 \times 10^{-3}$ sec for the SEP system. At 90°, only a single, broad signal could be observed for the TPP system while the SEP system still exhibited separate, although extremely broad, chemical shift ranges for the complexes and free phosphorus species.

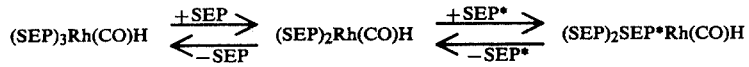

as indicated by this mechanism the exchange rates are directly related to the rate of the dissociation of the tris-phosphine complex.

The line shapes of signals for the SEP complex and the known TPP complex are compared by FIG. 3 at various temperatures. At first, the 30° C. spectra will be discussed. These spectra indicate that at 30° C., there is a similar, ligand exchange rate between the new SEP and the known TPP complex.

The tris-SEP complex and most of the other trihydrocarbylsilylethyl diphenyl phosphine complexes showed a very similar ligand exchange behavior at 30° C. The tripropylsilylethyl diphenyl phosphine complex (Example 12) exhibited a definitely slower exchange rate. The exchange rate of the triphenylsilylethyl diphenyl phosphine complex (Example 13) was even much slower than that. It appeared that substituted alkyl diphenyl phosphine ligands of increasing bulkiness had decreasing ligand exchange rates. In both cases though, the TPP ligand exchanged less rapidly than the alkyl diphenyl phosphine.

Finally, it is noted that when even a moderately bulky alkyl substitutent was too close to the phosphorus, i.e., in the case of trimethylsilylmethyl diphenyl phosphine, the complexation of phosphorus to the rhodium was inhibited. In that case, there was no distinct complex formation with the sterically hindered ligand at 30° C. At −60° C., a stable complex was formed. However, this complex was decomposed when its solution was heated under hydroformylation process conditions.

As far as ligand exchange rates at higher temperature are concerned, the results shown by FIG. 3 are typical. FIG. 3 shows the comparison of two systems: tris-triphenyl phosphine rhodium carbonyl hydride plus triphenyl phosphine and tris-trimethylsilylethyl diphenyl phosphine plus triphenyl phosphine. The latter Apparently, the exchange acceleration in the case of the PP system was tremendous. The average lifetime between exchanges was reduced by about two orders of magnitude to $5 \times 10^{-5}$ sec (k=10,000 sec$^{-1}$). In the case of the SEP system, the average lifetime dropped by about one order to $5 \times 10^{-4}$ sec (k=1,500 sec$^{-1}$). It must be emphasized that the exchange rates and lifetimes reported here may change somewhat when the lineshape is subjected to a rigorous computer analysis. The relative order of their values will remain unaltered, however.

It is interesting to note that there was no great change of equilibria with the increasing exchange rates. Apparently, both ligand elimination and addition increase similarly in this temperature range. The tris-phosphine rhodium species remained the dominant form of complexes. In the SEP complex plus free TPP system, the rhodium remained predominantly complexed to the SEP.

The role of excess phosphine ligand is apparently to maintain the equilibria in favor of the tris-phosphine complex, i.e. to reduce both the concentration and average lifetime of the unstable and highly reactive bisphosphine complex. The increased ligand exchange rate provides enough active bis-phosphine complex catalytic species for fast hydroformylation, without leading to noncatalytic side reactions, i.e., catalyst decomposition.

In summary, the above and similar ligand exchange rate studies indicate that, in the presence of excess ligand, the silyl alkyl diaryl phosphine rhodium complexes are catalytically activated at higher temperatures than the known triaryl phosphine rhodium complexes. Less ligand exchange at comparable temperature also meant a higher temperature for the irreversible thermal dissociation, i.e., decomposition of the catalyst complex.

C. Preparation from Dicarbonyl Acetylacetonato Rhodium Via Ligand Displacement and Hydrogenation For the isolation of pure complexes, one usually starts with an about 0.8% ethanolic solution of the dicarbonyl acetonato rhodium starting compound. Then a threefold molar excess of the phosphine ligand in slight excess is added to provide a solution of the intermediate complex. This is then reduced by hydrogen. The complex is usually formed as a precipitate.

Example 25

Tris-(Trimethylsilylethyl Diphenyl Phosphine) Rhodium Carbonyl Hydride $$3Ph_2PCH_2CH_2Si(CH_3)_3 + Acac^-Rh^+(CO)_2 + H_2 \longrightarrow$$

$$[Ph_2PCH_2CH_2Si(CH_3)_3]_3Rh(CO)H + AcacH$$

To a magnetically stirred solution of 0.258 g (0.01 mole) dicarbonyl acetylacetonato rhodium in ethanol, 0.887 g (0.0031 mole) of trimethylsilylethyl diphenyl phosphine was added under nitrogen. Instantaneous displacement of one of the carbonyl ligands was indicated by the evolution of CO gas. The resulting dark orange solution of the intermediate was transferred to a glass pressure tube equipped with a Teflon screw valve and a magnetic stirrer, for hydrogenation.

The reaction tube was evacuated until the solvent started to boil. Then it was filled and pressured with hydrogen to a pressure of about 2 Atm.

On stirring the reaction mixture, rapid hydrogenation occurred. The color of the solution started to become lighter. After an hour, yellow crystalline solids started to precipitate. The reaction mixture was stirred overnight under hydrogen pressure to complete the reduction. The hydrogen was then released and the mixture was filtered with suction under nitrogen. A light orange filtrate and yellow crystals were obtained.

The crystals were washed twice with 2 ml portions of ethanol and dried under a pressure of 0.1 mm and at room temperature. The resulting pure tris-SEP rhodium carbonyl hydride was 0.65 g, i.e., about 65% of the theoretical yield. Its solid state $^{31}P$ nmr spectrum supported the expected structure.

The $^{31}P$ nmr spectrum of the combined filtrates showed that essentially all the phosphorus was in the form of the same tris-SEP complex. This indicated that the reaction was quantitative.

The tris-SEP complex was also formed in aromatic hydrocarbon and aldehyde solvents. Hydrogen could be effectively used for reduction at atmospheric pressure. The reaction was complete within a few hours in aromatic hydrocarbons.

EXAMPLES 26–30

Other Tris-(Silyalkyl Diphenyl Phosphine) Rhodium Carbonyl Hydrides

In a manner similar to the SEP complex preparation described in the previous example, analogous complexes of other silylalkyl diphenyl phosphines were obtained. The trimethylsilylpropyl diphenyl phosphine complex formed a crystalline precipitate. The two bis(-diphenyl phosphinoalkyl) silane complexes were oily. The tripropylsilylethyl and triphenylsilylethyl diphenyl phosphine complexes remained in solution when this procedure was used. On removing the ethanol in vacuo, oily complexes were obtained.

EXAMPLE 31

Mixed Tris-Phosphine Rhodium Carbonyl Hydride Complex Species in Octyl Diphenyl Phosphine and SEP Based Catalyst Systems Complex equilibria can be studied by $^{31}P$ nmr between different alkyl diaryl phosphine complexes via the hydrogenation of their mixtures with dicarbonyl acetylacetonato rhodium. Typically, 3 moles of each of two phosphine ligands are used per mole dicarbonyl acetylacetonato rhodium. The rhodium reactant is used in amounts corresponding to 2 weight percent of the solvent, typically a 9/1 mixture of toluene and deuterobenzene. The phosphine reactants are then added to prepare a solution of the intermediate. This solution is then placed into a pressure tube equipped with a Teflon valve. This tube, properly shaped and fitted doubles as a reactor and an nmr sample container. It is pressured by hydrogen to 30 psi, i.e., about 2 atm. Then it is shaken, usually overnight. This results in the formation of tris-phosphine rhodium carbonyl hydride complexes plus 3 moles of free phosphine. If the binding strength of the two phosphines is equal, a statistical distribution results between the four potential complexes as indicated:

$$3Ph_2PR + 3Ph_2PR' + AcacRh(CO)_2$$
$$\downarrow H_2$$
$$(Ph_2PR)_3Rh(CO)H + (Ph_2PR')_3Rh(CO)H +$$
$$12.5\% \qquad 12.5\%$$
$$(Ph_2PR)_2Ph_2PR'Rh(CO)H + Ph_2PR(Ph_2PR')_2Rh(CO)H +$$
$$12.5\% \qquad 12.5\%$$
$$Ph_2PR + Ph_2PR'$$
$$25\% \qquad 25\%$$

Such a distribution was the approximate result of the competition between the SEP ligand $[R=(CH_3)_3SiCH_2CH_2]$ and n-octyl diphenyl phosphine $[R=CH_2(CH_7)]$. The signals of the two free ligands were of equal intensity. The relative amounts of the free phosphine ligands are usually in a simple indirect relationship to the strength of complexation with the rhodium.

EXAMPLE 32

Tris-t-Phosphine Rhodium Carbonyl Hydride Equilibria at High P/Rh Ratios Among SEP and Ar₃P Complexes Using the $^{31}P$ nmr technique of the previous example, equilibria among tris-SEP rhodium carbonyl hydride and complexes including one or more triaryl phosphine ligands were also studied at high P/Rh ratios. Rh to SEP to Ar₃P ratios of 1:20:80 were used in the absence of added solvent with TPP and 4-chlorophenyl diphenyl phosphine (Cl-TPP) as the Ar₃P ligand. Cl-TPP was employed because of its relatively low mp. (45° C.).

The results of these variable temperature experiments showed that, due to the fairly high SEP/Rh ratio, complexes containing SEP predominated, even though the Ar₃P/Rh ratio was much higher. Substituted triaryl phosphine components were preferred because of their generally higher solubility.

EXAMPLE 33

Bis-(Trimethylsilylethyl Diphenyl Phosphine) Rhodium Carbonyl Hydride and Excess Ligand Coordinated with n-Valeraldehyde Complex equilibria with coordinating solvents can be also established at different concentrations and temperatures. Interactions with aldehydes are particularly important since the aldehyde products are always present in the hydroformylation mixtures. Comparative low temperature $^{31}P$ nmr studies of tris-(alkyl diaryl phosphine) rhodium carbonyl hydride solutions in aromatic hydrocarbons and valeraldehyde have shown that valeraldehyde facilitates the dissociation of tris-phosphine complexes and the formation in turn of carbonyl dimer derivatives of the bis-phosphine complex. Under hydrogen pressure, the latter is in equilibrium with the tris-phosphine complex. Aldehydes appear important in the stabilization of the key active intermediate, the coordinatively unsaturated trans-bis-(alkyl diaryl phosphine) rhodium carbonyl hydride, e.g., the bis-SEP complex,

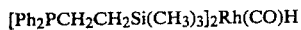

[Ph$_2$PCH$_2$CH$_2$Si(CH$_3$)$_3$]$_2$Rh(CO)H

EXAMPLE 34

Trimethylsilylethyl Diphenyl Phosphine Rhodium Dicarbonyl Complexes

Complex equilibria between various catalytic intermediates derived from trans-bis-phosphine carbonyl hydride could be also studied via similar methods in the presence of varying amounts of excess phosphine ligand. The results of these studies contrast the behavior of the SEP and TPP complexes toward CO and show the influence of excess phosphine ligand in stabilizing the desired catalyst structures.

When solutions of the tris-phosphine rhodium carbonyl hydride complexes and excess phosphine were placed under pressure of CO and varying mixtures of H$_2$ and CO rapid ligand exchange and the formation of bis-carbonyl complexes leading to non-selective hydroformylation were observed. At low temperature, the rate of the ligand exchange was decreased and the $^{31}P$ doublet signals originating from several different rhodium complexes, including the tris-phosphine rhodium carbonyl hydride and bis-phosphine rhodium dicarbonyl hydride, could be observed. It was noted that the ratio of the monocarbonyl complexes to the dicarbonyl complexes increased with increasing H$_2$/CO and P/Rh ratios. Under comparable conditions less of the undesired dicarbonyl complex was formed in the SEP system than in the TPP system. Also, the dicarbonyl SEP complex were converted back to the monocarbonyl complex more readily than the dicarbonyl TPP complex.

The experiments have shown that in the catalyst systems for selective hydroformylation. The concentration of the tris-phosphine rhodium carbonyl hydride is optimized. This complex then acts as a dynamic, stabilizer reservoir and source of the active trans-bis-phosphine carbonyl hydride. The latter is highly reactive in a reversible manner toward olefins as it is indicated by the increased ligand exchange under ethylene pressure.

III. Preparation of Tris-Silylalkyl Diphenyl Phosphine Complexes of Other Transition Metals The novel silyl substituted alkyl diphenyl phosphine complexes of other transition metals can be prepared via known methods which are developed to prepare triaryl or trialkyl phosphine complexes. A method discovered during the course of the present work starts with the readily available triphenyl phosphine complexes of transition metals to prepare the corresponding complexes of silylalkyl diphenyl phosphines via ligand exchange.

EXAMPLE 35

Tris-(Trimethylsilylethyl Diphenyl Phosphine) Iridium Carbonyl Hydride

(Ph$_3$)$_3$Ir(CO)H + 3 Ph$_2$PCH$_2$CH$_2$Si(CH$_3$)$_3$ ⟶

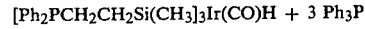

[Ph$_2$PCH$_2$CH$_2$Si(CH$_3$)$_3$]$_3$Ir(CO)H + 3 Ph$_3$P

Tris-(triphenyl phosphine) iridium carbonyl hydride was reacted with the SEP ligand in the manner described in Example 11 to 19. $^{31}P$ nmr spectroscopy of the liquid reaction mixture indicated that the singlet signal of the TPP complex reactant at 12.4 ppm mostly disappeared and an intense signal for the liberated TPP appeared instead. The formation of the SEP complex was shown by the intense new singlet having a chemical shift value of 10.4 ppm.

EXAMPLE 35A

Trimethylsilylethyl Diphenyl Phosphine Cobalt Tricarbonyl Dimer

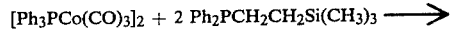

[Ph$_3$PCo(CO)$_3$]$_2$ + 2 Ph$_2$PCH$_2$CH$_2$Si(CH$_3$)$_3$ ⟶

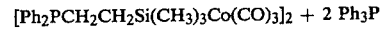

[Ph$_2$PCH$_2$CH$_2$Si(CH$_3$)$_3$Co(CO)$_3$]$_2$ + 2 Ph$_3$P

The cobalt tricarbonyl dimer of TPP was reacted with SEP to yield the desired product of ligand exchange.

IV. Testing of Tris-(Silyl Alkyl Diaryl Phosphine) Rhodium Complex Based Hydroformylation Catalyst Systems

A. General method of Hydroformylation

The hydroformylation of butene-1 to provide linear pentanal and branched 2-methyl butanal products was selected for comparative studies of the catalytic properties of alkyl diaryl phosphine) rhodium carbonyl hydride complexes. The complexes studied were either isolated before use or generated in situ. In some cases, the desired complex was generated from the known tris(triphenyl phosphine) rhodium carbonyl hydride by the addition of the appropriate ligand in varying amounts. According to another standard method, dicarbonyl acetylacetonato rhodium and the appropriate alkyl diaryl phosphine were used as catalyst precursors. In that case, the desired rhodium carbonyl hydride complex was generated by hydrogenation during the hydroformylation experiment. Tris-triphenyl phosphine rhodium carbonyl hydride in the presence of varying excess of triphenyl phosphine was used as a known catalyst standard for comparison.

The experiments were carried out in a 300 ml stainless steel (S) and a 300 ml Hastelloy (H) autoclave, respectively. Both autoclaves were equipped with identical highly effective, impeller type stirrers, operating at 1500 rpm during the experimental runs. The other standard autoclave instrumentation was identical for both units. However, a slightly lower normal to iso aldehyde product ratio (n/i) was observed in unit H. In those cases where the type of autoclave was not specified, a stainless steel unit was used.

The standard batch hydroformylation procedure was the following: the appropriate amounts of rhodium complex were dissolved in 80 g of the proper mixture of free phosphine and solvent. 2-Propylheptyl valerate or 2-ethylhexyl acetate were generally used as standard solvents. Most often, the amount of complex employed provided 100 ppm rhodium concentration. This meant 100 mg, i.e., about 0.1 mole, rhodium per 100 g. Accordingly, 100 mg per kg, about 1 mmole per kg rhodium would be present in 1 kg starting mixture. The excess ligand added to the solvent was usually calculated to provide a ligand to rhodium ratio (L/Rh) of about 140.

The 100 g rhodium complex-ligand solution was placed into the autoclave which was then deaerated by repeated pressurization with nitrogen. The solution under atmospheric nitrogen pressure was then sealed and heated to the reaction temperature, usually 100° C.

When the solution reached 100°, 20 g liquid butene was pressured into the autoclave with a 1 to 4 carbon monoxide-hydrogen initial gas mixture. The butene was followed by the $CO/H_2$ mixture until a pressure of 350 psig was reached. At that point, the supply of 1:4 to 1:5 $CO/H_2$ was shut off and the autoclave was connected to a cylinder of about 1 liter volume containing an about 1:1 $CO/H_2$ feed gas mixture at 1000 psig. The connection was made through a pressure regulating valve set to provide the 1:1 $CO/H_2$ gas to the autoclave to maintain a 350 psig pressure during the reaction. The exact $H_2/CO$ ratio of the feed gas was often varied to maintain the initial $H_2/CO$ ratio in the autoclave. The reaction was typically run to an 80% conversion on the basis of the $H_2/CO$ consumed.

Figure 4:
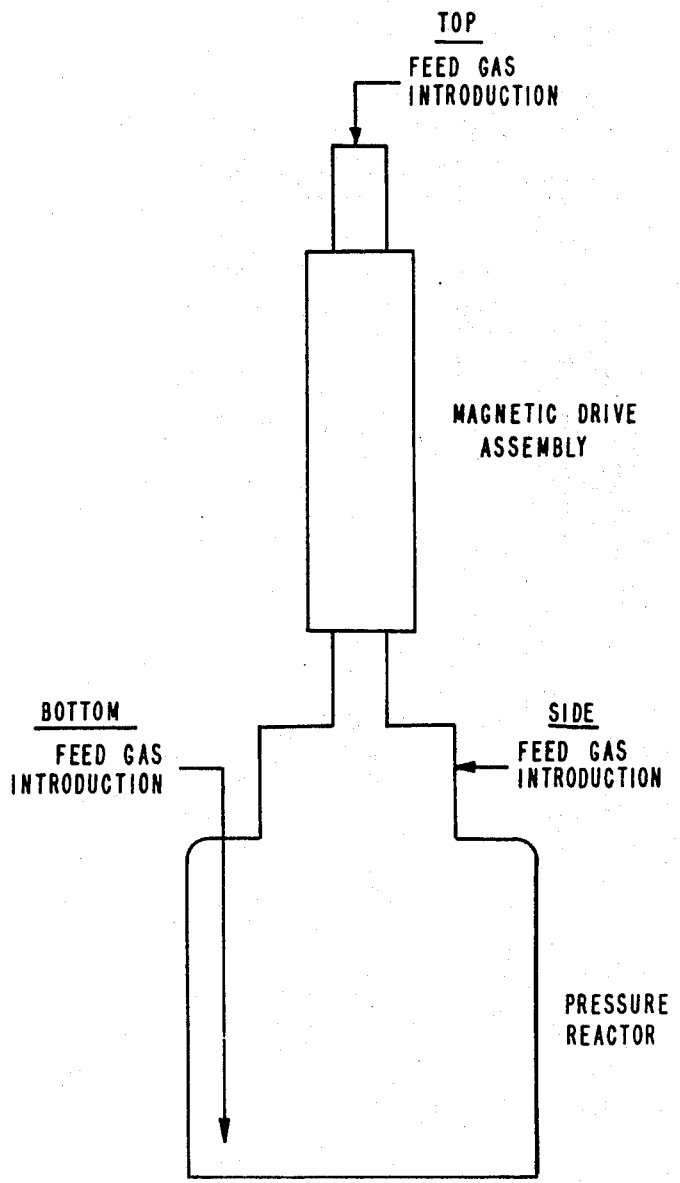
FIG. 4 outlines the different methods of feed gas introduction for hydroformylation on a schematic drawing of an autoclave.

In the standard tests, the autoclaves used were equipped with synthesis gas feed lines adjoining the autoclave above the Magnedrive stirred assembly unit (FIG. 4). It is to be noted that this manner of introducing synthesis gas feed far from the upper level of the liquid reaction mixture (Method A) resulted in an incomplete equilibration of the synthesis gas mixture between the gas and liquid phase. Particularly in those cases where the initial synthesis gas mixture (used to pressure up the reaction mixture) had a $H_2$ to CO ratio of 10 or higher, the CO component of the subsequent one to one feed gas was not effectively delivered from the top into the liquid reaction mixture due to mass transfer limitations. Therefore, the reaction mixture was often "starved" of CO during the early fast phase of the reaction. As a consequence, the $H_2/CO$ ratio in the liquid temporarily rose to very high values. This resulted in particularly high n- to i-aldehyde product ratios. Also, olefin hydrogenation and isomerization became important side reactions. For comparison, the widely studied tris-TPP rhodium carbonyl hydride catalyst system was used as a standard throughout the work. Generally, the reaction was run to an 80% conversion on the basis of the $H_2/CO$ consumed when using this method.

In those instances where the effect of $H_2$ to CO ratios and the effect of CO partial pressure were especially studied, the synthesis gas feed was introduced at the side of the autoclave through a side arm just above the liquid level (FIG. 4, Method B). This method of operation largely avoided any temporary rise of $H_2/CO$ ratios and drastically reduced hydrogenation and isomerization in cases where the initial $H_2/CO$ ratio was high.

In the third method of operation, the synthesis gas was introduced into the liquid reaction mixture at the bottom, close to the stirrer through a sintered inductor to assure small bubble size and instantaneous mixing (FIG. 4, Method C). This method was the best for avoiding higher than equilibrium $H_2/CO$ ratios during the reaction. As such the method gave the smallest n/i ratios of isomeric aldehyde products and the least hydrogenation and isomerization of the olefin, i.e., the highest selectivity for total, i.e., n+i, aldehyde products. Using this method, the reaction was usually run to 50% conversion on the basis of the consumed synthesis gas. Special studies were also made in a continuous feed introduction and product flashoff operation. This allowed a continuous control of partial pressures and such provided the most accurate results.

The progress of the hydroformylation was followed on the basis of the amount of 1:1 $CO/H_2$ consumed. The latter was calculated on the basis of the pressure drop in the 1 liter $CO/H_2$ cylinder. Reactant conversion calculated on the basis of CO consumption was plotted against the reaction time to determine the reaction rate. The reaction rate was expressed as the fraction of the theoretical $CO/H_2$ requirement consumed per minute (k $min^{-1}$). The reaction was discontinued when the reaction rate drastically dropped. Dependent on the side reaction, such as butene-1 hydrogenation and butene-1 to butene-2 isomerization, the reaction temperature and the stability of the catalyst complex in the mixture, such a rate drop occurred generally between 80–98% CO conversion.

When the reaction was to be discontinued, the $CO/H_2$ feed valve was shut and the autoclave was immediately cooled with cool water. In case of low conversions, ice bath was used. When cooling was complete, the synthesis gas was released slowly. The residual liquid was visually observed for catalyst decomposition. A dark orange to brown color of the originally yellow mixture indicated increasing degrees of catalyst decomposition. Severe catalyst decomposition usually resulted in the precipitation of dark solids.

Analyses of the residual liquid mixture were carried out using gas chromatography. The liquids were analyzed in a gc instrument using flame ionization detector. By this instrument, the $C_4$ hydrocarbons were detected. Due to the lower response of this detector to the aldehydes, the intensity of the hydrocarbon peaks was multiplied usually by 0.7 to obtain the necessary concentration correction. The individual, gaseous $C_4$ hydrocarbons were separated by another chromatograph. At first, these gases were separated from the liquids and then the individual components of the gas were chromatographed and detected by a thermal conductivity detector.

B. 1-Butene Hydroformylation (Examples 36–43)

The following description of 1-butene hydroformylation catalysis will be exemplified by a detailed description of the tris-(trimethylsilylethyl diphenyl phosphine) rhodium carbonyl hydride, i.e., SEP complex, plus SEP system. For comparison, detailed data will also be provided on the known tris-(triphenyl phosphine) rhodium carbonyl hydride, i.e., TPP complex, plus TPP system. For comparison, detailed data is also provided on the known tris-(triphenyl phosphine) rhodium carbonyl hydride, i.e., TPP complex plus TPP, system. It is noted that Method A, introducing the synthesis gas feed at the top of the reactor assembly, was used in several Examples as indicated hereafter. Consequently, CO starvation did occur at high reaction rates and these data are not available for determining physicochemical constants, such as activation energies.

EXAMPLE 36

Tris-(Trimethylsilylethyl Diphenyl Phosphine) Rhodium Carbonyl Hydride as a Catalyst in the Presence of 140-Fold Ligand Excess at Different Temperatures The complex of Example 10 was studied at the 107 ppm rhodium level in the presence of 140-fold (0.14 M) trimethylsilylethyl diphenyl phosphine (SEP) ligand as a butene hydroformylation catalyst using the general procedure describe above for Method A. Comparative experiments were run using 107 ppm rhodium as a tris(-triphenyl phosphine) carbonyl hydride complex with 140-fold triphenyl phosphine (TPP). Reaction rates, n/i product ratios, conversions and byproducts were determined at various temperatures. The results are shown by Table III.

The data of the table show that both the SEP and the TPP based catalyst systems are highly active and produce a high ratio of n/i products at most temperatures. However, the temperature dependence of the two systems is very different. The procedure used in the runs was that of Method A.

isomerization of the butene-1 reactant. The SEP system remains clear, bright yellow in appearance, even at 145°.

The known TPP catalyst system exhibits the same increased activity at 120° and 140°. However, the n/i ratios in this case are monotonously reduced with increasing temperatures. At 145°, the n/i ratio of products is significantly lower in the TPP than in the SEP system. At 145°, the reaction rate of the TPP system also drops. Decomposition of this system at this temperature is indicated by darkening of the reaction mixture.

EXAMPLE 37

Tris-(Trimethylsilylethyl Diphenyl Phosphine) Rhodium Carbonyl Hydride Complex as a Catalyst in the Presence of 1 $\overline{M}$ Excess Ligand at Different Temperatures The SEP-rhodium complex catalyst system and the corresponding TPP-rhodium systems were also compared as butene hydroformylation catalysts using Method C. This comparison was made in considerable detail of systems containing a high excess, i.e., 1 molal concentration of excess ligand in the starting reaction mixture. Data were obtained at temperatures ranging from 100°–160° C. The results are shown in Table IV.

To assess the effect of changing the experimental

TABLE III

HYDROFORMYLATION AT DIFFERENT TEMPERATURES

Feed: Butene-1 and 1:4 CO/H$_2$ at 350 psi
Catalyst: L$_3$Rh(CO)H, Rh 107 ppm, Rh/L = 140
SEP Ligand: (CH$_3$)$_3$SiCH$_2$CH$_2$P$\phi_2$  TPP Ligand: $\phi_3$P

| Variable Conditions of Catalysis | | Reaction Rates and Selectivities | | | | | | Details |
|---|---|---|---|---|---|---|---|---|
| | | | | | | By-Product, Mole % in Product Mixture | | Exact |
| Seq. No. | Catalyst Ligand | Reaction Temp., °C. | Fraction of CO/H$_2$ Reacted k, min$^{-1}$ | Product n/i Ratio | Reaction Time Min. | Butene Conversion % | Butane | Butene-2 | Rh Conc. ppm |
| 1 | SEP | 100 | 0.03 | 6.1 | 35 | 86.9 | 2.0 | 3.8 | 106 |
| 2 | | 120 | 0.10 | 6.2 | 35 | 96.5 | 9.4 | 6.2 | 106 |
| 3 | | 140 | 0.21 | 5.7 | 15 | 97.5 | 14.5 | 12.4 | 108 |
| 4 | | 145 | 0.27 | 5.0 | 15 | 95.2 | 11.9 | 12.1 | 109 |
| 5 | TTP | 100 | 0.21 | 7.5 | 35 | 98.9 | 10.7 | 12.1 | 107 |
| 6 | | 120 | 0.34 | 5.9 | 10 | 97.3 | 9.3 | 12.2 | 104 |
| 7 | | 140 | 0.38 | 3.4 | 10 | 98.2 | 11.2 | 21.9 | 105 |
| 8 | | 145 | 0.27 | 2.4 | 15 | 97.7 | 11.9 | 26.0 | 103 |

The novel SEP catalyst system exhibits an increasing activity with elevated temperatures. At 100° and 120° the n/i ratio of products is about the same and there is only a small n/i drop at 145°. High butene conversion is observed at all temperatures. The only adverse effect of temperature increase is the increased hyrogenation and procedure from Method A to C, Table IV also shows some data at 0.14 $\overline{M}$ excess ligand concentration (Seq. Nos. 1, 2 and 8). This ligand concentration was widely used in the previous examples with Method A. The comparison with Table III shows that the use of Method C results

TABLE IV

Hydroformylation of 1-Butene with Tris-Phosphine Rhodium Carbonyl Hydride Catalyst Using Ph$_2$PCH$_2$CH$_2$Si(CH$_3$)$_3$ (DTS) or Ph$_3$P (TPP)

Reactions at 350 psi (24.7 atm) of 5/1 H$_2$/CO with 20 g 1-butene and 80 g of phosphine plus 2-ethylhexyl acetate solvent, using AcacRh(CO)$_2$ as catalyst precursor and introducing the feed gas into the stirred reaction mixture.

| Experiment | | Catalyst System Parameters | | | | H$_2$/CO Consumption Dependent Factors (50% Conversion) | | | Aldehyde Product Parameters | | | | By-product Selectivity, % | |
|---|---|---|---|---|---|---|---|---|---|---|---|---|---|---|
| | | | | | | | | | Linearity | | Hydroformylation | | | |
| | | | | | | | | | | n × 100 | Selectivity | | 2- | |
| Seq. No. | Run No. | Temp. °C. | M in Mix at start | Rh Conc. mM | P$^b$/ Rh | Feed Ratio H$_2$/CO Final | H$_2$/ CO | Rate Constant k, min$^{-1}$ | Reaction Time min. | n/i Ratio | n + i % | n + i % | n- % | i- % | Bu- tenes | Bu- tanes |
| DTS | | | | | | | | | | | | | | | | |
| 1 | 245 | 145 | 0.14 | 0.25 | 560 | 54/46 | 5.9 | 0.083 | 8.5 | 4.9 | 82.9 | 89.8 | 74.5 | 15.3 | 6.8 | 3.5 |
| 2 | 246 | 145 | 0.14 | 0.10 | 140 | 54/46 | 5.5 | 0.035 | 19 | 4.6 | 82.2 | 90.7 | 74.6 | 16.1 | 6.5 | 2.8 |
| 3 | 249 | 110 | 1.0 | 4.0 | 250 | 52/48 | 4.9 | 0.032 | 22 | 7.6 | 88.4 | 93.9 | 83.0 | 10.9 | 4.3 | 1.8 |
| 4 | 142 | 125 | 1.0 | 1.0 | 1000 | 52/48 | 4.6 | 0.026 | 27 | 8.2 | 89.1 | 94.1 | 83.8 | 10.2 | 4.0 | 1.9 |

TABLE IV-continued

Hydroformylation of 1-Butene with Tris-Phosphine Rhodium Carbonyl Hydride Catalyst Using Ph₂PCH₂CH₂Si(CH₃)₃ (DTS) or Ph₃P (TPP)

Reactions at 350 psi (24.7 atm) of 5/1 H$_2$/CO with 20 g 1-butene and 80 g of phosphine plus 2-ethylhexyl acetate solvent, using AcacRh(CO)$_2$ as catalyst precursor and introducing the feed gas into the stirred reaction mixture.

| Experiment | | | Catalyst System Parameters | | | | H$_2$/CO Consumption Dependent Factors (50% Conversion) | | | Aldehyde Product Parameters | | | | | By-product Selectivity, % | |
|---|---|---|---|---|---|---|---|---|---|---|---|---|---|---|---|---|
| | | | | | | | | | | Linearity | Hydroformylation Selectivity | | | | 2- | |
| Seq. No. | Run No. | Temp. °C. | M in Mix at start | Rh Conc. m$\overline{M}$ | P$^b$/Rh | Feed Ratio H$_2$/CO | H$_2$/CO Final | Rate Constant k, min$^{-1}$ | Reaction Time min. | n/i Ratio | n + i % | n + i % | n- % | i- % | Butenes | Butanes |
| 5 | 138 | 135 | 1.0 | 1.0 | 1000 | 53/47 | 5.1 | 0.046 | 15 | 9.8 | 90.8 | 90.2 | 81.9 | 8.3 | 5.9 | 3.9 |
| 6 | 101 | 145 | 1.0 | 1.0 | 1000 | 54/46 | 6.9 | 0.073 | 10 | 11.4 | 91.9 | 89.3 | 82.1 | 7.2 | 6.8 | 3.9 |
| 7 TPP | 247 | 160 | 1.0 | 0.5 | 2000 | 56/44 | 6.9 | 0.065 | 11 | 11.3 | 91.9 | 82.8 | 76.1 | 6.7 | 10.8 | 6.4 |
| 8 | 171 | 145 | 0.14 | 0.05 | 280 | 54/46 | 5.8 | 0.040 | 18 | 4.1 | 80.2 | 83.0 | 66.6 | 16.5 | 13.4 | 3.5 |
| 9 | 135 | 110 | 1.0 | 0.5 | 2000 | 52/48 | 5.1 | 0.017 | 40 | 13.0 | 92.8 | 91.3 | 84.7 | 6.5 | 5.7 | 3.0 |
| 10 | 130 | 125 | 1.0 | 0.5 | 2000 | 52/48 | 4.7 | 0.058 | 12 | 11.9 | 92.3 | 89.1 | 82.2 | 6.9 | 7.9 | 3.1 |
| 11 | 129 | 135 | 1.0 | 0.5 | 2000 | 54/46 | 6.5 | 0.078 | 9 | 12.8 | 92.7 | 84.2 | 78.1 | 6.1 | 10.7 | 5.1 |
| 12 | 128 | 145 | 1.0 | 0.5 | 2000 | 54/46 | 5.4 | 0.104 | 7 | 10.7 | 91.5 | 80.4 | 73.6 | 6.9 | 13.2 | 6.4 |
| 13 | 144 | 160 | 1.0 | 0.25 | 4000 | 56/44 | 5.6 | 0.064 | 11 | 7.6 | 88.4 | 78.9 | 69.7 | 9.2 | 15.8 | 5.3 | in a lower n/i ratio of aldehydes but a higher n+i aldehyde selectivity, i.e., lower by-product formation.

In general, the use of the high 1 $\overline{M}$, ligand excess increased both the n/i ratio and the n+i selectivity in both the SEP and TPP systems at all temperatures (Seq. Nos. 3 to 7 and 9 to 13). The use of the SEP system always resulted in a somewhat higher total aldehyde selectivity. However, in the 145°–160° C. range, the selectivity of the SEP system was considerably better, apparently due to its increased thermal stability. The n/i ratio of the aldehydes produced in the SEP catalyzed reaction was even slightly increased as the temperature was raised from 110° to 145° C. This was probably due to the reduced CO concentrations in the liquid reaction mixture at increased temperatures.

Figure 5A:
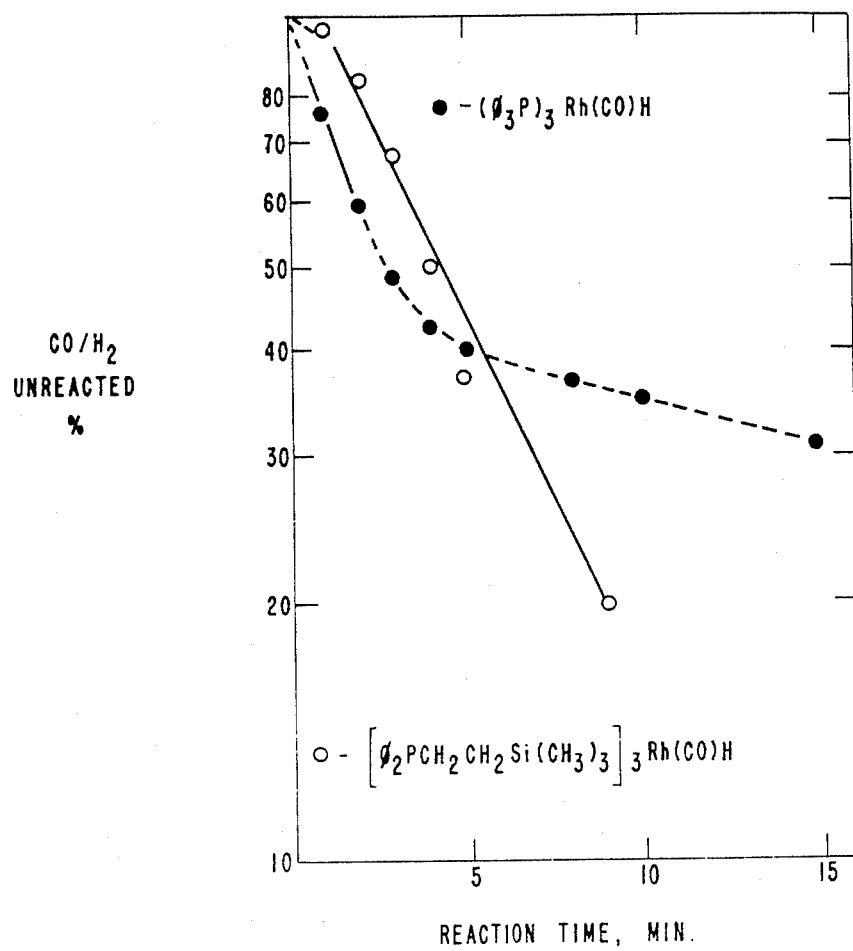
FIG. 5A and 5B indicate catalyst stability of the TPP and EP complex during hydroformylation at 145° C. and 100° C., respectively.
Figure 5B:
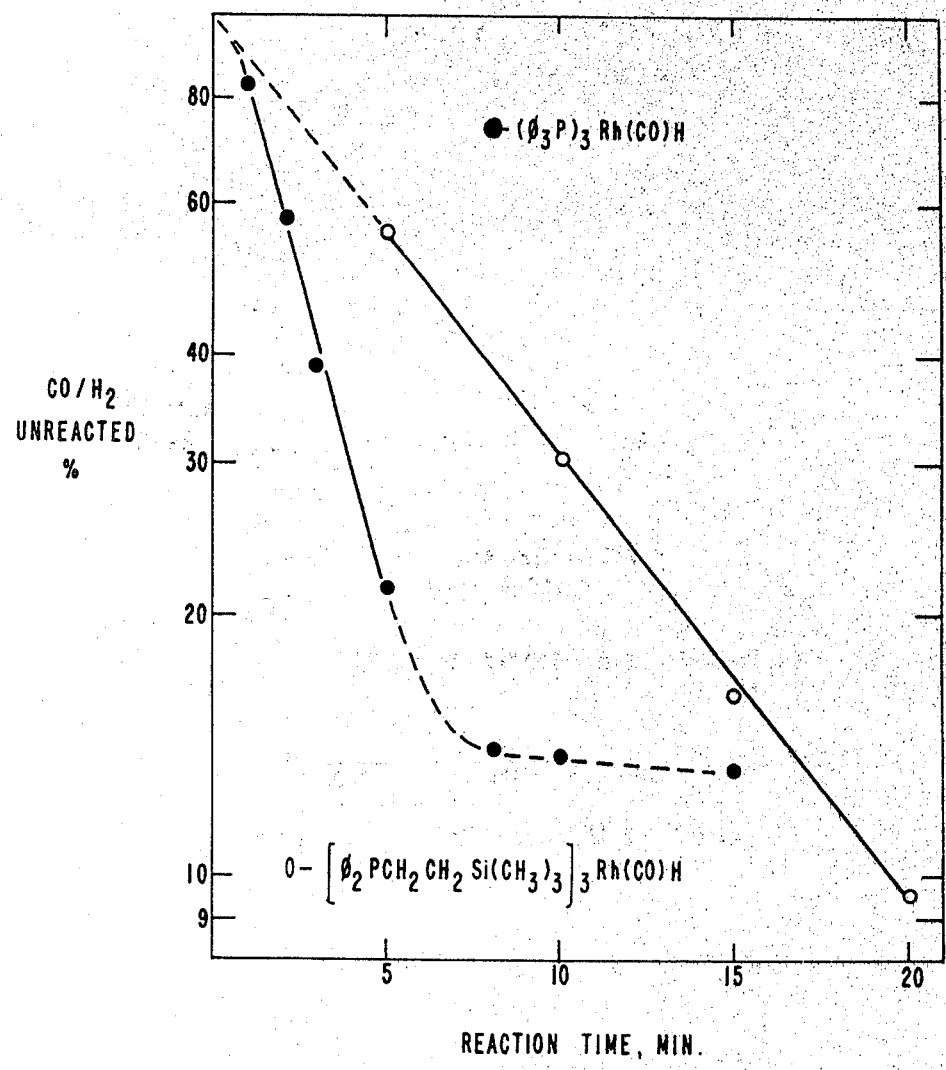

The general lesser total (n+i) aldehyde selectivity of the TPP system is mainly due to the significant isomerization of the 1-butene reactant to 2-butenes at 160° C., the n/i ratio of the aldehydes is also decreased greatly in the TPP system. At this temperature, the TPP catalyst system is basically changed, although no gross instability could be observed during the short reaction period. The behavior of the SEP and TPP systems is compared by FIGS. 5A and 5B.

EXAMPLE 38

Tris-(Trimethylsilylethyl Diphenyl Phosphine) Rhodium Carbonyl Hydride as a Catalyst at Different Levels of Excess Ligand Concentrations The complex catalyst of Example 10 was tudied mainly at the 105 ppm rhodium level and at 100° reaction temperature to determine the effect of the excess trimethylsilylethyl diphenyl phosphine ligand. (SEP). The SEP concentration used ranged from 5 to 149 mmole per liter. Some comparative experiments were also carried out using tris-(triphenyl phosphine) rhodium carbonyl hydride and varying excess concentrations of the corresponding triphenyl phosphine ligand. (TTP). The results of these studies are shown in Table V. The procedure used in the runs was that of Method A.

TABLE V

HYDROFORMYLATION AT DIFFERENT LEVELS OF EXCESS LIGAND CONCENTRATIONS

Feed: Butene-1 and 1:4 CO/H$_2$ at 350 psi
Catalyst: L$_3$Rh(CO)H SEP Ligand: (CH$_3$)$_3$SiCH$_2$CH$_2$Pφ$_2$ TPP Ligand: φ$_3$P

| | Variable Conditions of Catalysts | | | | | Reaction Rates and Selectivities | | | |
|---|---|---|---|---|---|---|---|---|---|
| Seq. No. | Catalyst Ligand | Reaction Temp., °C. | Auto-Clave | Excess Ligand Conc. mMole/lit. | Rhodium Conc. ppm | Ligand to Rh Ratio L/Rh | Fraction of CO/H$_2$ Reacted k min$^{-1}$ | Product Linearity Ratio, n/i | Reaction Time min. | CO Conversion % |
| 1 | SEP | 100 | H | 5 | 105 | 5.2 | 0.24 | 3.5 | 20 | 88.7 |
| 2 | | | | 24 | 105 | 24.2 | 0.09 | 4.0 | 35 | 87.1 |
| 3 | | | S | 28 | 105 | 28 | 0.12 | 4.4 | 35 | 88.0 |
| 4 | | | | 56 | 217 | 28 | 0.12 | 5.4 | 30 | 94.2 |
| 5 | | | | 143 | 105 | 143 | 0.03 | 6.1 | 35 | 83.6 |
| 6 | | 120 | S | 29 | 105 | 29 | 0.30 | 4.5 | 15 | 93.0 |
| 7 | | | | 60 | 210 | 30 | 0.25 | 5.7 | 15 | 89.6 |
| 8 | | | | 149 | 105 | 105 | 0.10 | 6.2 | 35 | 88.1 |
| 9 | TTP | 100 | H | 5 | 105 | 5 | 0.28 | 3.0 | 15 | 80.8 |
| 10 | | | | 142 | 102 | 142 | 0.17 | 3.8 | 35 | 96.5 |
| 11 | | | S | 27 | 105 | 27 | 0.31 | 4.7 | 15 | 86.6 |
| 12 | | | | 143 | 104 | 143 | 0.03 | 6.1 | 35 | 83.6 | catalyst systems. There is an apparent inhibition and stabilization of both systems at high ligand concentrations. However, the behavior of the two catalysts is significantly different at relatively low excess ligand concentrations.

The novel SEP catalyst system leads to higher n/i product ratio than the TPP system at five mmole/l excess ligand concentration (Seq. No. 1 vs. Seq. No. 9).

At the intermediate SEP concentration of 56 mmole, there is a good selectivity and sufficient reaction rate (Seq. No. 4). It is interesting to observe that the positive effect of increasing catalyst complex concentration on the reaction rate can be counterbalanced by the inhibiting effect of increased SEP concentration (compare Seq. Nos. 3 vs. 4 and 6 vs. 7). Clearly, the SEP concentration is more important than the SEP/Rh ratio. At the high SEP level of 143, there is some further increase of the n/i ratio, but the reaction rate is cut to about one fourth (compare Seq. Nos. 4 and 5). At this level, the rate can be increased while maintaining the high n/l ratio by increasing the reaction temperature (see Seq. No. 8 and the table of the previous example).

The effect of different ligand to rhodium ratios on the n/i ratios of butene hydroformylation at different temperatures was further examined. The results are summarized by FIG. 6.

The figure shows that as the SEP/Rh ratio changes from about 140 to about 1000, and n/i ratio at 80% conversion and 170° C. reaction temperature changes from about 2 to 7. The major change in the percentage of the n-aldehyde product occurs in the 140 to 500 L/Rh range. It was shown in additional experiments that there was very little further selectivity increase when the SEP ligand was used as the solvent (i.e., in about 75% concentration).

The increased selectivity to linear aldehyde is a consequence of the increased catalyst stability in these experiments. The increased catalyst stability is also reflected in a decreasing darkening of the reaction mixture with increasing ligand concentration. Another sign of the increased stability is the better maintenance of the hydroformylation rate with increasing conversion. Finally, it was also noted that the increased ligand concentration resulted in a moderate supression of the rate of hydrogenation. Nevertheless, hydrogenation remained significant enough to cause a decreasing $H_2/CO$ ratio during the reaction.

Figure 6:
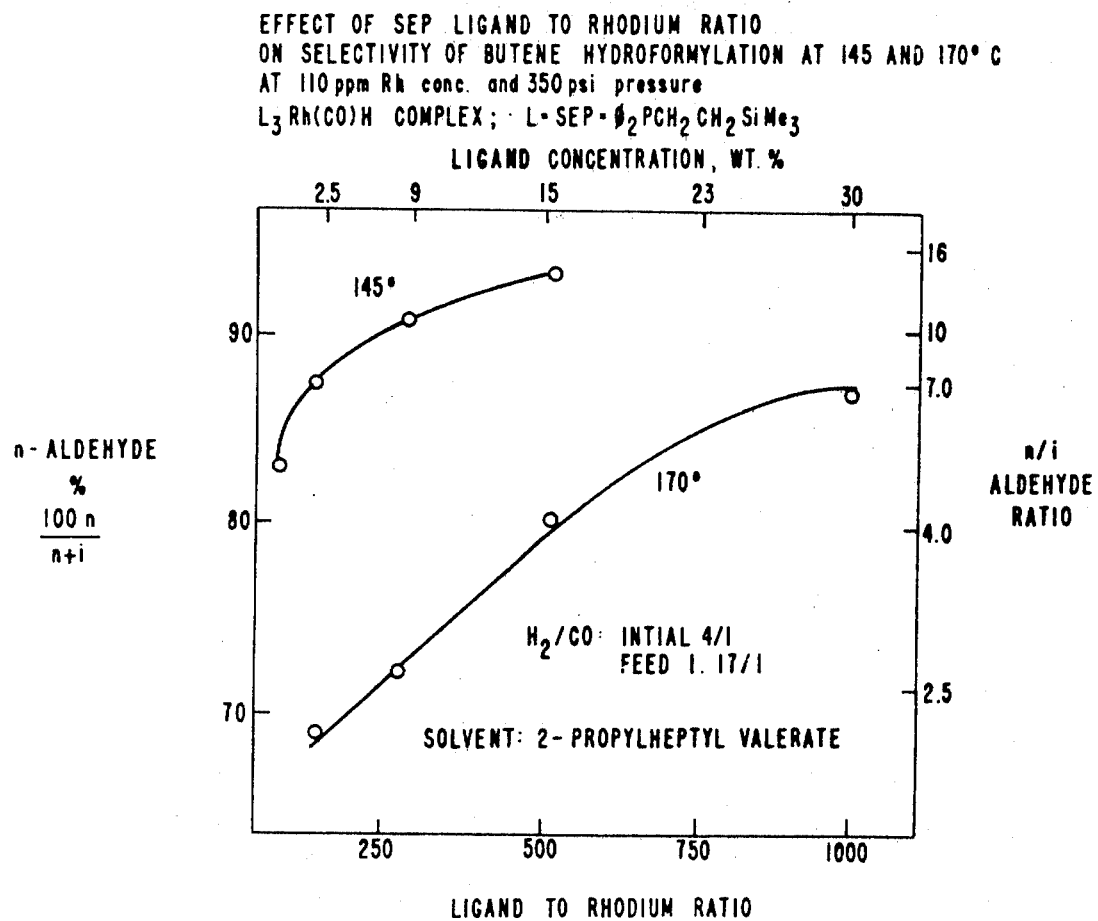
FIG. 6 shows the effect of SEP ligand to rhodium ratio on the n/i ratio of the aldehyde products at 145° C. and 170° C.

Similar studies of the effect of increased SEP/Rh ratio were carried out at 160°, 145° and 120° C. The data obtained at 145° are also shown in FIG. 6. The lower the reaction temperature, the less effect of increased L/Rh ratios was observed. At decreasing temperatures most of the effects were observed in the range of increasingly low L/Rh ratios. Also, the main effect was on selectivity rather than on stability.

EXAMPLE 39

Hydroformylation Selectivity of Tris-(Trimethylsilylethyl Diphenyl Phosphine) Rhodium Carbonyl Hydride Excess Ligand Catalyst System at Different Olefin Conversions Butene-1 was hydroformylated in the Hastelloy unit according to the general procedure by Method A. The catalyst and ligand concentrations were higher than usual and the reaction conditions milder as shown in Table VI The reaction mixture was frequently sampled during the process and the samples were analyzed by gc to determine the relative selectivites to n- and i-aldehyde products and hydrocarbon by-products as a function of butene-1 conversion. The detailed data are given in Table VI.

The data of Table VI indicate that the n-to i-ratio of aldehydes in the reaction is decreasing as the conversion increases. Up to about 60% butene conversion, the n/i ratio stays above 18.5, although it is steadily dropping (see Sample Nos. 1–2). In the 72–78% conversion range, the n/i ratio is about 14. Once butene-1 conversion reaches 90%, the n/i ratio of the product mixture is down to about 11.5.

It was also observed that during the conversion of about 25% of the butene, the total aldehydes to hydrocarbon by-products ratio was lower than at higher conversions (about 70/30 versus 90/10). It is believed that this is due to uncontrolled nonequilibrium conditions early during the reaction. Almost all the hydrogenation occurred during the first 10 minutes of the reaction. During the early, very fast past of the reaction, the liquid reaction medium became starved of CO. Due to the resulting low CO partial pressure, the n/i product ratio became very high. However, the amount of CO during some of this period was so insufficient that much hydrogenation and isomerization occurred. In a continuous process, where the low optimum concentation of CO could be more accurately maintained, high selectivity to aldehydes could probably be better achieved without producing significant amounts of by-products.

TABLE VI

| HYDROFORMYLATION SELECTIVITY AT DIFFERENT OLEFIN CONVERSION LEVELS | | | | | | | | | |
|---|---|---|---|---|---|---|---|---|---|
| Feed: Butene-1 and 1:4 $CO/H_2$ at 130 psi at 110° C. under 130 psi Catalyst: $L_3RH(CO)H$, Rh 212 ppm, L Excess 300 mMole, L/Rh 140 L: $\phi_2PCH_2CH_2Si(CH_3)_3$ | | | | | | | | | |
| | Conversion Related Data | | | Aldehyde | Mole % Selectivity to Various Compounds | | | | |
| Sample No. | Butene-1 Conversion % | Conversion, % Based on $CO/H_2$ Consumed | Reaction Time, Min | Product Linearity Ratio, n/i | Aldehyde Products | | Butene Hydrogenation Product | 2-Butene By-Products | |
| | | | | | n | i | | cis | trans |
| 1 | 26.4 | 21.9 | 10 | 26 | 68.4 | 2.7 | 11.9 | 9.7 | 7.3 |
| 2 | 46.9 | 36.0 | 15 | 25 | 77.9 | 3.1 | 7.4 | 6.7 | 4.9 |
| 3 | 61.6 | 50.0 | 20 | 18.5 | 79.7 | 4.3 | 6.1 | 5.8 | 4.2 |
| 4 | 72.0 | 61.4 | 25 | 13.9 | 80.2 | 5.8 | 5.2 | 5.2 | 3.7 |
| 5 | 78.0 | 69.4 | 30 | 14.0 | 79.6 | 5.7 | 5.4 | 5.4 | 3.9 |
| 6 | 90.0 | 79.9 | 40 | 11.6 | 82.1 | 7.1 | 3.9 | 4.0 | 2.9 |
| 7 | 90.5 | 87.9 | 60 | 11.3 | 81.9 | 7.2 | 4.0 | 4.0 | 3.0 |

EXAMPLE 40

Hydroformylation with the Tris-(Trimethylsilylethyl Diphenyl Phosphine) Rhodium Complex System Derived Via Ligand Exchange from Tris-(Triphenyl Phosphine) Rhodium Carbonyl Hydride In a series of experiments, tris-(triphenyl phosphine) rhodium carbonyl hydride was reacted with a varying excess concentration of the novel substituted alkyl diphenyl alkyl phosphines. This resulted in the formation of the novel catalysts of the present invention which were studied for their catalytic properties in the usual manner in the Hastelloy unit (H).

Tris-(triphenyl phosphine) rhodium carbonyl hydride, 0.1 g (0.1 mmole), was mixed with 80 g of a mixture of 4 g (14 mmole) of trimethylsilylethyl diphenyl phosphine and 76 g 2-propylheptyl valerate to provide an SEP catalyst system. For comparison, the same complex was also mixed with 80 g of a mixture of 3.7 g (14 mmole) of triphenyl phosphine to provide a TPP catalyst system. This provided two systems having 105 ppm rhodium and a 140 fold ligand excess.

Butene hydroformylations were then carried out with both catalyst systems at 100° C. as described by Method A. The results indicated that the main catalytic species of the SEP system is an SEP complex. The reaction rate of the SEP system was about 1/6 of the TPP system (k min$^{-1}$ values of 0.02 and 0.12, respectively). The n/i product ratios were about the same (4.2).

Other SEP catalyst systems were made up the same way except for the different L/Rh ratios: 25 and 5:1. They were also employed successfully for butene hydroformylation.

EXAMPLE 41

Hydroformylation with the Tris-(Trimethylsilylethyl Diphenyl Phosphine) Rhodium Complex System at Different H$_2$/CO Ratios For a further study of the effect of the H$_2$/CO ratios on hydroformylation selectivity, the feed gas was provided through the side arm of the autoclave as described in Method B to provide conditions during the reaction which are closer to equilibrium.

The SEP complex catalyst was formed in situ during hydroformylation from acetylacetonato dicarbonyl rhodium. The H$_2$/CO ratios of both the initial H$_2$/CO gas and the final unreacted synthesis gas, in the head space of the autoclave, were analyzed. The H$_2$/CO ratio of the feed gas was adjusted to keep the initial and final H$_2$/CO ratios the same as much as possible.

The results are shown by Table VII. The data show that as the H$_2$/CO ratio was increased from 1 to 20 the ratio of n- to i-aldehydes was increased. It is also interesting to note that having the side arm feed resulted in much less 1-butene isomerization and hydrogenation than obtained previously with top feeding.

Comparative side arm feed experiments were also carried out using the known TPP catalyst system at the same concentration. At 120° C., significant side reactions continued to occur. Apparently, equilibrium conditions were not sufficiently approached. Consequently, further experiments were carried out at 90° C. where the reaction rate is sufficiently smaller to avoid side reactions. The results are also shown by Table VII. They show that TPP at 90° C. exhibits a similar behavior to that of SEP at 120° C. The n/i ratios are slightly higher for TPP, apparently due to a higher average of H$_2$/CO ratios.

TABLE VII

1-BUTENE HYDROFORMYLATION WITH SYNTHESIS GAS OF VARYING H$_2$/CO RATIO IN THE PRESENCE OF SEP COMPLEX AND TPP COMPLEX CATALYSTS

Total Pressure 350 psi (260 Atm.); Catalyst: L$_3$Rh(CO)H; L/RH = 140, Rh = 110 ppm
Solvent: 2-Ethylhexyl Acetate

| Seq. No. | Ligand | Reaction Temp. °C. | H$_2$/CO Ratio Initial | Feed | Final | CO Partial Pressure pCO, psi Initial | Final | Fraction of H$_2$CO Reacted Rate Constant k, min$^{-1}$ | Conversion % | Reaction Time, Min. | Aldehyde Product Linearity Ratio n/i | %, 100n n+i | Selectivities to Various Compounds, % Aldehydes n | i | Butane | 2-Butene |
|---|---|---|---|---|---|---|---|---|---|---|---|---|---|---|---|---|
| 1 | SEP | 120 | 1.18 | 1.08 | 1.36 | 160 | 149 | 0.115 | 81 | 13 | 3.09 | 7.56 | 73.7 | 23.8 | 0.6 | 1.8 |
| 2 | SEP | 120 | 5.0 | 1.08 | 4.8 | 59 | 60 | 0.082 | 81 | 22 | 4.56 | 8.20 | 78.2 | 17.1 | 1.7 | 2.9 |
| 3 | SEP | 120 | 10.0 | 1.08 | 7.8 | 31 | 39 | 0.090 | 82 | 30 | 6.60 | 86.8 | 80.8 | 12.2 | 2.8 | 3.2 |
| 4 | SEP | 120 | 15.0 | 1.17 | 10.4 | 22 | 30 | 0.116 | 81 | 15 | 8.22 | 89.2 | 80.4 | 9.8 | 4.4 | 5.3 |
| 5 | TPP | 90 | 1.08 | 1.08 | 1.8 | 168 | 125 | 0.060 | 81 | 29 | 3.76 | 79.0 | 77.0 | 20.5 | 0.8 | 1.7 |
| 6 | TPP | 90 | 5.0 | 1.08 | 9.0 | 59 | 35 | 0.059 | 81 | 28 | 5.50 | 84.6 | 80.5 | 14.7 | 1.2 | 3.6 |
| 7 | TPP | 90 | 10.0 | 1.08 | 10.5 | 31 | 30 | 0.062 | 80 | 26 | 6.70 | 87.0 | 81.0 | 12.1 | 2.0 | 4.8 |
| 8 | TPP | 90 | 15 | 1.17 | 18 | 22 | 18 | 0.062 | 80 | 26 | 8.70 | 89.7 | 80.2 | 9.2 | 4.6 | 6.0 |

EXAMPLE 42

Figure 7:
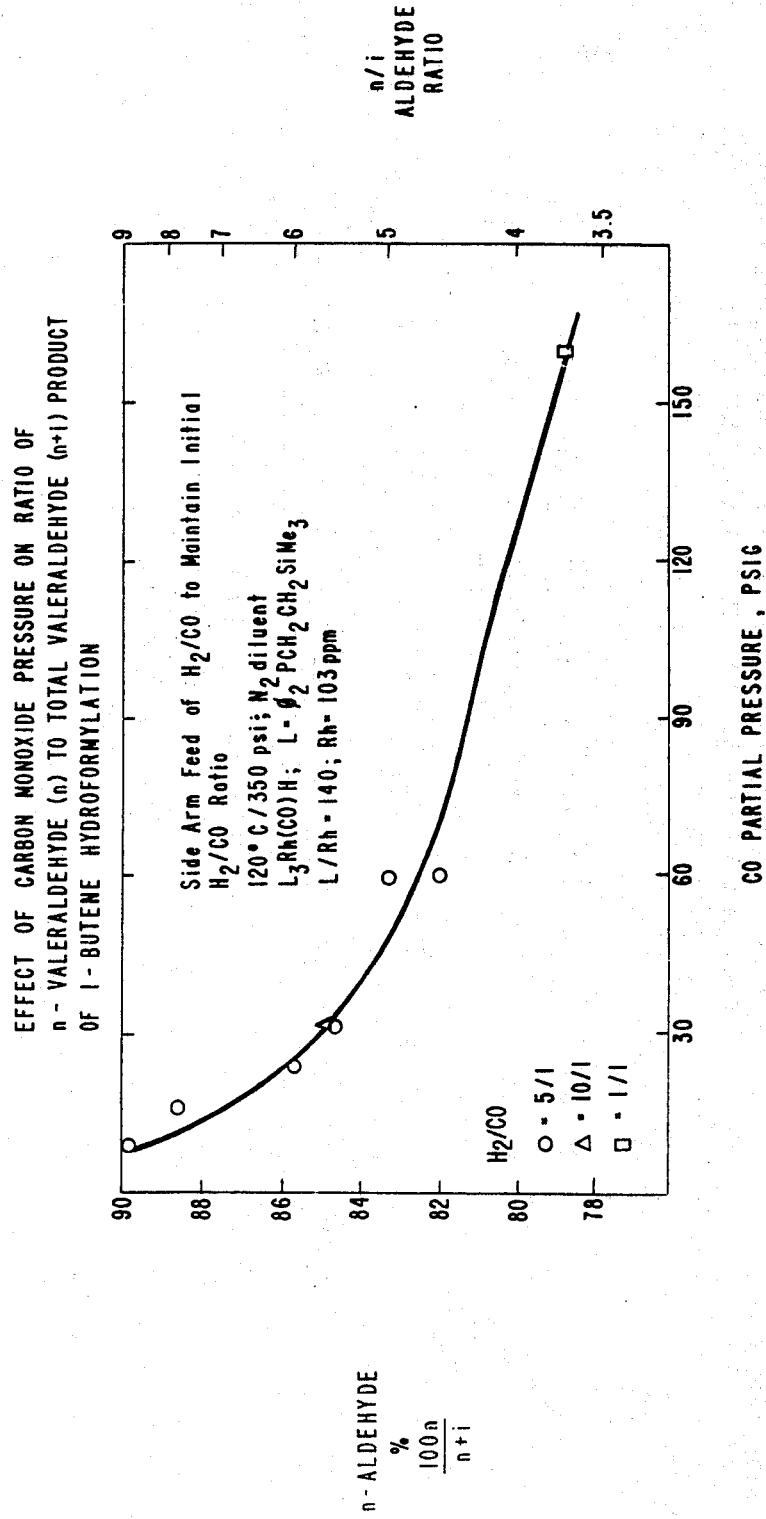
FIG. 7 shows the effect of CO partial pressure of the n/i ratio of aldehyde products at 120° C.

Hydroformylation with the Tris-(Trimethylsilylethyl Diphenyl Phosphine) Rhodium Complex System at Different CO Partial Pressures The results of the type of experiments described in Example 37 were plotted in FIG. 7 to show the dependence of n/i aldehyde product ratios on the CO partial pressures. In additional experiments, the H$_2$/CO ratios were kept constant with changing CO partial pressures by maintaining an appropriate fraction of the total 350 psi (26 Atm) total gas pressure by N$_2$ gas.

There was relatively little change of reaction rates.

The FIGURE shows that decreasing CO partial pressures result in higher n/i product ratios even though the H$_2$/CO ratio is kept constant. The dependence of the n/i ratios is particularly strong in the low CO partial pressure range.

EXAMPLE 43

Comparative Hydroformylation with Tris-(Trihydrocarbylsilylalkyl Diphenyl Phosphine) Rhodium Carbonyl Hyrdride Based Catalyst Systems In a series of experiments, shown by Table VIII, various silyl substituted alkyl diphenyl phosphine complexes of Examples 11 to 16 were tested as 1-butene hydroformylation catalysts under conditions of Method A using top synthesis gas feed. The data indicate, that with the exception of the last catalyst, the complexes tested show the same type of catalyst behavior as the previously discussed SEP complex. The last complex tested, i.e., the one based on the tri-methylsilylmethyl ligand showed less selectivity than the others even at the relatively low hydroformylation temperature used in this case.

TABLE VIII

1-BUTENE HYDROFORMYLATION IN THE PRESENCE OF VARIOUS TRIS(SILYL SUBSTITUTED ALKYL DIPHENYL PHOSPHINE) RHODIUM CARBONYL HYDRIDE COMPLEX CATALYSTS

Catalyst: $L_3Rh(CO)H$, Rh = 107 ppm, Rh/L = 140
Pressure: 350 psi (26 Atm)

| Seq. No.* | Ligand Structure, L | Example No. of Complex | Reaction Temp. °C. | $H_2/CO$ Ratios Initial | $H_2/CO$ Ratios Feed | $H_2/CO$ Ratios Final | Rate Constant k, min$^{-1}$ | Fraction of $H_2/CO$ Reacted Conversion % | Reaction Time Min. | Ratio n/i | %, 100n n+i | Selectivity to Aldehyde Products, % n | Selectivity to Aldehyde Products, % i | Selectivity to By-Products, % Butane | Selectivity to By-Products, % 2-Butene |
|---|---|---|---|---|---|---|---|---|---|---|---|---|---|---|---|
| 1a | $Ph_2PCH_2CH_2Si(C_3H_7)_3$ | 50 | 120 | 5 | 1.08 | 3.6 | 0.072 | 80 | 30 | 8.90 | 89.9 | 63.4 | 7.1 | 20.2 | 9.3 |
| 1b | $Ph_2PCH_2CH_2Si(C_3H_7)_3$ | 50 | 145 | 5 | 1.27 | 3.8 | 0.274 | 80 | 8 | 9.62 | 90.6 | 61.1 | 6.4 | 18.4 | 14.3 |
| 2 | $Ph_2PCH_2CH_2SiPh_3$ | 51 | 145 | 5 | 1.27 | 7.1 | 0.132 | 80 | 30 | 7.59 | 88.4 | 73.6 | 9.7 | 8.3 | 8.3 |
| 3 | $[Ph_2PCH_2CH_2]_2Si(CH_3)_2$ | 52 | 145 | ~4 | ~1 | — | 0.157 | 80 | 12 | 7.6 | 88.4 | — | — | — | — |
| 4a | $Ph_2PCH_2CH_2CH_2Si(CH_3)_3$ | 53 | 120 | 5 | 1.03 | 3.7 | 0.069 | 81 | 34 | 8.34 | 89.3 | 69.9 | 8.4 | 13.2 | 8.5 |
| 4b | $Ph_2PCH_2CH_2CH_2Si(CH_3)_3$ | 53 | 145 | 4 | ~1 | 2.3 | 0.260 | 82 | 9 | 5.80 | 85.3 | 67.6 | 11.7 | 10.9 | 9.8 |
| 5 | $Ph_2PCH_2Si(CH_3)_3$ | 54 | 100 | 5 | 1.05 | 5 | 0.056 | 78 | 60 | 6.24 | 86.2 | 54.3 | 8.1 | 31.8 | 5.9 |

*Experiments of Seq. No. 1a and 1b were carried out in 2-ethylhexyl acetate as a solvent. The rest were in 2-propylheptyl valerate.

EXAMPLE 44

Hydroformylation with the Tris-(Trimethylsilylethyl Diphenyl Phosphine) Rhodium Complex System at High Concentrations of Excess Ligand at 145° C.

The effect of very high concentrations of excess phosphine ligands on rhodium catalyst stability and selectivity was examined in a comparative study of the TPP and SEP systems. The study was carried out at an approximate $H_2/CO$ ratio of 5 to 1, with feed gas introduction into the stirred catalyst solution (Method C) at 145° C. At this temperature the TPP rhodium complex system is unstable at low excess phosphine concentration.

It should be noted that at low phosphine concentrations, e.g., 0.14 M, the n/i ratio of the products is much lower when using the present procedure than the n/i ratios observed in previous examples. As discussed earlier, lower n/i ratios result when CO starvation is eliminated.

The results of comparative experiments with TPP and SEP are shown in Table IX. The molar concentrations of both ligands in the reaction mixture range widely from about 0.14 to 3. This meant that the weight ratio of the 2-ethylhexyl acetate solvent to the phosphine ligand in the starting catalyst solution was decreased from about 20 to 0. In the extreme, the phosphine ligand was the solvent in both cases.

TABLE IX

HYDROFORMULATION OF 1-BUTENE WITH TRIS-PHOSPHINE RHODIUM CARBONYL HYDRIDE CATALYST IN THE PRESENCE OF INCREASING TPP AND SEP LIGAND EXCESS

Reactions at 145°, 350 psi (24.7 Atm) of 5/1 $H_2CO$ (54/46 $H_2/CO$)
Feed and 20 g 1-Butene Plus 80 g Mixture of Phosphine Plus
2-Ethylhexyl Acetate, using Acac $Rh(CO)_2$ as catalyst Precursor and
Introducing the Feed Gas into the Stirred Reaction Mixture

| [Ligand,L] Seq. No. | Run No. | Catalyst System Parameters L Concentration M in Mix. at Start | Catalyst System Parameters L Concentration % Weight in Solvent | Catalyst System Parameters Rh Conc. $10^3 \times$ M | L/Rh | $H_2/CO$ Consumption Dependent Factors (50% Conversion) $H_2/CO$ Final | $H_2/CO$ Consumption Dependent Factors (50% Conversion) Rate Constant k, min$^{-1}$ | $H_2/CO$ Consumption Dependent Factors (50% Conversion) Reaction Time min. | Aldehyde Product Parameters Linearity n/i Ratio | Aldehyde Product Parameters Linearity $n \times 100$ n+1 % | Aldehyde Product Parameters Hydroformylation Selectivity Total n+1 % | Aldehyde Product Parameters Hydroformylation Selectivity n- % | Aldehyde Product Parameters Hydroformylation Selectivity i- % | By-Product Selectivity, % 2-Butenes | By-Product Selectivity, % Butane |
|---|---|---|---|---|---|---|---|---|---|---|---|---|---|---|---|
| I: $\phi_3P$ | | | | | | | | | | | | | | | |
| 1 | 681 | 0.14 | 4.7 | 0.5 | 280 | 5.3 | 0.34 | 2.25 | 4.4 | 81.5 | 81.8 | 66.7 | 15.1 | 13.0 | 5.2 |
| 2 | 772 | 0.56 | 18.5 | 2 | 280 | 4.9 | 0.57$^a$ | 1.5 | 7.2 | 87.8 | 80.0 | 70.3 | 9.7 | 14.0 | 5.9 |
| 3 | 724 | 0.56 | 18.5 | 0.25 | 2240 | 3.1 | 0.08 | 9.0 | 7.6 | 88.4 | 82.3 | 73.5 | 9.7 | 11.7 | 5.1 |
| 4 | 771 | 1.00 | 32.9 | 2 | 500 | 5.2 | 0.44$^a$ | 2.0 | 11.1 | 91.7 | 82.1 | 75.3 | 6.8 | 12.7 | 5.3 |
| 5a | 796 | 2.20 | 72.1 | 2 | 1100 | 5.2 | 0.18 | 4.0 | 21.5 | 95.0 | 81.0 | 77.4 | 3.6 | 13.5 | 5.5 |
| 5b | 824 | 2.20 | 72.1 | 0.5 | 4400 | 7.2 | 0.07$^a$ | 11 | 18.1 | 94.8 | 90.3 | 85.6 | 4.7 | 7.1 | 2.6 |
| 6 | 774 | 3.00 | 100 | 2 | 1500 | 3.6 | 0.096 | 9.5 | 31.0 | 96.9 | 73.3 | 71.0 | 2.3 | 19.6 | 7.1 |
| II: $\phi_2PC_2H_4SiMe_3$ | | | | | | | | | | | | | | | |
| 1 | 711 | 0.14 | 5.0 | 0.5 | 280 | 5.4 | 0.18 | 4.0 | 5.1 | 83.5 | 86.2 | 72.0 | 14.2 | 7.6 | 6.2 |
| 2b | 807 | 0.56 | 20.0 | 2 | 280 | 6.0 | 0.21 | 3.5 | 9.9 | 90.9 | 86.1 | 78.2 | 7.9 | 8.2 | 5.7 |
| 3b | 802 | 1.00 | 35.9 | 2 | 500 | 5.9 | 0.14 | 5.0 | 11.7 | 92.1 | 86.4 | 79.6 | 6.8 | 7.4 | 6.2 |
| 4 | 803 | 2.20 | 78.7 | 2 | 1100 | 5.6 | 0.07 | 9.5 | 15.1 | 93.8 | 84.0 | 78.8 | 5.2 | 9.1 | 6.9 |
| 7 | 805 | 2.80 | 100 | 2 | 1400 | 5.6 | 0.05 | 15.0 | 20.1 | 95.2 | 82.8 | 78.9 | 3.9 | 9.1 | 8.0 |

$^a$The reaction rate was decreasing with increasing conversion.

With few exceptions, all the reaction mixtures had the same rhodium concentration, $2 \times 10^{-3}$ M. In the case of both TPP and SEP, the reaction rate decreased with increasing ligand concentration. The rate had decreased to about one third of the original as the ligand concentration quadrupled from 0.56 to 2.2 M. The rate of the TPP complex catalyzed reactions was about three times greater than those of the SEP catalyzed reactions. In fact, several of the TPP runs were too fast for a reliable control of the reaction conditions. In spite of this, the reaction rates were well maintained in most of the TPP mixtures. All of the SEP mixtures showed the same rate during the reaction, up to 50% conversion.

The n/i ratio of the aldehyde products strongly depended on the phosphine excess in both cases. Although the P/Rh ratio was kept constant when increasing the ligand concentration from 0.14 to 0.56, the n/i ratio almost doubled for both TPP and SEP.

The selectivity for n-plus i-aldehydes stayed about the same in both cases when the phosphine concentration was between 0.14 and 2.2. The total aldehydes were about 82% for TPP and about 86% for SEP. However, it appeared that the total aldehyde selectivity decreased in both cases when the ligand was the only added solvent. The use of TPP as a solvent led to a drastic decrease, i.e., to about 71% total aldehydes. When SEP was the solvent, a minor decrease to about 83% aldehydes was observed.

The selectivity of 1-butene conversion to the 2-butenes and n-butane by-products was, of course, inversely proportional to the selectivity for total aldehydes. In general, the use of the TPP system resulted in more undesired 1-butene isomerization to 2-butenes, about 12% versus about 8%. However, the selectivity of some of the TPP systems were adversely affected by the extremely high reaction rates which results in some CO starvation of such mixtures.

Overall, it appears that for both the TPP and the SEP based catalyst systems there is an optimum concentration. This concentration is rather high. It is in the 1 to 2.2 M range. This corresponds to a 33 to 79 weight % range. In other words, under these conditions, it appears preferable to operate in catalyst solution having the phosphine as the major component.

EXAMPLE 45

Hydroformylation with Bis-(Diphenylphosphinopropyl) Dimethyl Silane, i.e., BDS, Rhodium Complex System at Increasing Concentrations of Excess Ligand and Increased CO Partial Pressure Two series of experiments were carried out using the BDS bis-phosphine ligand of Example 4 for the rhodium hydroformylation of 1-butene with Method C. In the first series to tests (Seq. Nos. 1-5) the hydroformylations were carried out at 145° C. using starting reaction mixtures of increasing phosphorus equivalency, in the 0.14 to 2.2 $\bar{N}$ range (Table X, A). The second series of tests (Seq. Nos. 6-12) were carried out in the presence of high concentrations of BDS, at increasing temperatures and CO partial pressure (Table X, B).

The results of the first series of tests (Seq. Nos. 1-5) showed that the increased BDS concentration resulted in increased selectivities for n-versus i-aldehyde. However, at the same rhodium concentration, the increased BDS excess adversely affected the reaction rate. The results of the second series of Tests (Seq. Nos. 6-12) showed that, at the high BDS concentration, active hydroformylations can be carried out at temperatures up to 170° C. Surprisingly, increased CO partial pressures resulted in decreased hydroformylation rates and increased activities for total aldehydes under these conditions (Seq.

TABLE X

Hydroformylation of 1-Butene with Tris-Phosphine Rhodium Carbonyl Hydride Catalyst
Using Bis-(Diphenylphosphinoethyl) Dimethyl Silane (BDS) Ligand
Reactions with 20 g 1-butene and 80 g of phosphine plus 2-ethylhexyl acetate solvent, using AcacRh(CO$_2$)
as catalyst precursor and introducing the feed gas into the stirred reaction mixture.

| Experiment | | | Catalyst System Parameters | | | | | H$_2$/CO Consumption Dependant Factors (50% Conversion) | | | |
|---|---|---|---|---|---|---|---|---|---|---|---|
| Seq. No. | Run No. | Temp. °C. | $\bar{N}^a$ in Mix at start | Rh Conc mM̄ | P$^b$/Rh | Total Pressure (psi) | Approx Pco (psi) | Feed Ratio H$_2$/CO | H$_2$/CO Ratio Initial | Final | Rate Constant Kg min$^{-1}$ | Rxn time min. |
| 1 | 202 | 145 | 0.14 | 0.25 | 560 | 350 | 60 | 54/46 | 5.1 | 6.4 | 0.052 | 15 |
| 2 | 196 | 145 | 0.56 | 0.50 | 1120 | 350 | 60 | 54/46 | 5.1 | 7.2 | 0.038 | 19 |
| 3 | 194 | 145 | 1.00 | 0.50 | 2000 | 350 | 60 | 54/46 | 5.0 | 5.5 | 0.025 | 28 |
| 4 | 75 | 145 | 1.50 | 1.0 | 1500 | 350 | 60 | 54/46 | 5.5 | 5.7 | 0.040 | 16 |
| 5 | 197 | 145 | 2.20 | 1.0 | 2200 | 350 | 60 | 54/46 | 5.1 | 5.5 | 0.025 | 28 |
| 6 | 200 | 155 | 1.50 | 0.50 | 3000 | 350 | 60 | 54/46 | 5.0 | 5.5 | 0.030 | 23 |
| 7 | 203 | 155 | 1.50 | 0.50 | 3000 | 700 | 120 | 54/46 | 5.0 | 5.7 | 0.035 | 19 |
| 8 | 201 | 170 | 1.50 | 0.25 | 6000 | 350 | 60 | 56/44 | 5.0 | 5.1 | 0.021 | 30 |
| 9 | 207 | 170 | 1.50 | 0.25 | 6000 | 700 | 120 | 56/44 | 4.9 | 6.5 | 0.033 | 23 |
| 10 | 208 | 170 | 1.50 | 0.25 | 6000 | 700 | 280 | 51/49 | 1.5 | 1.7 | 0.044 | 16 |
| 11 | 216 | 170 | 2.20 | 0.50 | 4400 | 700 | 120 | 56/44 | 5.0 | 5.8 | 0.047 | 17 |
| 12 | 214 | 170 | 2.20 | 0.25 | 8800 | 700 | 280 | 51/49 | 1.5 | 1.5 | 0.014 | 60 |

| Experiment | | Aldehyde Product Parameters | | | | | | |
|---|---|---|---|---|---|---|---|---|
| | | Linearity | | Hydroformylation Selectivity | | | By-product Selectivity, % | |
| Seq. No. | Run No. | n/i Ratio | n × 100 / n + i % | n + i % | n- % | i- % | 2-Butenes | Butane |
| 1 | 202 | 6.49 | 86.7 | 89.2 | 77.3 | 11.9 | 7.5 | 3.3 |
| 2 | 196 | 10.95 | 91.6 | 88.9 | 81.5 | 7.4 | 7.4 | 3.7 |
| 3 | 194 | 11.89 | 92.2 | 88.7 | 81.8 | 6.9 | 7.8 | 3.5 |
| 4 | 75 | 13.38 | 93.2 | 89.4 | 83.4 | 6.1 | 7.0 | 3.6 |
| 5 | 197 | 16.60 | 94.3 | 93.5 | 88.2 | 5.3 | 4.5 | 2.0 |
| 6 | 200 | 14.44 | 93.5 | 85.7 | 80.2 | 5.6 | 9.6 | 4.7 |
| 7 | 203 | 9.24 | 90.2 | 91.3 | 82.4 | 8.9 | 6.8 | 2.9 |
| 8 | 201 | 11.49 | 92.0 | 80.4 | 74.0 | 6.4 | 13.3 | 6.3 |
| 9 | 207 | 9.71 | 90.7 | 88.0 | 79.8 | 8.2 | 7.4 | 4.6 |
| 10 | 208 | 5.79 | 85.3 | 93.0 | 79.3 | 13.7 | 5.3 | 1.7 |
| 11 | 216 | 10.09 | 91.0 | 87.3 | 79.5 | 7.9 | 6.7 | 5.0 |

TABLE X-continued

Hydroformylation of 1-Butene with Tris-Phosphine Rhodium Carbonyl Hydride Catalyst
Using Bis-(Diphenylphosphinoethyl) Dimethyl Silane (BDS) Ligand
Reactions with 20 g 1-butene and 80 g of phosphine plus 2-ethylhexyl acetate solvent, using AcacRh(CO₂)
as catalyst precursor and introducing the feed gas into the stirred reaction mixture.

| | | | | | | | | |
|---|---|---|---|---|---|---|---|---|
| 12 | 214 | 6.42 | 86.5 | 93.9 | 81.2 | 12.7 | 4.8 | 1.3 |

[a]Phosphorus equivalent per kg of starting reaction mixture.
[b]Phosphorus to rhodium ratio.

Nos. 8–10). However, as expected, the n/i ratio of aldehydes decreased by increasing CO partial pressure. Another, non-chelating bis-phosphine ligand bis-(diphenylphosphinopropyl) dimethyl silane was also studied at high concentration in rhodium hydroformylation in a similar manner. The results again showed a highly active production of n-valeraldehyde from 1-butene.

EXAMPLE 46

Hydroformylation with the Rhodium Carbonyl Hydride Complex of Tris-(Diphenylphosphinoethyl) Methyl Silane, TDS and Tetrakis-(Diphenylphosphinoethyl) Silane The rhodium hydroformylation of 1-butene at 145° C. in the presence of the non-chelating tris-phosphine of Example 9 was also studied under the standard conditions of the previous examples using Method C. The TDS ligand was present at the 0.14 and 1.0 phosphorus equivalent per kg reaction mixture concentration. The $H_2/CO$ ratio was held at about 5 to 1.

At the low TDS concentration, a n/i ratio of about 7.3 was obtained, i.e., an exceptionally high value. At the higher ligand concentration, the n/i ratio was about 10.1, a typical value for silylalkyl diaryl phosphine rhodium complex systems under these conditions.

The rhodium complex of the tetrakis-(diphenylphosphinoethyl) silane was even more unique in leading high n/i ratio of aldehyde products at relatively low P/Rh ratios. This behavior is probably due to the steric crowding of the starting tetra-phosphine ligand, described in Example 10, and its complex derivatives.

EXAMPLE 47

Hydroformylation with Tris-Phosphine Rhodium Carbonyl Hydride Systems Having Different Ratios of the TPP and SEP Ligands at a Total of 1 M Phosphine Concentration at 145° C.

The hydroformylation of 1-butene was also studied using Method C at a 1 M phosphine concentration under the standard conditions of the previous examples using TPP/SEP mixtures. The results are shown by Table XI.

In general, the data of Table XI show that the n/i ratio of the aldehyde products showed very little of any dependence on the TPP/SEP ratio. However, as the mole percentage of SEP in the total phosphine ligand has increased the amount of the total aldehyde (n+i) was also increased.

It is interesting to observe that the use of 10 mole % SEP produces quite a significant increase in the total selectivity to aldehydes (Seq. No. 2). The increased selectivity to n+i aldehydes was maintained when the SEP content of the phosphine ligand was increased to 20 mole %. Surprisingly, no significant decrease of the rate of hydroformylation has occurred up to this point. The use of further increased amounts of SEP resulted in further increased total aldehyde selectivity and also in reduced hydroformylation rate as expected.

Overall, the data indicate that TPP-SEP mixtures, containing 10 to 90, preferably 20 to 90 mole %, SEP, are unexpectedly advantageous hydroformylation catalyst systems, presumably due to the preferential complexation of SEP with rhodium. The weight percentage of SEP in these mixtures is most preferably between about 25 to 50%. Similar preferred molar ratios and weight percentages apply to mixtures of alkyl diaryl phosphines and triaryl phosphines, in general.

TABLE XI

1-BUTENE HYDROFORMYLATION WITH TRIS-PHOSPHINE RHODIUM COMPLEX SYSTEMS HAVING VARYING RATIOS OF TPP AND DTS LIGANDS
Reaction at 145° C., 350 psi (24.7 Atm) of 5/1 $H_1/CO$ reactant, 20 g 1-Butene Feed, 1 M Total Phosphine in 2-Ethylhexyl Acetate, 0.5 mM Rh as AcacRh(CO)₂ Catalyst Precursor, Introducing 54/46 $H_2/CO$ Feed Gas into Reaction Added Mixture

| | | Catalyst System Parameters | | | $H_2/CO$ Consumption Dependent Factors (50% Conversion) | | Aldehyde Product Parameters | | | | | By-Product Selectivity, % | |
|---|---|---|---|---|---|---|---|---|---|---|---|---|---|
| | | Phosphine Component Mole % | | SEP to Rh Ratio | $H_2/CO$ Final | Rate Constant k, min⁻¹ | Reaction Time min. | Linearity | | Hydroformylation Selectivity | | | |
| Seq. No. | Run No. | TPP | SEP | | | | | n/i Ratio | n × 100 n + i % | Total n + i % | n- % | i- % | 2-Butenes | Butane |
| 1 | 9 | 100 | — | — | 6.5 | 0.10 | 7 | 12.3 | 92.5 | 80.8 | 74.7 | 6.1 | 13.6 | 5.6 |
| 2 | 16 | 100 | — | — | 5.7 | 0.05[a] | 14 | 11.2 | 91.8 | 81.2 | 74.6 | 6.7 | 13.3 | 5.5 |
| 3 | 10 | 98 | 2 | 40 | 6.9 | 0.10 | 7 | 12.5 | 92.6 | 81.1 | 75.1 | 6.0 | 13.2 | 5.6 |
| 4 | 12 | 90 | 10 | 200 | 6.3 | 0.09 | 8 | 13.0 | 92.9 | 84.0 | 78.0 | 6.0 | 10.6 | 5.4 |
| 5 | 23 | 80 | 20 | 400 | 5.9 | 0.07 | 10 | 12.6 | 97.7 | 83.8 | 77.7 | 6.2 | 10.3 | 5.9 |
| 6 | 14 | 50 | 50 | 1000 | 6.6 | 0.04 | 16 | 13.3 | 93.0 | 88.2 | 82.0 | 6.2 | 7.3 | 4.6 |
| 7 | 15 | 10 | 90 | 1800 | 7.0 | 0.03 | 21 | 12.5 | 92.6 | 88.3 | 81.8 | 6.5 | 7.1 | 4.6 |
| 8 | 923 | — | 100 | 2000 | 6.5 | 0.03 | 22 | 11.8 | 92.2 | 88.3 | 81.4 | 6.9 | 7.1 | 4.7 |

[a][Rh] = 0.25 mM

Similar results were obtained using similar mixtures of bis-(diphenylphosphinoethyl) dimethyl silane, BDS, and TPP. A mixture of 20 phosphorus equivalent BDS and 80 phosphorus equivalent TPP led to a n/i ratio of about 12 and a total aldehyde selectivity of 86.6%.

EXAMPLE 48

Hydroformylation with SEP Rhodium Complex System Using a Concurrent Addition of 1-Butene and $H_2/CO$ To explore the potential effect of minimal 1-butene concentration during the reaction on the selectivity a hydroformylation experiment was carried out under the conditions of the previous experiment but with a slow introduction of the 1-butene reactant. The SEP ligand was used in one molar concentration with Method C. However, 1-butene addition was started only after the catalyst mixture was reached reaction condition, i.e., 145° C. and 350 psi. The 1-butene was introduced over the period of about one hour, concurrent with the $H_2/CO$ feed gas. A subsequent analysis of the reaction mixture showed substantially the same selectivity previously obtained when starting with an appropriate solution of 1-butene, and then subsequently feeding in the $H_2/Co$ feed gas.

Using a high L/Rh ratio, 1-pentene was selectively hydroformylated at 170° (Seq. No. 1). A lower L/Rh ratio was successfully used at 145° C. for the selective hydroformylation of 1-octene (Seq. No. 2).

A comparison of the n/i selectivities indicated that, in the absence of isomerization, 1-n-olefins of increasing carbon number react with increasing selectivity. Branching of terminal olefins further increased n/i

TABLE XII

HYDROFORMYLATION OF VARIOUS OLEFINIC COMPOUNDS IN THE PRESENCE OF SEP - RHODIUM COMPLEX BASED CATALYST SYSTEMS

Catalysts: $L_3Rh(CO)H$; L = SEP = $Ph_2PCH_2CH_2Si(CH_3)_3$; Precursor: Dicarbonyl Acetylacetonato Rhodium; Total Pressure 350 psi (~26 Atm) Solvent: 2-Ethylhexyl Acetate

| Seq. No. | Olefinic Reactant | Rh Conc., ppm | L/Rh | Reaction Temp., °C. | $H_2/CO$ Ratio Initial | Feed | Final | Rate Constant k, min$^{-1}$ | Fraction of $H_2/CO$ Reacted Conversion % | Reaction Time, Min. | Aldehyde Product Linearity Ratio n/i | %, 100n/(n+i) | Selectivities to Various Compounds Aldehydes n | i | Butane | 2-Butenes |
|---|---|---|---|---|---|---|---|---|---|---|---|---|---|---|---|---|
| 1 | 1-Pentene | 105 | 510 | 170 | 5.0 | 117 | 3.0 | 0.193 | 80 | 12 | 7.5 | 88.2 | 53.3 | 7.1 | 19.3 | 20.2 |
| 2 | 1-Octene | 113 | 98 | 145 | 4.0 | 1.04 | | 0.257 | 80 | 8 | 6.8 | 87.2 | | | | |
| 3 | | | 141 | 165 | 4.0 | 1.04 | | 0.521 | 80 | 4 | 5.9 | 85.5 | | | | |
| 4 | 3-Methyl-butene | 110 | 140 | 145 | 5.0 | 1.27 | 6.6 | 0.274 | 81 | 10 | 23.9 | 96.0 | 70.8 | 3.0 | 25.2 | 0 |
| 5* | Cis-2-Butene | 447 | 256 | 170 | 5.0 | 1.27 | 3.6 | 0.018 | 80 | 150 | 1.0 | 49.5 | 38.7 | 41.4 | 6.1 | |
| 6** | 2-Ethylhexene | 553 | 28 | 120 | 1.08 | 1.08 | 1.45 | 0.007 | 40 | 135 | ∞ | 100 | 100 | Nil | Nil | Nil |
| 7** | Diallyl Ether | 112 | 140 | 120 | 5.0 | 1.08 | 31 | 0.434 | 80 | 5.5 | 3.6 | 78.3 | | | | |

*There was a 2.6% selectivity to amyl alcohols. Both mono and bis-hydroformylated products were formed.
**Method B was used.

C. Hydroformylation of Other Olefinic Compounds (Example 48A-51)

EXAMPLE 48A

Hydroformylation of Propylene with the SEP Rhodium Complex System

The complex of Example 10 was studied at the 458 ppm rhodium level, in the presence of a one hundred fold excess of trimethylsilylethyl diphenyl phosphine ligand, as a propylene hydroformylation catalyst. The reaction temperature was 100°, the 1:4 $CO/H_2$ pressure was 400 psi. The general procedure previously employed for butene hydroformylation was used to carry out the reaction according to Method A.

The reaction rate was found to be k=0.04 min$^{-1}$, expressed as the fraction reacted. In 60 minutes, 82% conversion was reached based on the $CO/H_2$ consumed. The ratio of n-butyraldehyde to methylpropanal products was 5.0. The selectivity to these aldehydes was 87.5%. The selectivity to the by-product propane was only 2.5%.

EXAMPLE 49

Hydroformylation of Miscellaneous Olefinic Compounds with the SEP Rhodium Complex System In a series of experiments, summarized in Table XII, a number of olefins were hydroformylated using the tris-SEP complex based catalyst system (Seq. Nos. 1-7) under conditions of Method A.

selectivity. This is shown by the example of 3-methyl-butene (Seq. No. 4). Internal olefins could be also hydroformylated as shown in the case of cis-butene-2-hydroformylation (Seq. No. 5). It is important to note that isomerization to 1-butene also occurred as indicated by the formation of n-valeraldehyde.

A terminal olefin having a substituent on a vinylic carbon, such as 2-ethylhexene showed an essentially specific terminal reaction to produce only the linear aldehyde derivative (Seq. No. 6).

Finally, an oxygenated diolefinic compound, diallyl ether, was also successfully hydroformylated without an apparent, major hydrogenation side reaction on (Seq. No. 7). Both the mono- and bis-hydroformylated products could be selectively produced. At low conversions, the primary unsaturated aldehyde products predominated. At high conversions, a high yield of the dialdehyde products was obtained. Other oxygenated compounds hydroformylated are allyl alcohol, allyl acetate, ethyl acrylate formaldehyde.

EXAMPLE 50

Hydroformylation of an Isomer Mixture of Pentenes with the SEP Rhodium System

Two exemplary hydroformylation experiments using a mixed pentenes feed are presented in Table XIII to show that all or certain components of olefin mixtures can be reacted. The conditions of Method A were used.

In the experiments shown by the table, the tris-SEP rhodium complex was used in the usual manner. However, no added solvent was employed.

The data show that the 1-n-olefin component (1-pentene) was the most reactive among the significant olefin components in both runs (Nos. 1 and 2). The minor branched olefin (3-methyl butene-1) was also highly

TABLE XIII

HYDROFORMYLATION OF MIXED PENTENES WITH TRIS-(TRIMETHYLSILYETHYL DIPHENYL PHOSPHINE) RHODIUM COMPLEX CATALYST SYSTEM

Catalyst: $L_3Rh(CO)H$, L = SEP, L/Rh, 139; Precursor: Dicarbonyl Acetylacetonato Rhodium; Olefin: 100 g Mixed Pentenes without Added Solvent

| | Reaction Conditions | | |
|---|---|---|---|
| Number | O: Feed | 1 | 2 |
| Temperature, °C. | | 120 | 120–145 |
| Time, Min. | | 300 | 360 |
| Olefin Conversion, % | | 30 | 55 |
| Rh Conc. ppm | | 109 | 293 |

| | Composition of Reaction Mixture | | | | |
|---|---|---|---|---|---|
| | Mole % | Mole % | Conv. % | Mole % | Conv. % |
| C₂ Hydrocarbons | | | | | |
| 3-Methylbutene | 0.31 | 0 | 100 | 0 | 100 |
| i-Pentane | 0.45 | 0.53 | — | 1.02 | — |
| 1-Pentene | 8.04 | 0.89 | 89 | 0.71 | 91 |
| 2-Methylbutene | 24.61 | 19.13 | 22 | 7.14 | 71 |
| n-Pentane | 4.14 | 5.10 | — | 6.10 | — |
| t-2-Pentene | 28.97 | 19.95 | 31 | 5.63 | 81 |
| c-2-Pentene | 12.32 | 7.35 | 40 | 2.19 | 82 |
| 2-Methylbutene-2 | 21.04 | 22.22 | 0 | 22.46 | 0 |
| Aldehydes | None | | | | |
| 2-Methylpentanal | — | 13.86 | | 27.33 | |
| 3-methylpentanal | — | 5.69 | | 16.97 | |
| 4-methylpentanal | — | — | | — | |
| n-hexanal | — | 5.27 | | 10.46 | | reactive. High conversions of the internal olefin components (cis- and trans-pentene-2's) and the olefinically substituted terminal olefin (2-methylbutene) could be also realized under the more forcing conditions of Run No. 2. It is noted that under the latter conditions some darkening of the reaction mixture occurred indicating some long term instability.

EXAMPLE 51

Hydroformylation 2-Butene with the SEP Cobalt Complex System

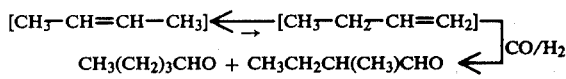

2-Butene was hydroformylated with a SEP complex of cobalt, presumably SEP tricarbonyl cobalt hydride, because cobalt compounds often catalyze olefin isomerization as well as hydroformylation. In the case of 2-butene, combined isomerization-hydroformylation is desired to obtain n-valeraldehyde via 1-butene.

As a precursor of the cobalt complex, dicobalt octacarbonyl was used in decane solution to provide a cobalt concentration of 0.2%. The SEP/Co ratio was 4. The main solvent was 2-ethylhexylacetate. About 20 g of the 2-butene reactant was used in the 100 g reaction mixture. The olefin was added at 175° C. The reaction was run at that temperature having 1/1 $H_2/CO$ initial gas followed by 52/48 run gas introduced at the bottom (Method C) of the mixture at a total pressure of 1000 psi (about 68 Atm) total pressure to a $CO/H_2$ consumption based conversion of 50% in 47 minutes.

An analysis of the reaction mixture by glc showed the formation of 38 mole % valeraldehydes of a n/i ratio of 5.2. About 15% of the two isomeric amyl alcohols of a n/i ratio of 13.4 were also formed. The mixture also contained 3.1 mole % 1-butene isomerization product and 3.3 mole % butane hydrogenation product.

D. Continuous Hydroformylation

EXAMPLE 52

Continuous Hydroformylation with the SEP and TPP Systems

The tris-(trimethylsilylethyl diphenyl phosphine) rhodium carbonyl hydride catalyst system was extensively studied in a continuous hydroformylation unit. The feed was butene-1 and the products were continuously removed together with the unreacted volatile components of the reaction mixture. The typical reaction temperature for the SEP based system was 120° C. Comparative runs were also carried out with a similar TPP based system at 100° C. Both systems could be successfully operated on the short run although it appeared that the known degradation reactions and the stripping of the valeraldehyde trimer by-product at 100° C. could become a problem with TPP. The SEP system showed an excellent long term stability and activity maintenance.

Figure 8:
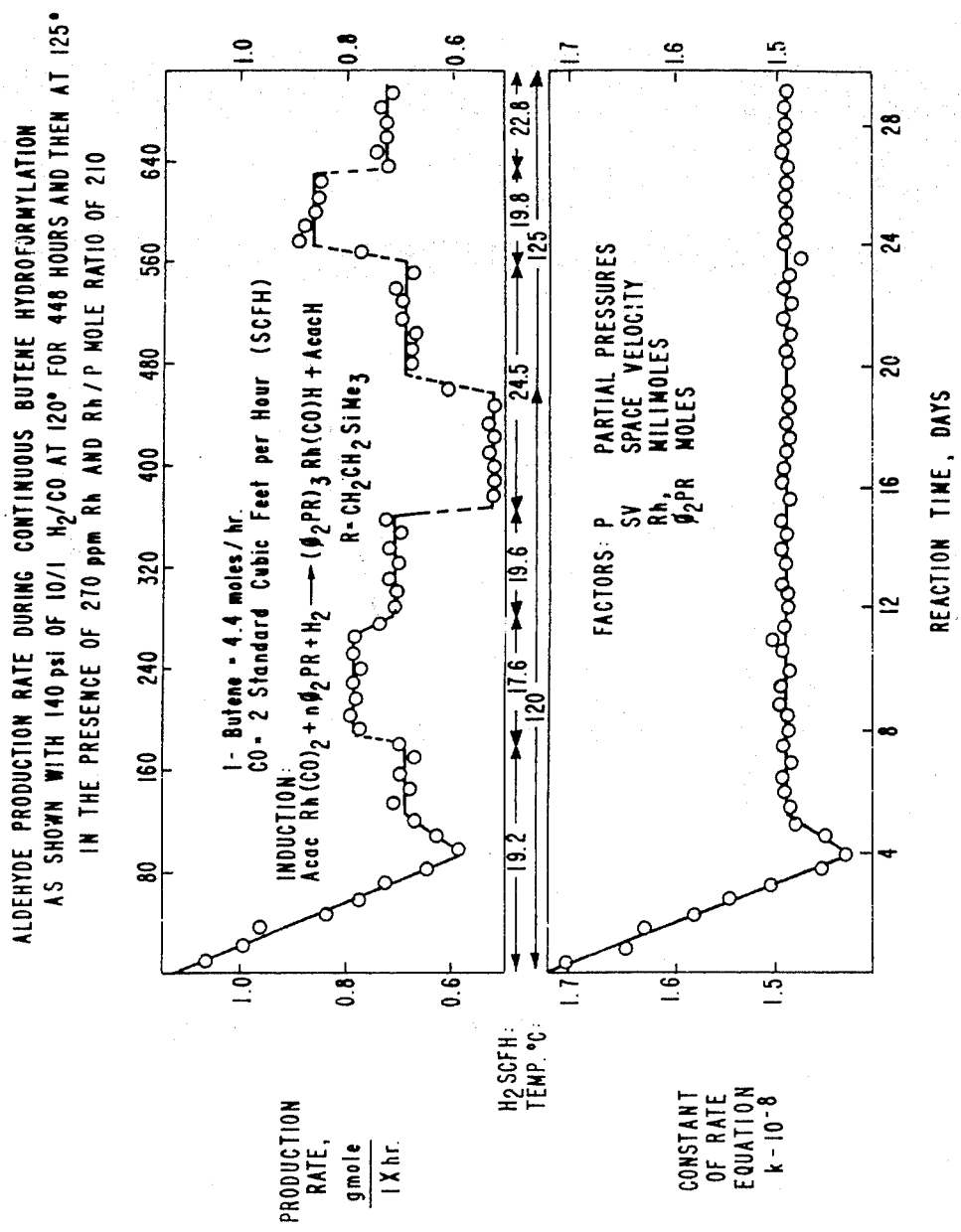
FIG. 8 shows the aldehyde production rate during continuous butene hydroformylation.

A representative 30 day continuous operation of the operation of the SEP catalyst system is illustrated by FIG. 8. With regard to the continuous operating conditions, it is noted that the total synthesis gas pressure was lower (125 psi, 8.5 Atm) and the $H_2/CO$ ratio higher (10/1) than in most of the batch studies. Also a higher concentration of rhodium (270 ppm) and a higher L/Rh ratio (210) were employed. Under these conditions a batch experiment produced results similar to those found in the continuous operation.

In the continuous hydroformylation the catalyst was generated from dicarbonyl acetylacetonato rhodium in situ. In a typical operation 1-butene was introduced into the reactor at a rate of 4.4 mole per hour. The rate of CO was typically 2 standard cubic feet per hour (SCFH). The hydrogen was introduced in the 15 to 25 SCFH range. By changing the hydrogen/CO ratio the aldehyde production rate and other parameters could be appropriately and reversibly controlled.

During the reaction isomeric valeraldehyde trimers and some tetramers were formed. At an equilibrium concentration they were in the concentration range from about 50 to 80% by wt.

After the reaction system came to an equilibrium, the rate of hydrogen gas feed introduction was decreased from 19.2 to 17.6 SCFH (standard cubic feet per hour; 1 SCFH=28.3 dm$^3$/hr) during the seventh day of the run. This resulted in an increased production rate. As expected, this process was fully reversible. Also, a increase of the synthesis gas feed rate above the initial level of 24.5 SCFH on the 15th day resulted in the expected decreased production rate.

On the nineteenth day, the reaction temperature was raised to 125° C. This resulted in an about 39% reaction rate increase as expected on the basis of an activation energy of 15.4 kcal. Subsequent changes of the space velocity of the synthesis gas feed at this higher temperature resulted in the expected reaction rate changes.

On the basis of the kinetic changes observed during the approximately 3 weeks of operation shown by the figure and on the basis of other continuous hydroformylations with the same catalyst system, a rate equation was developed. The rate equation did fit all the data. The rate constant remained unchanged after the startup equilibrium period for the 25 days shown. It is noted that the lack of change of the rate constant means that there is no loss of catalyst activity during this period. The only long term change in the catalyst system was some oxidation, probably by oxygen, of the phosphine ligand to the corresponding phosphine oxide. In the presence of excess phosphine, this oxidation had no adverse effect on the reaction rate. Combined gas chromatography and mass spectroscopy studies could not show any evidence of a ligand degradation similar to that reported to occur via o-phenylation in the TPP system.

EXAMPLE 53

Comparative Performance of Rhodium Complex Catalyst Systems based on SEP and TPP in Continuous Hydroformylation Operating with the SEP rhodium system at 120° C. hydroformylation selectivities could be obtained which were similar to those obtained at 100° C. with the TPP rhodium system. However, higher conversion could be realized with SEP. The comparative operational parameters and the selectivities to products and by-products obtained are shown in Table XIV.

The data of the table show that the most important parameters for high 1-butene conversion per pass are the reaction temperature and the stripping gas rate. These parametes control the rate of product flashoff. At the stripping gas rate of 38 g mole per hour per liter, a 38–50% 1-butene conversion was obtained when the thermally more stable SEP system was used at 120° C. The same stripping rate resulted in only 25–27% 1-butene conversion at 100° C. with the TPP system. This shows that the higher stability of the SEP system can be used to advantage in a high conversion process. The n/i ratio of the aldehydes and the selectivity to by-products are about the same for both catalyst systems.

TABLE XIV

COMPARATIVE PERFORMANCE OF RHODIUM COMPLEX SYSTEMS BASED ON SEP AND TPP IN CONTINUOUS 1-BUTENE HYDROFORMYLATION IN A PRODUCT FLASHOFF MODE

| | Rhodium Complex of | | |
|---|---|---|---|
| | SEP | SEP | TPP |
| Operating Parameters | | | |
| Temperature, °C. | 120 | 120 | 100 |
| Pressure, psia | 150 | 150 | 115 |
| 1-Butene feedrate, M/hr | 4.0 | 4.0 | 4.0 |
| H$_2$/CO ratio in feed | 7.5 | 8.0 | 7.5 |
| Rhodium, ppm | 260 | 480 | 260 |
| P/Rh ratio | 250 | 135 | 140 |
| Stripping gas rate, g mole/hr/liter | 26 | 38 | 38 |
| Conversion and Products | | | |
| 1-Butene conversion, % | 25–27 | 38–40 | 25–27 |
| Valeraldehyde production rate, m/hr/1 | 1.0–1.1 | 1.4–1.5 | 1.0–1.1 |
| n/i Aldehyde ratio | 20–25 | 20–23 | 20–23 |
| Selectivity to By-Products | | | |
| Butane | 2–3 | 2–5 | 1–2 |
| 2-Butenes | 2–5 | 2–5 | 3–5 |
| Aldehyde dimers | 0.2 | 0.2 | 0.1 |
| Aldehyde trimers | 0.2–0.4 | 0.2–0.4 | 0.3 |

EXAMPLE 54

Continuous Hydroformylations Using 1-Butene and Mixed Butenes Feed at 145° C.

The SEP rhodium catalyst system was also employed for the continuous hydroformylation of 1-butene at 145° C. For maintaining catalyst selectivity and stability at this temperature, the ligand concentration was increased to 1 mole/liter. The rhodium concentration was also increased to 4.17 mmoles/liter to assure high olefin conversion per pass in a continuous product flash-off operation. The hydroformylation process was carried out under identical pressure, temperature and H$_2$/CO feed rate conditions, using a pure 1-butene feed at first for a period of six days, and then a mixture of 1- and 2-butenes for a subsequent six-day period. Details of the reaction conditions and results are shown by Table XV.

The pure and the mixed feeds were introduced at a different rate into the reactor to provide the 1-butene reactant at the same rate. In the case of the pure reactant, the performance was compared with that of the TPP-rhodium system.

A comparison of the data of Table XV shows that 1-butene was selectively hydroformylated to n-valeraldehyde regardless of the feed used. The selectivities were nearly identical. The stability of the SEP complex systems was excellent in both cases during the six day reaction period. The only change was due to the loss of some of the ligand by flash-off.

The comparative experiment with the TPP-rhodium system and 1-butene reactant showed ligand degradation. About ½% per day of butyl diphenyl phosphine was derived from the TPP in this system. This resulted in a significant activity loss during the reaction. Also, more C$_4$ by-products, particularly 2-butenes, were obtained.

TABLE XV

Continuous Hydroformylation of Mized n-Butenes and Pure 1-Butene Feed in a Product Flashoff Mode at 140° C. During a Six-Day Period All the reaction mixtures contain 1 P-equivalent/1 ligand, 4.17 mM/1 (460 ppm) rhodium complex (P/Rh = 240). The total pressure is 185 psi. The rate of feed introduction in mL is the following: $H_2$, 23.4; CO, 4.8 ($H_2$/CO 4.9)

|  | Rhodium Complex of | | | |
|---|---|---|---|---|
|  | SEP | SEP | TPP | BDS[b] |
| 1-Butene Reactant Employed | Mixture[a] | Pure | Pure | Pure |
| Reactant feed rate, 1-butene, m/hr | 2.75 | 2.75 | 2.75 | 2.75 |
| total feed, m/hr | 4.60 | 2.75 | 2.75 | 2.75 |
| Conversion and Selectivity | | | | |
| 1-Butene conversion, % | 56.1–51.8 | 57.4–54.8 | 82.1–65.5 | 57.0 |
| Total aldehydes, % | 82.8 | 85.2 | 77.9 | 85.5 |
| n/i aldehyde ratio | 13.1 | 12.3 | 11.7 | 14.4 |
| Selectivity to By-Products, % | | | | |
| Butane | 4.4 | 3.8 | 5.9 | 4.1 |
| 2-Butenes | 9.1 | 7.6 | 12.9 | 7.1 |
| Aldehyde dimers | 0.7 | 0.5 | 0.1 | 0.6 |
| Aldehyde trimers | 0.4 | 0.6 | 0.4 | 0.6 |
| Alcohols | 2.6 | 2.3 | 2.8 | 2.0 |

[a] The percentage composition of the reactant mixture is 1-butene, 59.6; 2-butenes, 31.0; n- and i-butanes, 6.8; i-butene, 1.4 and butadiene, 0.02; others, 1.1.
[b] Bis-(2-diphenylphosphinoethyl) dimethyl silane of Example 4.

A non-volatile silyl substituted bis-phosphine, bis-(2-diphenylphosphinoethyl) dimethyl silane, BDS based rhodium complex catalyst was also tested for 1-butene hydroformylation under the same conditions. As is shown by Table XV, the use of this ligand led to slightly improved but generally similar catalyst selectivities. However, the activity of the catalyst and the composition of the catalyst complex did not change whatsoever under the reaction conditions.

Combined Hydroformylation-Aldolization (Examples 55-58)

EXAMPLE 55

Combined Hydroformylation-Aldolization of 1-Butene at 120° C. in the Presence of Tris-(Trimethylsilylethyl) Diphenyl Phosphine [SEP] Rhodium Carbonyl Hydride Complex

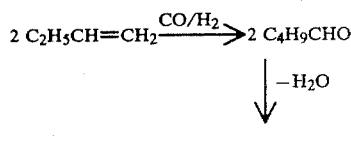

-continued $$C_4H_9CH=CCHO \xrightarrow{H_2} C_5H_{11}CHCO$$
$$\quad\quad\quad | \quad\quad\quad\quad\quad\quad\quad |$$
$$\quad\quad C_3H_7 \quad\quad\quad\quad\quad\quad C_3H_7$$

n,n-enal    n,n-anal

The combined hydroformylation, aldolization and hydrogenation of butene-1 was studied under typical conditions of the present hydroformylation process. The SEP rhodium complex was utilized as a typical substituted alkyl diaryl phosphine rhodium complex catalyst for hydroformylation and hydrogenation. Potassium hydroxide in methoxytriglycol was employed as an aldolization catalyst. The methoxytriglycol was also used as the solvent for the other components of the mixture. The catalyst system was employed at the 110 ppm rhodium concentration level. The ligand to rhodium ratio was 140. The 1-butene reactant was employed in a standard manner. The initial $H_2$/CO mixture used to pressure the mixture to 350 psi (25 atm) had a 5/1 mole ratio. The feed gas to maintain this pressure was a 1.5 to 1 mixture. The latter ratio was employed because it is theoretically needed to produce the n,n- and i,n-anals. The feed gas was introduced at the top of the reactor according to Method A.

The reaction and product parameters of a group of experiments designed to observe the effect of varying concentrations of KOH are summarized in Table XVI. The

TABLE XVI

Combined Hydroformylation-Aldolization of 1-Butene at 120° C. and 350 psi (~2 atm.) in the Presence of SEP Rhodium Complex and Varying Amounts of KOH SEP = L = $Ph_2PCH_2CH_2Si(CH_3)_3$; L/Rh = 140; Rh = 110 ppm

| Seq. No. | Run No. 7132 | KOH, % | $H_2$/CO Ratio | | | Fraction of $H_2$/CO Reacted | | Reaction Time Min. | Approx. Selectivities to Aldehydes Mole % | | | | n/i Ratio | % n, 100n n+1 | Selectivity to n-Butane mole % |
|---|---|---|---|---|---|---|---|---|---|---|---|---|---|---|---|
|  |  |  | Initial | Feed | Final | Rate Constant k, min$^{-1}$ | Conversion % |  | $C_5$'s i | $C_5$'s n | n,n(i)- anal | n,n- enal |  |  |  |
| 1 | 280 | Nil | 5 | 1.08 | 2.7 | 0.056 | 80 | 50 | 9.2 | 90.8 |  |  | 9.9 |  | 14.0 |
| 2 | 306 | Nil | 5 | 1.5 | 24.1 | 0.051 | 80 | 42 | 3.0 | 97.0 |  |  | 32.1 | 97.0 | 18.8 |
| 3 | 307 | Nil | 5 | 1.5 | 26.8 | 0.05 | 15 | 4 | 3.3 | 96.7 |  |  | 29.1 | 96.7 |  |

TABLE XVI-continued

Combined Hydroformylation-Aldolization of 1-Butene at 120° C. and 350 psi (~2 atm.) in the Presence of SEP Rhodium Complex and Varying Amounts of KOH SEP = L = $Ph_2PCH_2CH_2Si(CH_3)_3$; L/Rh = 140; Rh = 110 ppm

| Seq. No. | Run No. 7132 | KOH, % | $H_2/CO$ Ratio Initial | $H_2/CO$ Ratio Feed | $H_2/CO$ Ratio Final | Rate Constant k, min$^{-1}$ | Fraction of $H_2/CO$ Reacted Conversion % | Reaction Time Min. | $C_5$'s Mole % i | $C_5$'s Mole % n | n,n(i)-anal | n,n-enal | n/i Ratio | % n, 100n/(n+1) | Selectivity to n-Butane mole % |
|---|---|---|---|---|---|---|---|---|---|---|---|---|---|---|---|
| 4 | 286 | Nil | 5 | 1.50 | 21.3 | 0.042 | 80 | 48 | 3.1 | 96.9 | | | 31.5 | 96.9 | 15.1 |
| | | | | | | | 15 | 6 | 6.7 | 93.3 | | | 13.8 | | |
| | | | | | | | 45 | 15 | 5.8 | 94.2 | | | 16.3 | | |
| | | | | | | | 60 | 24 | 5.5 | 34.5 | | | 17.2 | | |
| | | | | | | | 80 | 80 | 6.2 | 93.8 | | | 15.0 | 93.8 | 17.7 |
| 5 | 283 | 0.05 | 5 | 1.50 | 47 | 0.059 | 80 | 34 | 4.1 | 47.5 | 8.4 | 40.0 | 34.9 | 97.2 | 28.9 |
| 6 | 285 | 0.05 | 5 | 1.50 | 17.7 | 0.061 | 15 | 4 | 6.1 | 81.6 | 0.8 | 11.7 | 17.6 | 94.6 | |
| | | | | | | | 30 | 18 | 5.5 | 76.8 | 1.0 | 16.7 | 20.5 | 95.4 | |
| | | | | | | | 45 | 11 | 5.4 | 72.9 | 1.5 | 20.2 | 21.6 | 95.6 | |
| | | | | | | | 60 | 16 | 5.2 | 67.3 | 2.7 | 24.7 | 23.5 | 95.9 | |
| | | | | | | | 80 | 30 | 5.9 | 51.5 | 7.8 | 34.8 | 23.2 | 95.9 | 17.7 |
| 7 | 301 | 0.10 | 5 | 1.17 | 6.52 | 0.062 | 15 | 5 | 2.9 | 17.8 | 3.0 | 50.2 | 42.9 | 94.3 | |
| | | | | | | | 80 | 32 | 9.3 | 34.1 | 13.0 | 43.6 | 15.8 | 77.1 | 15.0 |
| 8 | 281 | 0.10 | 5 | 1.50 | 5.0 | 0.048 | 80 | 42 | 3.4 | 27.1 | 18.3 | 51.2 | 49.2 | 98.0 | 31.3 |
| 9 | 279 | 0.20 | 5 | 1.50 | 5.0 | 0.043 | 80 | 40 | 2.9 | 16.0 | 16.0 | 65.2 | 60.5 | 98.4 | 28.8 |
| 10 | 288 | 0.20 | 5 | 1.50 | 13.6 | 0.049 | 15 | 3 | — | — | 10.8 | 89.2 | ∞ | — | |
| | | | | | | 0.028 | 30 | 5 | 3.7 | — | 11.5 | 84.9 | 50.6 | 98.0 | |
| | | | | | | | 45 | 12 | 3.0 | — | 12.0 | 85.0 | 64.4 | 98.5 | |
| | | | | | | | 60 | 16 | 3.3 | 7.5 | 13.6 | 75.8 | 57.1 | 98.3 | |
| | | | | | | | 80 | 32 | 3.6 | 17.7 | 18.6 | 60.1 | 48.0 | 98.0 | |
| | | | | | | | 92 | 62 | 4.9 | 14.1 | 34.5 | 46.5 | 35.9 | 97.3 | 16.0 | product parameters, i.e., selectivities to the various products were obtained by glc analyses. For the analyses of the $C_5$ and $C_{10}$ aldehydes, a special 2m Carbowax column 10% CW on Chromosorb P diatomaceous earth was used. This was provided by Supelco, Inc., Supelco Park, PA. It provided good separation of the n,n-enal was not good. The small quantities of the i,n-enal formed could not be determined. Therefore, the overall n,i-ratios in the reaction mixtures with KOH could not be exactly determined. The aldehyde selectivity to the main final $C_{10}$ aldehyde products, the n,n-enal, also includes minor quantities of the i,n-anal. However, this inclusion causes less than 10% change in the composition, since the minor i-$C_5$ aldehyde is cross-aldolized at a very slow rate. The glc percentages are indicated on the basis of the peak intensities. No corrections were made for the possibly different glc response to $C_5$ and $C_{10}$ compounds.

In the first four experiments, the hydroformylation of butene was studied in methoxytriglycol but in the absence of KOH aldolization catalyst (Seq. Nos. 1 to 4), for comparison. All three experiments started with 5/1 $H_2/CO$ gas. In the first experiment, the $H_2/CO$ ratio of the feed gas was close to one as usual. This experiment gave the usual high n/i ratio of $C_5$ aldehydes. This indicated that the solvent is an acceptable one.

The rest of the experiments used the same initial $H_2/CO$ ratio of 5 but a different $H_2/CO$ feed of 1.5. Also, the contents of the third and fourth reaction mixture were sampled for comparison with the experiments using added KOH. This and other sampled runs provided less reliable absolute values than the uninterrupted experiments. However, they gave comparative relative numbers which showed the change of selectivity with the increasing conversion.

The second experiment (Seq. No. 2) showed a much increased n/i ratio compared to the first. This was the consequence of the increasing $H_2/CO$ ratio, i.e., decreasing CO partial pressure due in the reaction. Due to decreased availability of CO, this run also resulted in more hydrogenation of the 1-butene starting material and isomerized 2-butenes to n-butane.

The results of the first sampled experiment are somewhat similar. This experiment shows that as a consequence of increasing $H_2/CO$ ratio, the selectivity is much higher at 80% conversion (Seq. No. 3).

The fourth experiment (Seq. No. 4) was sampled four times during the run. It showed that up to 60% conversion, the n/i ratio was moderately increasing as an apparent consequence of the increasing $H_2/CO$ ratio in the reaction mixture.

The second group of experiments (Seq. Nos. 5–10) was run using varying amounts of KOH, in the 0.05 to 0.2% range, under the same conditions. The data indicated that 0.2% KOH was sufficient for the rapid conversion of the primary n-$C_5$ aldehyde product eq. Nos. 7 and 8). The aldolization rate was much slower when 0.05% KOH was used (Seq. Nos. 5 and 6). The rate of the hydroformylation was estimated on the basis of the measured rate of synthesis gas consumption.

Increasing $H_2/CO$ ratios generally resulted in increased n/i ratios and increased percentages of n-butane formation. Due to apparent CO starvation, the non-sampled mixtures gave rise to significantly higher $H_2/CO$ ratios than those frequently sampled during the run.

The hydrogenation of the unsaturated aldehyde to the saturated aldehyde was relatively low. At 45% synthesis gas conversion, the percentage n,n-anal formed was less than 10% of the n,n-enal present. At that conversion, the overall selectivity to the n,n-enal was in excess of 80%.

EXAMPLE 56

Sequential Hydroformylation, Aldolization, Hydrogenation in Separate Steps

In a series of experiments, n-valeraldehyde was produced by the hydroformylation of B 1-butene and separated from the i-isomer. A 20% methoxytriglycol solution of the n-valeraldehyde was then aldolized to provide the n,n-enal condensation product. It was observed that the aldolization was much slower in the absence of the hydroformylation catalyst system in the presence of it in the previous example. After 30 minutes reaction time, only a 1.2% conversion was reached. After 14 hours, the aldehyde conversion was 47.2%, i.e., the concentration of the n,n-enal in mole equivalents was 47.2%.

During the above experiment, and other experiments with KOH solutions in methoxytriglycol, yellow, then amber, then brown color formation was observed indicating potential instability. The addition of 2% KOH to methoxytriglycol resulted in an amber color even at room temperature. Therefore, the amount of KOH in the hydroformylation experiments was minimized.

To the reaction mixture from the above aldolization experiment, the hydroformylation catalyst of the previous example was added. Then the mixture as pressured to 570 psi (39 atm) and heated as usual to 120° C. with a 20/1 mixture of $H_2/CO$. A high $H_2/CO$ ratio was used to increase the hydrogenation rate of the n,n-enal to the n,n-anal.

The hydrogenation of the n,n-enal to the n,n-anal was followed by glc. During the first 90 minutes, the percentage conversion increased as follows: 6% (5 min.); 13% (20 min.); 21% (40 min.); 28% (60 min.); and 39% (90 min.). Under these conditions, no further significant aldolization of the n-$C_5$ aldehyde occurred.

EXAMPLE 57

Combined Hydroformylation-Aldolization of 1-Butene with Various Tris-(Alkyl Diphenyl Phosphine) Rhodium Carbonyl Hydride Complexes The combined hydroformylation aldolization of 1-butene under the conditions of Example 56 was also studied with the tris-(n-butyl diphenyl phosphine) and the tris-(n-hexyl diphenyl phosphine) complexes. The SEP complex was also used in this group of experiments under similar conditions but using a 1/1 rather than a 5/1 initial $H_2/CO$ reactant ratio. The results are shown in Table XVII.

Overall, the data of the Table show that different alkyl diphenyl phosphine complexes are similar catalysts for combined hydroformylation aldolization. The results also indicate that the provision of sufficient carbon monoxide for hydroformylation is a key factor in avoiding olefin hydrogenation.

The first two experiments seq. Nos. 1 and 2) with the butyl diphenyl phosphine complex A) show the effect of the KOH on the aldolization. The results are similar to those obtained in comparative experiments using the SEP complex in a previous example (see Table I). The second pair (Seq. Nos. 3 and 4) shows the effect of starting with a synthesis gas having a low, i.e., B 1.5, $H_2/CO$ ratio. Lower selectivities to the n-product are obtained but the reaction rates are increased and the by-product are obtained but the reaction rates are increased and the by-product n-butane formation is drastically reduced. The two different catalyst ligands used in these experiments, i.e., n-hexyl diphenyl phosphine (B) and trimethylsilylethyl phosphine (C), led to similar results.

EXAMPLE 58

Combined Hydroformylation Aldolization of 1-Butene at 145° C. in the Presence of Tris-SEP and Tris-TPP Rhodium Carbonyl Hydride Complexes The combined hydroformylation-aldolization of 1-butene was also studied under similar conditions at 145° C. At this temperature, the known tris-TPP complex is unstable under the reaction conditions. In contrast, the novel tris-SEP complex is stable under the reaction conditions. In contrast, the novel tris-SEP complex is stable. The experimental conditions and results are shown in Table XVIII.

As it is shown by the table, in the first pair of experiments (Seq. Nos 1 and 2), both the triphenyl phosphine (TPP) complex and the trimethylsilylethyl diphenyl phosphine (SEP) complex were employed as hydroformylation catalysts in methoxytriglycol in the absence of KOH. A comparison of the results showed that the rate of the SEP complex catalyzed reaction was higher. Even more significantly, the selectivity' of the SEP complex to produce aldehydes of high n/i ratios was much higher (Seq. No. 1). At 80% conversion, the SEP catalyzed reaction had a 7.6 n/i ratio. The comparable ratio for the TPP system was 3.1 (Seq. No. 2). Most revealingly, the TPP reaction gave an n/i ration of 12.4 at 15% conversion. Apparently, during the further course of the experiment, the TPP catalyst system decomposed and led to species of much lower catalytic activity and selectivity.

In the second pair of experiments (Seq. Nos. 3 and 4), the same two catalyst systems were employed in the presence of KOH to effect hydroformylation and aldol-

TABLE XVII

Combined Hydroformylation Aldolization of 1-Butene at 120° C., in the Presence of Various tris-(Alkyl Diphenyl Phosphine) Rhodium Carbonyl Hydride Complexes L = $Ar_2PR$; A: R = $C_4H_9$; B: R = $C_6H_{13}$; C: R = $CH_2CH_2Si(CH_3)_3$; L/Rh = 140; Rh = 110 ppm; Pressure = 350 psi (26 atm)

| Seq. No | Run No. 7132 | Ligand Species | KOH % | $H_2/CO$ Ratio Initial | Feed | Final | Rate Constant k, min$^{-1}$ | Fraction $H_2/CO$ Reacted Conversion % | Reaction Time Min. | $C_5$'s i- | n | $C_{10}$'s n,n(i) anal | n,n- enal | n/i Ratio | % n 100n n + 1 | Selectivity to n-Butane mole % |
|---|---|---|---|---|---|---|---|---|---|---|---|---|---|---|---|---|
| 1 | 303 | A | Nil | 5 | 1.5 | 20.1 | 0.058 | 15 | 4 | 4.9 | 95.1 | | | 19.6 | 95.1 | |
| | | | | | | | | 80 | 34 | 4.4 | 95.6 | | | 21.9 | 95.6 | 13.0 |
| 2 | 290 | A | 0.1 | 5 | 1.5 | 21.0 | 0.043 | 15 | 5 | 10.7 | 16.8 | 7.3 | 65.2 | 15.1 | 93.8 | |
| | | | | | | | | 80 | 42 | 6.7 | 24.5 | 21.9 | 46.9 | 24.1 | 96.0 | 13.7 |
| 3 | 299 | B | 0.1 | 1.5 | 1.5 | 11.6 | 0.151 | 15 | 2 | 18.5 | 75.2 | | 7.3 | 4.8 | 82.8 | |
| | | | | | | | | 80 | 12 | 14.1 | 63.1 | 6.7 | 16.0 | 7.7 | 88.5 | 1.9 |
| 4 | 293 | C | 0.1 | 1.5 | 1.5 | 6.8 | 0.088 | 15 | 3 | 18.0 | 75.7 | | 6.3 | 4.9 | 83.1 | |
| | | | | | | | | 80 | 20 | 16.0 | 73.6 | 0.9 | 9.5 | 5.9 | 88.5 | |
| | | | | | | | | 109 | 120 | 19.0 | 12.8 | 34.4 | 33.8 | 7.5 | 88.2 | 2.1 | ization. KOH was found to be an effective a aldolization catalyst. Both complexes were also effective in catalyzing the hydrogenation of the aldol condensation products. However, the difference between the activity and selectivity of the two catalysts remained. The SEP complex plus KOH system produced a 6.6 n/i ratio of aldehydes at 80% conversion (Seq. No. 3). The comparative n/i ratio for the TPP complex plus base was only 4.2 (Seq. No. 4).

than 140 and wherein the process temperature is between 120° to 175° C.

4. The process of claim 1 wherein the catalyst complex is tris(2-trimethylsilylethyl diphenyl phosphine) rhodium carbonyl hydride.

5. The process of claim 1 wherein said liquid reaction mixture is a homogeneous phase.

6. The process of claim 1 wherein said aldol condensation catalyst is KOH present in about 0.05 to 0.5

TABLE XVIII

Combined Hydroformylation Aldolization of 1-Butene at 145° C. and 350 psi (~26 atm.) in the Presence of tris-SEP and tris-TPP Rhodium Carbonyl Hydride Complexes SEP = $Ph_2PCH_2CH_2Si(CH_3)_3$; TPP = $Ph_3P$; L/Rh = 140; Rh = 110 ppm

| Seq. No | Run No. 7132 | Ligand Species | KOH % | H2/CO Ratio Initial | H2/CO Ratio Feed | H2/CO Ratio Final | Fraction H2/CO Reacted Rate Constant k, min$^{-1}$ | Con- version % | Re- action Time Min. | C5's i- | C5's n | C10's n,n(i) anal | C10's n,n- enal | n/i Ratio | % n 100n n + 1 | Select- ivity to n- Butane mole % |
|---|---|---|---|---|---|---|---|---|---|---|---|---|---|---|---|---|
| 1 | 238 | SEP | Nil | 5 | 1.17 | 2.7 | 0.174 | 79 | 18 | 11.6 | 88.4 | | | 7.6 | 88.6 | 12.0 |
| 2 | | TPP | Nil | 5 | 1.5 | 14.7 | 0.138 | 15 | 1 | 7.5 | 92.5 | | | 12.4 | 92.5 | |
| | | | | | | | | 80 | 90 | 24.6 | 75.4 | | | 3.1 | 75.4 | 15.4 |
| 3 | 262 | SEP | 0.2 | 5 | 1.5 | 4.6 | 0.07 | 80 | 42 | 15.2 | 21.1 | 44.4 | 19.4 | 6.7 | 87.0 | 19.4 |
| 4 | 295 | TPP | 0.1 | 5 | 1.5 | 6.4 | 0.121 | 15 | 1.5 | 8.6 | 38.4 | 3.0 | 50.0 | 16.8 | 94.4 | |
| 4 | 295 | TPP | 0.1 | 5 | 1.5 | 6.4 | 0.121 | 15 | 1.5 | 8.6 | 38.4 | 3.0 | 50.0 | 16.8 | 94.4 | |
| | | | | | | | | 80 | 80 | 29.7 | 12.0 | 48.5 | 9.8 | 4.2 | 80.6 | 13.2 |

The above quantitative observations on the relative stability of the SEP and TPP based systems could be qualitatively predicted when observing the respective reaction mixtures after the reactions. The SEP systems without and with base were yellow and amber, respectively. The TPP systems with and without base became black.

What is claimed is:

1. A combined hydroformylation-aldolization process for converting, a $C_n$ olefin to a $C_{2n+2}$ aldehyde comprising the steps of:
   (a) reacting said olefin with CO and $H_2$ at a temperature in the range of about 50° to 200° C. and a total pressure in the range of about 15 to 2000 psia in a reaction zone containing a liquid reaction mixture comprising a base aldol condensation catalyst and a homogeneous, non-charged catalyst complex of the formula:

$[(Ar_2PQ)_ySiR_{4-y}]_g \cdot (RhX_n)_s$ wherein Ar is a substituted or unsubstituted $C_6$ to $C_{10}$ aromatic radical, Q is an unsubstituted or substituted $C_1$ to $C_{30}$ saturated open chain alkylene radical; R is an unsubstituted or monosubstituted $C_1$ to $C_{10}$ hydrocarbyl radical, X is an anion or organic ligand, excluding halogen, satisfying the valence and coordination sites of the metal, y is 1 to 6, g is 1 to 6 with the proviso that g times y is 1 to 6, n is 2 to 6, s is 1 to 3, said substituents on said hydrocarbyl radical, being chemically unreactive with materials used in and the products of the hydroformylation reaction, and
   (b) withdrawing said liquid reaction mixture from said reaction zone and recovering said $C_{2n+2}$ aldehyde.

2. The process of claim 1 wherein said hydroformylation products further comprise hydrogenation products of said $C_{2n+2}$ aldehydes.

3. The process of claim 1 wherein the H2/CO ratio is greater than three, the ligand/Rh molar ratio is greater weight percent of the total liquid reaction mixture.

7. The process of claim 1 wherein said liquid reaction mixture contains an ether-alcohol solvent.

8. The process of claim 1 wherein said catalyst is of the formula:

$\{[Ph_2P(CH_2)_m]_ySi(CH_3)_{4-y}\}_gRh(CO)H$ wherein m is 2–14, Ph is phenyl, and y and g are as described above in claim 9.

9. The process of claim 1 wherein said olefin is a terminal olefin.

10. The process of claim 1 wherein said olefin is a mixture of butene-1 and cis- and trans-butene-2.

11. The process of claim 1 wherein said catalyst is of the formula:

$[[Ph_2P(CH_2)_m]_ySi(CH_3)_{4-y}]_gRh(CO)H$ wherein m is 2–14, Ph is phenyl, y is 1 to 3 and g is 2 or 3.

12. The process of claim 1 wherein said olefin is a terminal olefin.

13. The process of claim 1 wherein said olefin is a mixture of butene-1 and cis- and trans-butene-2.

14. A combined hydroformylation-aldolization process for converting a $C_n$ olefin feed, said olefin being a terminal or internal olefin or mixture thereof, to a $C_{2n+2}$ aldehyde comprising the steps of:
   (a) reacting said olefin with CO and $H_2$ at a temperature in the range of about 120° to 175° C. and a total pressure in the range of about 15 to 2000 psia in a reaction zone containing a liquid reaction mixture comprising a base aldol condensation catalyst and a homogeneous, non-charged hydroformylation catalyst complex of the formula:

$[[Ar_2P(CH_2)_m]_ySiR_{4-y}]_3Rh(CO)H$ wherein Ar is a substituted or unsubstituted $C_6$ to $C_{10}$ aromatic radical, R is an unsubstituted or monosubstituted $C_1$ to $C_{10}$ hydrocarbyl radical, m is 2 to 14, y is 1 to 4; said substituents on said aromatic radical, and on said hydrocarbyl radical being chemically unreactive with materials used in and the products of a hydroformylation reaction, and (b) withdrawing said liquid reaction mixture from said reaction zone and recovering said $C_{2n+2}$ aldehyde.

15. The process of claim 14 wherein said internal olefin reactant is in admixture with a hydrocarbon selected from the group consisting of terminal olefins, diolefins, $C_1$-$C_{10}$ paraffinic hydrocarbons, aromatic hydrocarbons, or mixtures thereof.

16. The process of claim 14 wherein said process is carried out in a continuous recycle flash off mode of operation wherein said withdrawn liquid reaction mixture is further heated under reduced pressure to continuously recover product aldehyde and recovered catalyst is recirculated back to said liquid reaction mixture.

* * * * *